US010330531B2

(12) United States Patent
Goldring et al.

(10) Patent No.: US 10,330,531 B2
(45) Date of Patent: Jun. 25, 2019

(54) SPECTROMETRY SYSTEM APPLICATIONS

(71) Applicant: VERIFOOD, Ltd., Herzliya (IL)

(72) Inventors: Damian Goldring, Tel Aviv (IL); Dror Sharon, Benai Atarot (IL); Sagee Rosen, Netzer Sireni (IL); Ittai Nir, Tel Aviv (IL); Uri Kinrot, Hod HaSharon (IL); Omer Keilaf, Kfar Saba (IL); Guy Brodetzki, Rehovot (IL); Assaf Carmi, Modiin (IL); Oren Buskila, Givataim (IL)

(73) Assignee: VERIFOOD, LTD., Herzliya (IL)

( * ) Notice: Subject to any disclaimer, the term of this patent is extended or adjusted under 35 U.S.C. 154(b) by 0 days.

(21) Appl. No.: 15/667,489

(22) Filed: Aug. 2, 2017

(65) Prior Publication Data
US 2018/0143073 A1 May 24, 2018

Related U.S. Application Data

(63) Continuation of application No. PCT/IL2016/050129, filed on Feb. 4, 2016.
(Continued)

(51) Int. Cl.
*G01J 3/02* (2006.01)
*G01N 21/31* (2006.01)
(Continued)

(52) U.S. Cl.
CPC ........... *G01J 3/0256* (2013.01); *G01J 3/0205* (2013.01); *G01J 3/0272* (2013.01); *G01J 3/0289* (2013.01);
(Continued)

(58) Field of Classification Search
USPC .......................................................... 356/326
See application file for complete search history.

(56) References Cited

U.S. PATENT DOCUMENTS 6,069,696 A 5/2000 McQueen et al.
6,072,576 A 6/2000 McDonald et al.
(Continued)

FOREIGN PATENT DOCUMENTS

WO WO-2013065035 A1 5/2013
WO WO-2013082272 A1 6/2013
(Continued)

OTHER PUBLICATIONS

SCIOYour Sixth Sense, Water Available at https://www.youtube.com/watch?v=UIFyAOD_E3E>.times O:OOs to 2:40s, Accessed on May 9, 2014.
(Continued)

*Primary Examiner* — Hina F Ayub
(74) *Attorney, Agent, or Firm* — Wilson Sonsini Goodrich & Rosati

(57) ABSTRACT

A spectrometer system may be used to determine one or more spectra of an object, and the one or more spectra may be associated with one or more attributes of the object that are relevant to the user. While the spectrometer system can take many forms, in many instances the system comprises a spectrometer and a processing device in communication with the spectrometer and with a remote server, wherein the spectrometer is physically integrated with an apparatus. The apparatus may have a function different than that of the spectrometer, such as a consumer appliance or device.

3 Claims, 45 Drawing Sheets

Related U.S. Application Data

(60) Provisional application No. 62/190,535, filed on Jul. 9, 2015, provisional application No. 62/112,597, filed on Feb. 5, 2015, provisional application No. 62/112,582, filed on Feb. 5, 2015.

(51) Int. Cl.
- *G01N 21/3563* (2014.01)
- *G01N 21/359* (2014.01)
- *G01J 3/10* (2006.01)
- *G01J 3/36* (2006.01)
- *G01J 3/28* (2006.01)
- *G01J 3/42* (2006.01)

(52) U.S. Cl.
CPC .............. *G01J 3/0291* (2013.01); *G01J 3/10* (2013.01); *G01J 3/2803* (2013.01); *G01J 3/36* (2013.01); *G01J 3/42* (2013.01); *G01N 21/31* (2013.01); *G01N 21/359* (2013.01); *G01N 21/3563* (2013.01); *G01N 2201/0221* (2013.01); *G01N 2201/0625* (2013.01); *G01N 2201/0627* (2013.01); *G01N 2201/121* (2013.01)

(56) References Cited

U.S. PATENT DOCUMENTS

| | | |
|---|---|---|
| 6,333,501 B1 | 12/2001 | Labrenz |
| 6,441,375 B1 | 8/2002 | Joseph et al. |
| 6,456,373 B1 | 9/2002 | Wienecke et al. |
| 6,615,142 B1 | 9/2003 | Hovde |
| 6,639,666 B2 | 10/2003 | Li |
| 6,700,661 B1 | 3/2004 | Cadell et al. |
| 6,717,669 B2 | 4/2004 | Ruiz |
| 6,836,325 B2 | 12/2004 | MacZura et al. |
| 6,864,978 B1 | 3/2005 | Hazen et al. |
| 7,009,702 B2 | 3/2006 | Caruso et al. |
| 7,038,774 B2 | 5/2006 | Hazen et al. |
| 7,068,366 B2 | 6/2006 | Burk et al. |
| 7,075,643 B2 | 7/2006 | Holub |
| 7,084,974 B1 | 8/2006 | Barwicz et al. |
| 7,145,650 B2 | 12/2006 | Wang et al. |
| 7,151,600 B2 | 12/2006 | Imura |
| 7,158,225 B2 | 1/2007 | Tedesco et al. |
| 7,235,766 B2 | 6/2007 | Shur et al. |
| 7,236,243 B2 | 6/2007 | Beecroft et al. |
| 7,245,372 B2 | 7/2007 | Han |
| 7,248,370 B2 | 7/2007 | Jones |
| 7,251,037 B2 | 7/2007 | Jones |
| 7,339,665 B2 | 3/2008 | Imura |
| 7,426,446 B2 | 9/2008 | Hagler |
| 7,436,511 B2 | 10/2008 | Ruchti et al. |
| 7,489,396 B1 | 2/2009 | Vrhel et al. |
| 7,528,957 B2 | 5/2009 | Lewis et al. |
| 7,649,627 B2 | 1/2010 | Yamamoto |
| 7,697,136 B2 | 4/2010 | Imura |
| 7,767,969 B2 | 8/2010 | Nagai et al. |
| 7,817,273 B2 | 10/2010 | Bahatt et al. |
| 7,868,296 B2 | 1/2011 | Haran et al. |
| 7,876,435 B2 | 1/2011 | Becker-Ross et al. |
| 7,881,892 B2 | 2/2011 | Soyemi et al. |
| 7,907,282 B2 | 3/2011 | Coates |
| 7,929,130 B2 | 4/2011 | Dirk |
| 7,999,933 B2 | 8/2011 | McClure |
| 8,125,633 B2 | 2/2012 | Whelan et al. |
| 8,144,322 B2 | 3/2012 | Nagashima et al. |
| 8,169,607 B2 | 5/2012 | Sano et al. |
| 8,169,608 B2 | 5/2012 | Sano et al. |
| 8,247,774 B2 | 8/2012 | Chou et al. |
| 8,284,401 B2 | 10/2012 | Choi et al. |
| 8,477,305 B2 | 7/2013 | Shibayama et al. |
| 8,526,002 B2 | 9/2013 | Deflores et al. |
| 8,593,628 B2 | 11/2013 | Shimbo et al. |
| 8,604,412 B2 | 12/2013 | Shibayama et al. |
| 8,654,327 B2 | 2/2014 | Bohle et al. |
| 8,675,188 B2 | 3/2014 | Liu et al. |
| 8,711,360 B2 | 4/2014 | Funamoto |
| 8,711,362 B2 | 4/2014 | Funamoto |
| 8,735,820 B2 | 5/2014 | Mertens |
| 8,742,320 B2 | 6/2014 | Shibayama et al. |
| 8,760,645 B2 | 6/2014 | Misener et al. |
| 8,773,659 B2 | 7/2014 | McClure |
| 8,786,854 B2 | 7/2014 | Miyazono |
| 8,843,161 B2 | 9/2014 | Kirik et al. |
| 8,848,187 B2 | 9/2014 | Uematsu et al. |
| 8,862,445 B2 | 10/2014 | Priore et al. |
| 8,867,033 B2 | 10/2014 | Carron et al. |
| 8,868,387 B2 | 10/2014 | Den Boef et al. |
| 8,873,046 B2 | 10/2014 | Miyazono |
| 8,937,717 B2 | 1/2015 | Preston et al. |
| 8,976,357 B2 | 3/2015 | Uematsu et al. |
| 9,030,662 B2 | 5/2015 | Lee et al. |
| 9,060,113 B2 | 6/2015 | Rhoads et al. |
| 9,063,011 B2 | 6/2015 | Chen et al. |
| 9,074,933 B2 | 7/2015 | Yokino et al. |
| 9,128,055 B2 | 9/2015 | Sekino et al. |
| 9,163,986 B2 | 10/2015 | Bouckaert |
| 9,173,508 B2 | 11/2015 | Tornwall et al. |
| 9,182,280 B1 | 11/2015 | Gardner et al. |
| 9,234,800 B2 | 1/2016 | Kawamata et al. |
| 9,239,264 B1 | 1/2016 | Demers |
| 9,297,821 B2 | 3/2016 | Walter et al. |
| 9,301,626 B2 | 4/2016 | Tornwall et al. |
| 9,310,564 B2 | 4/2016 | Martinelli et al. |
| 9,383,308 B2 | 7/2016 | Bradley et al. |
| 9,395,244 B2 | 7/2016 | Kurokawa et al. |
| 9,417,180 B2 | 8/2016 | Seo et al. |
| 9,448,165 B2 | 9/2016 | Gulati et al. |
| 9,453,794 B2 | 9/2016 | Gulati et al. |
| 9,464,934 B2 | 10/2016 | Priore et al. |
| 9,488,468 B2 | 11/2016 | Tsujii et al. |
| 9,488,523 B2 | 11/2016 | Yokino et al. |
| 9,508,765 B2 | 11/2016 | Owa et al. |
| 9,518,917 B2 | 12/2016 | Scherer et al. |
| 9,546,902 B2 | 1/2017 | Kovacich et al. |
| 9,546,904 B2 | 1/2017 | Pawluczyk et al. |
| 9,557,220 B2 | 1/2017 | Yasui et al. |
| 9,568,363 B2 | 2/2017 | Yu et al. |
| 2005/0117151 A1 | 6/2005 | Han |
| 2005/0128477 A1 | 6/2005 | Caruso et al. |
| 2006/0132760 A1 | 6/2006 | Imura |
| 2008/0265146 A1 | 10/2008 | Coates |
| 2008/0297791 A1 | 12/2008 | Imura |
| 2009/0051910 A1 | 2/2009 | Imura |
| 2009/0284216 A1* | 11/2009 | Bessa ............... H02J 7/0044 320/101 |
| 2010/0165337 A1 | 7/2010 | Dirk |
| 2010/0292581 A1 | 11/2010 | Howard et al. |
| 2010/0309454 A1 | 12/2010 | Zhang |
| 2011/0037975 A1 | 2/2011 | McClure |
| 2013/0023307 A1* | 1/2013 | Zimmerman ......... G03B 21/28 455/557 |
| 2013/0107260 A1 | 5/2013 | Nozawa |
| 2013/0182250 A1 | 7/2013 | McClure |
| 2013/0258341 A1 | 10/2013 | Day et al. |
| 2014/0046630 A1 | 2/2014 | Smith et al. |
| 2014/0061486 A1 | 3/2014 | Bao et al. |
| 2014/0168636 A1 | 6/2014 | Funamoto et al. |
| 2014/0293091 A1 | 10/2014 | Rhoads et al. |
| 2014/0333932 A1 | 11/2014 | Uematsu et al. |
| 2015/0036138 A1 | 2/2015 | Watson et al. |
| 2015/0062577 A1 | 3/2015 | Hartwell et al. |
| 2015/0103354 A1 | 4/2015 | Saptari et al. |
| 2015/0108333 A1 | 4/2015 | Bouckaert |
| 2015/0116707 A1 | 4/2015 | Tatsuda |
| 2015/0119661 A1 | 4/2015 | Gilbert et al. |
| 2015/0153225 A1 | 6/2015 | Baudelet |
| 2015/0220068 A1* | 8/2015 | Goldman-Shenhar ......... G06N 99/005 700/29 |
| 2015/0323383 A1 | 11/2015 | Pastore et al. |
| 2016/0018260 A1 | 1/2016 | Samuels |
| 2016/0091369 A1 | 3/2016 | Sakurai et al. |

(56) References Cited

U.S. PATENT DOCUMENTS

| | | | |
|---|---|---|---|
| 2016/0103069 A1 | 4/2016 | Umapathy et al. | |
| 2016/0109371 A1* | 4/2016 | Blair | G01N 21/645 436/172 |
| 2016/0139927 A1* | 5/2016 | Gschwind | G06F 9/30101 712/213 |
| 2016/0223400 A1 | 8/2016 | Carron et al. | |
| 2016/0231171 A1 | 8/2016 | Assefa et al. | |
| 2016/0245700 A1 | 8/2016 | Uematsu et al. | |
| 2016/0258813 A1 | 9/2016 | Kuri | |
| 2016/0263910 A1 | 9/2016 | Kanai et al. | |
| 2016/0282182 A1 | 9/2016 | Kanai et al. | |
| 2016/0299004 A1 | 10/2016 | Thamm | |
| 2016/0305820 A1 | 10/2016 | Zollars et al. | |
| 2016/0313184 A1 | 10/2016 | Owechko | |
| 2016/0334274 A1 | 11/2016 | Xu | |
| 2016/0356646 A1 | 12/2016 | Wiegand et al. | |
| 2016/0356647 A1 | 12/2016 | Wiegand et al. | |
| 2016/0356704 A1 | 12/2016 | Kim et al. | |
| 2017/0003167 A1 | 1/2017 | Ave | |
| 2017/0027447 A1 | 2/2017 | Sutin et al. | |
| 2017/0038257 A1 | 2/2017 | Liu et al. | |
| 2017/0085733 A1* | 3/2017 | Ilic | G06T 19/20 |

FOREIGN PATENT DOCUMENTS

| | | |
|---|---|---|
| WO | WO-2013106307 A1 | 7/2013 |
| WO | WO-2013148461 A1 | 10/2013 |
| WO | WO-2013150290 A1 | 10/2013 |
| WO | WO-2013162850 A1 | 10/2013 |
| WO | WO-2013163268 A1 | 10/2013 |
| WO | WO-2013165887 A1 | 11/2013 |
| WO | WO-2014014534 A2 | 1/2014 |
| WO | WO-2014033783 A1 | 3/2014 |
| WO | WO-2014014534 A3 | 4/2014 |
| WO | WO-2014064447 A1 | 5/2014 |
| WO | WO-2014102629 A1 | 7/2014 |
| WO | WO-2014129305 A1 | 8/2014 |
| WO | WO-2014139003 A1 | 9/2014 |
| WO | WO-2014165331 A1 | 10/2014 |
| WO | WO-2014192007 A1 | 12/2014 |
| WO | WO-2015009602 A1 | 1/2015 |
| WO | WO-2015038372 A1 | 3/2015 |
| WO | WO-2015042617 A1 | 3/2015 |
| WO | WO-2015058166 A2 | 4/2015 |
| WO | WO-2015058166 A3 | 6/2015 |
| WO | WO-2015138028 A2 | 9/2015 |
| WO | WO-2015138028 A3 | 11/2015 |
| WO | WO-2016022283 A1 | 2/2016 |
| WO | WO-2016033224 A1 | 3/2016 |
| WO | WO-2016059946 A1 | 4/2016 |
| WO | WO-2016124659 A1 | 8/2016 |
| WO | WO-2016125164 A2 | 8/2016 |
| WO | WO-2016196727 A2 | 12/2016 |
| WO | WO-2016125164 A3 | 1/2017 |
| WO | WO-2016196727 A3 | 1/2017 |

OTHER PUBLICATIONS

International search report and written opinion dated Sep. 7, 2016 for PCT Application IL-2016050129.

\* cited by examiner

SPECTROMETRY SYSTEM APPLICATIONS

CROSS-REFERENCE

The present application is a continuation of International Patent Application No. PCT/IL2016/050129, filed Feb. 4, 2016, entitled "SPECTROMETRY SYSTEM APPLICATIONS", which claims the benefit of U.S. Provisional Application Ser. No. 62/112,597, filed on Feb. 5, 2015, entitled "Spectrometry System Performance and Characteristics of Applications", U.S. Provisional Application Ser. No. 62/112,582, filed on Feb. 5, 2015, entitled "Embedded Applications for Spectrometry System", and U.S. Provisional Application Ser. No. 62/190,535, filed on Jul. 9, 2015, entitled "Smartphone-Integrated Spectrometer", the entire disclosures of each of which are incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Spectrometers are used for many purposes. For example, spectrometers are used in the detection of defects in industrial processes, satellite imaging, and laboratory research. However, these instruments have typically been too large and too costly for the consumer market.

Spectrometers detect radiation from a sample and process the resulting signal to obtain and present information about the sample that includes spectral, physical and chemical information about the sample. These instruments generally include some type of spectrally selective element to separate wavelengths of radiation received from the sample, and a first-stage optic, such as a lens, to focus or concentrate the radiation onto an imaging array.

The prior spectrometers can be less than ideal in at least some respects. Prior spectrometers having high resolution can be larger than ideal for use in many portable applications. Although prior spectrometers with decreased size have been proposed, the prior spectrometers having decreased size and optical path length can have less than ideal resolution, sensitivity and less accuracy than would be ideal. Also, the cost of prior spectrometers can be greater than would be ideal. The prior spectrometers can be somewhat bulky, difficult to transport and the optics can require more alignment than would be ideal in at least some instances. Because of their size and cost, prior spectrometers can be difficult to integrate into other consumer appliances or devices in which a spectrometer may be useful.

Further, data integration of prior spectrometers with measured objects can be less than ideal in at least some instances. For example, although prior spectrometers can provide a spectrum of a measured object, the spectrum may be of little significance to at least some users. It would be helpful if a spectrum of a measured object could be associated with attributes of the measured object that are useful to a user. For example, although prior spectrometers may be able to measure sugar, it would be helpful if a spectrometer could be used to determine the sweetness of an object such as an apple. Many other examples exist where spectral data alone does not adequately convey relevant attributes of an object, and it would be helpful to provide attributes of an object to a user in response to measured spectral data.

Prior spectrometer apparatus can be less than ideally suited for at least some applications. For example, a hand held spectrometer apparatus may be less than ideally suited for at least some embedded applications. Also, the prior spectrometer methods and apparatus may be less than ideally integrated with a measurement environment.

In light of the above, an improved spectrometer and interpretation of spectral data that overcomes at least some of the above mentioned deficiencies of the prior spectrometers would be beneficial. Ideally, such a spectrometer would be compact, capable of being physically integrated with other consumer appliances or devices, sufficiently rugged and low in cost to be practical for end-user spectroscopic measurements of items, and convenient to use. Ideally, such a compact spectrometer would have sufficient sensitivity for the use of the spectrometer in specific applications. Further, it would be helpful to provide data comprising attributes of measured objects related to the spectral data of the objects to many people. It would also be useful to provide a compact spectrometer with decreased dependence on an internet connection at the time of measurement for the analysis of measurement data.

SUMMARY OF THE INVENTION

The present disclosure provides improved spectrometer systems and methods. A spectrometer system may be used to determine one or more spectra of an object, and the one or more spectra may be associated with one or more attributes of the object that are relevant to the user. While the spectrometer system can take many forms, in many instances the system comprises a spectrometer and a processing device in communication with the spectrometer and with a remote server. The spectrometer can be configured to measure the spectra of a sample while the processing device is not connected to the remote server, so that spectral measurements can be performed whether or not a user of the spectrometer system has access to an internet connection. The spectrometer system can be configured to have a sensitivity that makes the system suitable for use in various specific applications, such as the detection of melamine contaminants in milk, the detection of urine components for urine analysis, and the detection of oxidation levels of edibles oils.

The spectrometer may comprise a compact hand held spectrometer. Alternatively, the spectrometer may be physically integrated with an apparatus, wherein the apparatus may have a function different than that of the spectrometer, such as a consumer appliance or device. The processing device may comprise instructions to transmit the spectral data of the sample to the remote server and receive object data in response. The object data may be displayed to the user through the processing device, the spectrometer, or the apparatus with which the spectrometer is integrated. Such physical integration of the spectrometer system with a consumer appliance or device can provide a convenient way for users to measure the spectra of sample objects.

In one aspect, a system to measure spectra of a sample comprises a spectrometer to measure the spectra of the sample and a processing device coupled to the spectrometer. The processing device comprises a processor and a wireless communication circuitry to couple to the spectrometer and communicate with a remote server. The processor comprises instructions to transmit spectral data of the sample to the remote server and receive object data in response to the spectral data from the remote server. The spectrometer is functionally integrated with a smartphone, and information obtained with the spectrometer is provided to a functional feature of the smartphone to improve a performance of the functional feature of the smartphone.

The functional feature of the smartphone may comprise a software application installed in the smartphone and configured to provide one or more services to a user of the smartphone. The information obtained with the spectrometer may comprise one or more of an identification of the sample, an identification of one or more components of the sample, a quantification of the sample, a quantification of one or more components of the sample, and a determination of one or more secondary characteristics of the sample. The software application may use the information obtained with the spectrometer to improve an accuracy or reliability of the service provided to the user, or to increase a quantity or quality of information provided to the user.

The functionality of the smartphone may comprise a camera, and the information obtained with the spectrometer may be provided to the camera to improve a color correction algorithm of the camera. The color correction algorithm may comprise a white balancing algorithm. The information obtained with the spectrometer may comprise one or more illumination types of one or more sources of illumination present in a scene imaged by the camera, wherein the one or more illumination types may be determined via an analysis of the spectral data of the scene obtained with the spectrometer. The spectrometer or another computing device in communication with the spectrometer may be configured to determine the one or more illumination types by identifying one or more spectral signatures of the one or more illumination types present in a near-infrared spectrum of the spectral data of the scene.

In another aspect, a system to measure spectra of a sample may comprise a spectrometer to measure the spectra of the sample and a processing device coupled to the spectrometer, wherein the spectrometer is physically integrated with an apparatus. The processing device may comprise a processor and a wireless communication circuitry to couple to the spectrometer and communicate with a remote server. The processor may comprise instructions to transmit spectral data of the sample to the remote server and receive object data in response to the spectral data from the remote server. The apparatus with which the spectrometer is integrated may comprise a function that does not comprise measuring the spectra of the sample.

The spectrometer may comprise a stand-alone unit that is removably coupled to a portion of the apparatus. The stand-alone spectrometer may be sized to fit within a hand of the user to allow the user to aim the spectrometer at the sample and measure the sample. The stand-alone spectrometer may be removably coupled to a docking station disposed on the portion of the apparatus to which the spectrometer is coupled. The docking station may be configured to charge a battery of the spectrometer when the spectrometer is coupled to the docking station.

The spectrometer may be non-removably coupled to a portion of the apparatus. One or more components of the spectrometer may be arranged in a custom configuration to fit a specific size or shape of the apparatus.

The processing device may comprise a mobile communication device. Alternatively or in combination, the processing device may comprise a portion of the apparatus, or a portion of the spectrometer.

The apparatus may comprise a refrigerator. The spectrometer may be removably coupled to a handle of a refrigerator door, or to an interior compartment of the refrigerator. One or more of the processor of the processing device or a processor of the remote server may comprise instructions to determine one or more of a freshness, safety, or quality of the sample. The refrigerator may further comprise a display screen, configured to display the object data received from the remote server. The display screen may be disposed on a door of the refrigerator, for example. The object data received from the remote server may comprise an indication of one or more of a freshness, safety, or quality of the sample. The object data received from the remote server may further comprise a recommendation for a course of action related to the sample.

The apparatus may comprise a mobile phone case. The mobile phone case may comprise an aperture to accommodate a camera of a mobile phone coupled to the mobile phone case, and the spectrometer may be configured to have a field of view disposed on a same plane as a field of view of the camera. The field of view of the spectrometer and the field of view of the camera may at least partially overlap.

In another aspect, a compact spectrometer may be functionally integrated with a smartphone having one or more functional features, such that the spectrometer and the smartphone may mutually benefit from the functionality provided by one another. For example, a smartphone-integrated spectrometer can use one or more functional features of the smartphone, such as a camera, an accelerometer, or a global positioning system (GPS), to enhance the performance of the spectrometer. Conversely, the smartphone-integrated spectrometer can augment one or more functionalities of the smartphone, for example enhance the performance of a smartphone camera.

In another aspect, a system to measure spectra of a sample comprises a spectrometer and a mobile communication device. The spectrometer may be configured to measure the spectra of the sample. The mobile communication device may comprise a processor and wireless communication circuitry to couple to the spectrometer and communicate with a remote server. The processor can comprise instructions to transmit spectral data of the sample to the remote server. The mobile communication device may be configured to transmit the spectral data to the remote server when the mobile communication device is connected to the remote server.

The spectrometer may be configured to measure the spectra of the sample while the mobile communication device is not connected to the remote server. The mobile communication device may be configured to check whether connection to the remote server is available. The check may be performed at a regular interval, or the check may be performed when the user instructs a user interface of the mobile communication device to perform the check. The mobile communication device may be configured to transmit the spectral data to the remote server when the check determines that a connection to the remote server is available. The mobile communication device may be further configured to synchronize with a database stored on the remote server when the mobile communication device is connected to the remote server.

The remote server may comprise a processor having one or more data analysis algorithms stored thereon. The mobile communication device may be configured to download the one or more data analysis algorithms from the remote server when the mobile communication device is connected to the remote server. The mobile communication device may be further configured to check whether the processor of the mobile communication device has data analysis algorithms stored thereon.

The spectral data transmitted to the remote server may comprise raw spectral data, wherein the spectrometer is configured to measure the spectra of the sample while the mobile communication device is not connected to the remote server. The remote server may be configured to analyze the raw spectral data using one or more spectral data analysis algorithms stored on a memory of the remote server. The remote server may be further configured to add the analyzed spectral data to a database stored on the remote server, and to transmit the analyzed spectral data back to the mobile communication device for display to the user.

The spectral data transmitted to the remote server may comprise analyzed spectral data, wherein the spectrometer is configured to measure the spectra of the sample while the mobile communication device is not connected to the remote server. The analyzed spectral data may comprise raw spectral data analyzed by the processor of the mobile communication device. The processor of the mobile communication device may analyze the raw spectral data using one or more data analysis algorithms stored thereon. The one or more data analysis algorithms may be downloaded from the remote server, or developed by a user of the system.

The spectral data may further comprise metadata. The metadata may include one or more of a date, time, location, temperature, and physical property of the sample.

One or more of the processor of the mobile communication device or a processor of the remote server may comprise instructions to determine a concentration of melamine in milk. The system may be configured to detect at least about 2 ppm, at least about 100 ppm, or at least about 5000 ppm of melamine.

One or more of the processor of the mobile communication device or a processor of the remote server may comprise instructions to determine a concentration of one or more of sodium, potassium, and creatinine in urine. The system may be configured to detect concentrations of sodium of about 10 g/l or less, or about 1.2 g/l or less. The system may be configured to detect concentrations of potassium of about 4 g/l or less, or about 0.6 g/l or less. The system may be configured to detect concentrations of creatinine of about 2.6 g/l or less, or about 0.4 g/l or less.

One or more of the processor of the mobile communication device or a processor of the remote server may comprise instructions to determine a composition level of one or more of total polar compounds or free fatty acids in edible oils. The system may be configured to detect composition levels of total polar compounds of about 27% or less, or about 25% or less. The system may be configured to detect compositions levels of free fatty acids of about 2% or less.

In another aspect, a method of measuring spectra of a sample comprises providing a spectrometer to measure the spectra of the sample, and providing a mobile communication device. The mobile communication device may comprise a processor and wireless communication circuitry to couple to the spectrometer and communicate with a remote server. The processor of the mobile communication device may comprise instructions to transmit spectral data of the sample to the remote server. The method further comprises measuring the spectra of the sample while the mobile communication device is not connected to the remote server. The method further comprises transmitting the spectral data from the mobile communication device to the remote server when the mobile communication device is connected to the remote server.

In another aspect, a method may comprise providing the system of any one of the configurations described herein.

DETAILED DESCRIPTION OF THE INVENTION

Figure 1:
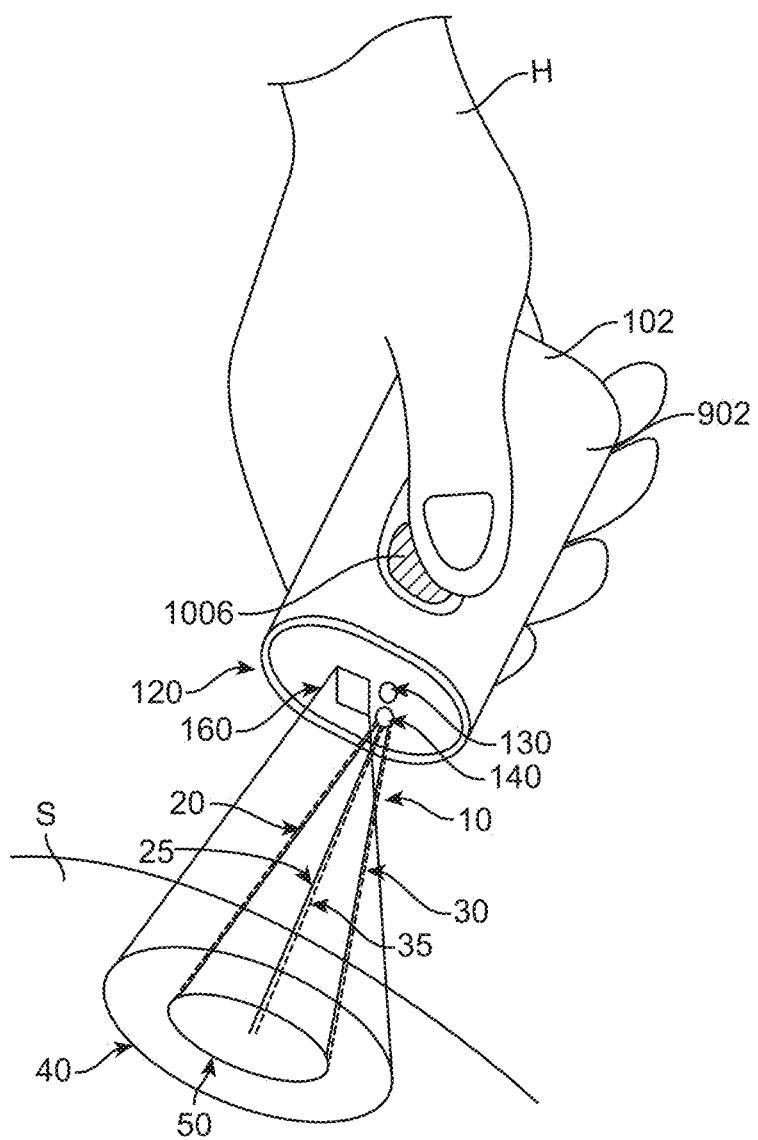
FIG. 1 shows an isometric view of a compact spectrometer, in accordance with configurations.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

A better understanding of the features and advantages of the present disclosure will be obtained by reference to the following detailed description that sets forth illustrative embodiments, in which the principles of embodiments of the present disclosure are utilized, and the accompanying drawings.

The configurations disclosed herein can be combined in one or more of many ways to provide improved spectrometer methods and apparatus. One or more components of the configurations disclosed herein can be combined with each other in many ways. A spectrometer as described herein can be used to generate spectral data of the object, and the spectral data of the object transmitted to a cloud based server in order to determine one or more attributes of the object. Alternatively or in combination, data of the cloud based server can be made available to both users and non-users of the spectrometers in order to provide useful information related to attributes of measured objects. The data of the cloud based server can be made available to users and non-users in many ways, for example with downloadable apps capable of connecting to the cloud based server and downloading information related to spectra of many objects.

The configurations disclosed herein are also capable of providing a database of attributes of many objects related to spectral data. A mobile communication device can be configured for a user to input attributes of one or more measured objects in order to construct a database based on spectral data of many measured objects.

As used herein, like characters refer to like elements. As used herein, the term "light" encompasses electromagnetic radiation having wavelengths in one or more of the ultraviolet, visible, or infrared portions of the electromagnetic spectrum. As used herein, the term "dispersive" is used, with respect to optical components, to describe a component that is designed to separate spatially, the different wavelength components of a polychromatic beam of light. Non-limiting examples of "dispersive" optical elements by this definition include diffraction gratings and prisms. The term specifically excludes elements such as lenses that disperse light because of non-idealities such as chromatic aberration or elements such as interference filters that have different transmission profiles according to the angle of incident radiation. The term also excludes the filters and filter matrixes described herein. As used herein, the term "store" encompasses a structure that stores objects, such as a crate or building.

The dimensions of an optical beam as described herein can be determined in one or more of many ways. The size of the beam may comprise a full width half maximum of the beam, for example. The measurement beam may comprise blurred edges, and the measurement area of the beam defining the measurement area of the sample may comprise a portion of the beam extending beyond the full width half maximum of the beam, for example. The dimensions of the aiming beam can be similarly determined.

Overview of Compact Spectrometer System

FIG. 1 shows an isometric view of a compact spectrometer 102, in accordance with configurations. The spectrometer 102 can be used as a general purpose material analyzer for many applications, as described in further detail herein. In particular, the spectrometer 102 can be used to identify materials or objects, provide information regarding certain properties of the identified materials, and accordingly provide users with actionable insights regarding the identified materials. The spectrometer 102 comprises a spectrometer head 120 configured to be directed towards a sample material S. The spectrometer head 120 comprises a spectrometer module 160, configured to obtain spectral information associated with the sample material S. The spectrometer head 120 may also comprise a sensor module 130, which may, for example, comprise a temperature sensor. The spectrometer may comprise simple means for users to control the operation of the spectrometer, such as operating button 1006. The compact size of the spectrometer 102 can provide a hand held device that can be directed (e.g., pointed) at a material to rapidly obtain information about the material. For example, as shown in FIG. 1, the spectrometer 102 may be sized to fit inside the hand H of a user.

Figure 2:
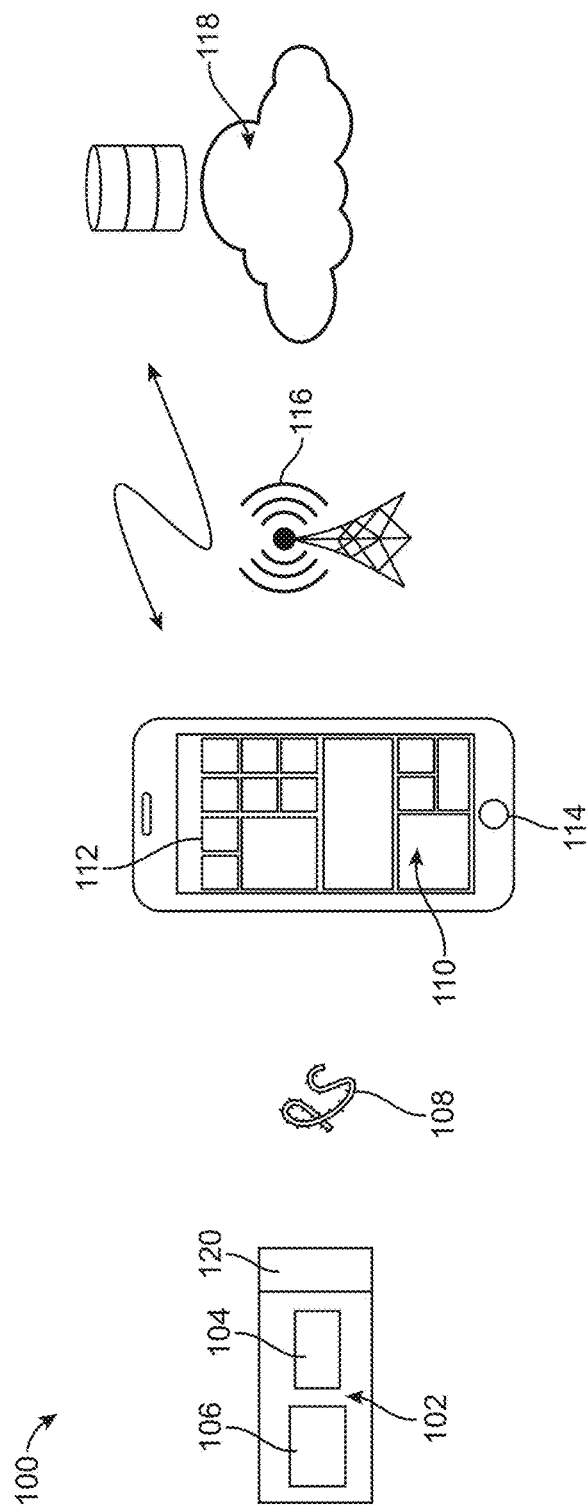
FIG. 2 shows a schematic diagram of a spectrometer system, in accordance with configurations.

FIG. 2 shows a schematic diagram of a spectrometer system, in accordance with configurations. In many instances, the spectrometer system 100 comprises a spectrometer 102 as described herein and a hand held device 110 in wireless communication 116 with a cloud based server or storage system 118. The spectrometer 102 can acquire the data as described herein. The hand held spectrometer 102 may comprise a processor 106 and communication circuitry 104 coupled to the spectrometer head 120 having spectrometer components as described herein. The spectrometer can transmit the data to the hand held device 110 with communication circuitry 104 with a communication link, such as a wireless serial communication link, for example Bluetooth™. The hand held device can receive the data from the spectrometer 102 and transmit the data to the cloud based storage system 118. The data can be processed and analyzed by the cloud based server 118, and transmitted back to the hand held device 110 to be displayed to the user. In addition, the analyzed spectral data and/or related additional analysis results may be dynamically added to a universal database operated by the cloud server 118, where spectral data associated with sample materials may be stored. The spectral data stored on the database may comprise data generated by one or more users of the spectrometer system 100, and/or pre-loaded spectral data of materials with known spectra. The cloud server may comprise a memory having the database stored thereon.

The spectrometer system may allow multiple users to connect to the cloud based server 118 via their hand held devices 110, as described in further detail herein. In some instances, the server 118 may be configured to simultaneously communicate with up to millions of hand held devices 110. The ability of the system to support a large number of users and devices at the same time can allow users of the system to access, in some instances in real-time, large amounts of information relating to a material of interest. Access to such information may provide users with a way of making informed decisions relating to a material of interest.

The hand held device 110 may comprise one or more components of a smart phone, such as a display 112, an interface 114, a processor, a computer readable memory and communication circuitry. The device 110 may comprise a substantially stationary device when used, such as a wireless communication gateway, for example.

The processor 106 may comprise a tangible medium embodying instructions, such as a computer readable memory embodying instructions of a computer program. Alternatively or in combination the processor may comprise logic such as gate array logic in order to perform one or more logic steps.

Figure 3:
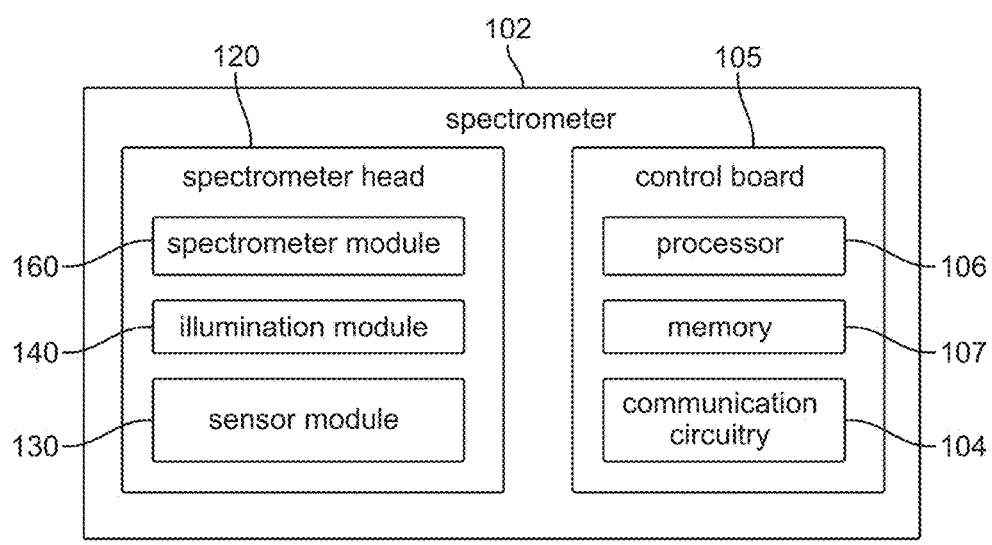
FIG. 3 shows a schematic diagram of the compact spectrometer of FIG. 1, in accordance with configurations.

FIG. 3 shows a schematic diagram of a compact spectrometer of FIG. 1. The spectrometer 102 may comprise a spectrometer head 120 and a control board 105. The spectrometer head 120 may comprise one or more of a spectrometer module 160 and an illumination module 140, which together can be configured to measure spectroscopic information relating to a sample material as described in further detail herein. The spectrometer head 120 may further comprise one or more of a sensor module 130, which can be configured to measure non-spectroscopic information relating to a sample material, such as ambient temperature. The control board 105 may comprise one or more of a processor 106, communication circuitry 104, and memory 107. Components of the control board 105 can be configured to transmit, store, and/or analyze data, as described in further detail herein.

The sensor module 130 can enable the identification of the sample material based on non-spectroscopic information in addition to the spectroscopic information measured by the spectrometer module 160. Such a dual information system may enhance the accuracy of detection or identification of the material.

The sensor element of sensor module 130 may comprise any sensor configured to generate a non-spectroscopic signal associated with at least one aspect of the environment, including the material being analyzed. For example, the sensor element may comprise one or more of a camera, temperature sensor, electrical sensor (capacitance, resistance, conductivity, inductance), altimeter, GPS unit, turbidity sensor, pH sensor, accelerometer, vibration sensor, biometric sensor, chemical sensor, color sensor, clock, ambient light sensor, microphone, penetrometer, durometer, barcode reader, flowmeter, speedometer, magnetometer, and another spectrometer.

The output of the sensor module 130 may be associated with the output of the spectrometer module 160 via at least one processing device of the spectrometer system. The processing device may be configured to receive the outputs of the spectrometer module and sensor module, analyze both outputs, and based on the analysis provide information relating to at least one characteristic of the material to a display unit. A display unit may be provided on the device in order to allow display of such information.

The spectrometer module 160 may comprise one or more lens elements. Each lens can be made of two surfaces, and each surface may be an aspheric surface. In designing the lens for a fixed-focus system, it may be desirable to reduce the system's sensitivity to the exact location of the optical detector on the z-axis (the axis perpendicular to the plane of the optical detector), in order to tolerate larger variations and errors in mechanical manufacturing. To do so, the point-spread-function (PSF) size and shape at the nominal position may be traded off with the depth-of-field (DoF) length. For example, a larger-than-optimal PSF size may be chosen in return for an increase in the DoF length. One or more of the aspheric lens surfaces of each lens of a plurality of lenses can be shaped to provide the increased PSF size and the increased DoF length for each lens. Such a design may help reduce the cost of production by enabling the use of mass production tools, since mass production tools may not be able to meet stringent tolerance requirements associated with systems that are comparatively more sensitive to exact location of the optical detector.

In some cases, the measurement of the sample may be performed using scattered ambient light. In some cases, the spectrometer system may comprise a light or illumination source, such as illumination module 140. The light source can be of any type (e.g., laser, light-emitting diode, etc.) known in the art appropriate for the spectral measurements to be made. The light source may emit from 350 nm to 1100 nm. The light source may emit from 0.1 mW to 500 mW. The wavelength(s) and intensity of the light source can depend on the particular use to which the spectrometer will be put.

The spectrometer may also include a power source, such as a battery or power supply. In some instances the spectrometer is powered by a power supply from a consumer hand held device (e.g. a cell phone). In some instances the spectrometer has an independent power supply. In some instances a power supply from the spectrometer can supply power to a consumer hand held device.

The spectrometer as described herein can be adapted, with proper choice of light source, detector, and associated optics, for a use with a wide variety of spectroscopic techniques. Non-limiting examples include Raman, fluorescence, and IR or UV-VIS reflectance and absorbance spectroscopies. Because, as described herein, a compact spectrometer system can separate a Raman signal from a fluorescence signal, the same spectrometer may be used for both spectroscopies. The spectrometer may not comprise a monochromator.

Referring again to FIG. 1, a user may initiate a measurement of a sample material S using the spectrometer 102 by interacting with a user input supported with a casing or container 902 of the spectrometer. The user input may, for example, comprise an operating button 1006. The casing or container 902 may be sized to fit within a hand H of a user, allowing the user to hold and aim the spectrometer at the sample material, and manipulate the user input with the same hand H to initiate measurement of the sample material. The casing or container 902 can house the different parts of the spectrometer such as the spectrometer module 160, illumination module 140, and sensor module 130. The spectrometer module may comprise a detector or sensor to measure the spectra of the sample material within a field of view 40 of the detector. The detector may be configured to have a wide field of view. The illumination module may comprise a light source configured to direct an optical beam 10 to the sample material S within the field of view 40. The light source may be configured to emit electromagnetic energy, comprising one or more of ultraviolet, visible, near infrared, or infrared light energy. The light source may comprise one or more component light sources. The illumination module may further comprise one or more optics coupled to the light source to direct the optical beam 10 toward the sample material S. The one or more optics may comprise one or more of a mirror, a beam splitter, a lens, a curved reflector, parabolic reflector, or parabolic concentrator, as described in further detail herein. The spectrometer 102 may further comprise a circuitry coupled to the detector and the light source, wherein the circuitry is configured to transmit the optical beam 10 in response to user interactions with the user input using hand H holding the spectrometer.

When a user initiates a measurement of a sample material S using the spectrometer 102, for example by pressing the operating button 1006 with hand H, the spectrometer emits an optical beam 10 toward the sample material within the field of view 40. When the optical beam 10 hits the sample material S, the light may be partially absorbed and/or partially reflected by the sample material; alternatively or in combination, optical beam 10 may cause the sample material to emit light in response. The detector of the spectrometer module 160 may be configured to sense at least a portion of the optical beam 10 reflected back by the sample and/or light emitted by the sample in response to the optical beam 10, and consequently generate the spectral data of the sample material as described in further detail herein.

The spectrometer 102 may be configured to begin measurement of a sample material S with just ambient light, without the optical beam 10. After completing the measurement with ambient light only, the illumination module 140 of the spectrometer 102 can generate the optical beam 10, and the spectrometer module 160 can begin measurement of the sample material with the optical beam 10. In this case, there may be a brief time lapse between the initiation of a measurement, for example by a user pressing the operating button 1006, and the generation of the optical beam 10 and the visible portions thereof. The ambient light-only measurement can be used to reduce or eliminate the contribution of ambient light in the spectral data of the sample material S. For example, the measurement made with ambient light only can be subtracted from the measurement made with the optical beam 10.

A portion of the optical beam 10 that is reflected from the sample material S may be visible to the user; this visible, reflected portion of optical beam 10 may define the measurement area 50 of the sample material S. The measurement area 50 of the sample may at least partially overlap with and fall within the field of view 40 of the detector of the spectrometer. The area covered by the field of view 40 may be larger than the visible area of the sample illuminated by the optical beam 10, or the measurement area 50 defined by the visible portion of the optical beam 10. Alternatively, the field of view may be smaller than the optical beam, for example. In many configurations, the field of view 40 of the detector of the spectrometer module is larger than the area illuminated by the optical beam 10, and hence the measurement area 50 is defined by the optical beam 10 rather than by the field of view 40 of the detector.

The visible portion of optical beam 10 may comprise one or more wavelengths corresponding to one or more colors visible to the user. For example, the visible portion of optical beam 10 may comprise one or more wavelengths corresponding to the colors red, orange, yellow, blue, green, indigo, violet, or a combination thereof. The visible portion of optical beam 10 reflected from the sample material S may comprise about 0.1% to about 10%, about 1% to about 4%, or about 2% to about 3% of optical beam 10. The visible portion of optical beam 10 may comprise light operating with power in a range from about 0.1 mW to about 100 mW, about 1 mW to about 75 mW, about 1 mW to about 50 mW, about 5 mW to about 40 mW, about 5 mW to about 30 mW, about 5 mW to about 20 mW, or about 10 mW to about 15 mW. The visible portion of optical beam 10 incident on the sample may have an intensity in a range from about 0.1 mW to about 100 mW, about 1 mW to about 75 mW, about 1 mW to about 50 mW, about 5 mW to about 40 mW, about 5 mW to about 30 mW, about 5 mW to about 20 mW, or about 10 mW to about 15 mW. The visible portion of optical beam 10 incident on the sample may have an intensity or total light output in a range from about 0.001 lumens to about 10 lumens, about 0.001 lumens to about 5 lumens, about 0.005 lumens to about 10 lumens, about 0.01 lumens to about 10 lumens, about 0.005 lumens to about 5 lumens, about 0.05 lumens to about 5 lumens, about 0.1 lumens to about 5 lumens, about 0.2 lumens to about 1 lumens, or about 0.5 lumens to about 5 lumens.

The optical beam 10 incident on the sample S may have an area of about 0.5 to about 2 $cm^2$, or about 1 $cm^2$. Accordingly, the optical beam 10 incident on the sample S may have an irradiance within a range from about 0.1 $mW/cm^2$ to about 100 $mW/cm^2$, about 1 $mW/cm^2$ to about 75 $mW/cm^2$, about 1 $mW/cm^2$ to about 50 $mW/cm^2$, about 5 $mW/cm^2$ to about 40 $mW/cm^2$, about 5 $mW/cm^2$ to about 30 $mW/cm^2$, about 5 $mW/cm^2$ to about 20 $mW/cm^2$, or about 10 $mW/cm^2$ to about 15 $mW/cm^2$. The optical beam 10 incident on the sample S may have an illuminance ($E_v$) within a range from about 20 lux (lumens/$m^2$) to about 100,000 lux, about 200 lux to about 75,000 lux, about 400 lux to about 50,000 lux, about 2,000 lux to about 25,000 lux, about 2,000 lux to about 15,000 lux, about 4,000 lux to about 15,000 lux, or about 4,000 lux to about 6,000 lux.

The light output of the visible portion of optical beam 10 may vary depending on the type of light source. In some cases, the visible light output of optical beam 10 may vary due to the different luminous efficacies of different types of light source. For example, blue light-emitting diode (LED) may have an efficacy of about 40 lumens/W, a red LED may have an efficacy of about 70 lumens/W, and a green LED may have an efficacy of about 90 lumens/W. Accordingly, the visible light output of optical beam 10 may vary depending on the color or wavelength range of the light source.

The light output of the visible portion of optical beam 10 may also vary due to the nature of interactions between the different components of a light source. For example, the light source may comprise a light source combined with an optical element configured to shift the wavelength of the light produced by the first light source, as described in further detail herein. In this embodiment, the visible light output of the visible portion of optical beam 10 may vary depending on the amount of the light produced by the light source that is configured to pass through the optical element without being absorbed or wavelength-shifted, as described in further detail herein.

As shown in FIG. 1, the optical beam 10 may comprise a visible aiming beam 20. The aiming beam 20 may comprise one or more wavelengths corresponding to one or more colors visible to the user, such as red, orange, yellow, blue, green, indigo, or violet. Alternatively or in combination, the optical beam 10 may comprise a measurement beam 30, configured to measure the spectra of the sample material. The measurement beam 30 may be visible, such that the measurement beam 30 comprises and functions as a visible aiming beam. The optical beam 10 may comprise a visible measurement beam 30 that comprises a visible aiming beam. The measurement beam 30 may comprise light in the visible spectrum, non-visible spectrum, or a combination thereof. The aiming beam 20 and the measurement beam 30 may be produced by the same light source or by different light sources within the illumination module 140, and can be arranged to illuminate the sample material S within the field of view 40 of the detector or sensor of the spectrometer 102. The visible aiming beam 20 and the optical beam 30 may be partially or completely overlapping, aligned, and/or coaxial.

The visible aiming beam 20 may comprise light in the visible spectrum, for example in a range from about 390 nm to about 800 nm, which the user can see reflected on a portion of the sample material S. The aiming beam 20 can provide basic visual verification that the spectrometer 102 is operational, and can provide visual indication to the user that a measurement is in progress. The aiming beam 20 can help the user visualize the area of the sample material being measured, and thereby provide guidance the user in adjusting the position and/or angle of the spectrometer 102 to position the measurement area 50 over the desired area of the sample material S. The aiming beam 20 may be configured with circuitry to be emitted throughout the duration of a measurement, and automatically turn off when the measurement of the sample material S is complete; in this case, the aiming beam 20 can also provide visual indication to the user of how long the user should hold the spectrometer 102 pointed at the sample material S.

The visible aiming beam 20 and the measurement beam 30 may be produced by the same light source, wherein the visible aiming beam 20 comprises a portion of the measurement beam 30. Alternatively, the aiming beam 20 may be produced by a first light source, and the measurement beam 30 may be produced by a second light source. For example, the measurement beam 30 may comprise an infrared beam and the aiming beam 20 may comprise a visible light beam.

The measurement beam 30 may be configured to illuminate the measurement area 50 of the sample S, and the aiming beam 20 may be configured to illuminate an area of the sample overlapping with the measurement area, thereby displaying the measurement area to the user. The visible area illuminated by the visible aiming beam 20 may comprise from about 50% to about 150% or about 75% to about 125% of the measurement area, or at least about 90%, at least about 95%, or at least about 99% of the measurement area.

One or more optics of the illumination module, such as a lens or a parabolic reflector, may be arranged to receive the aiming beam 20 and the measurement beam 30 and direct the aiming beam and measurement beam toward the sample material S, with the aiming beam and measurement beam overlapping on the sample. The aiming beam 20 may be arranged to be directed along an aiming beam axis 25, while the measurement beam 30 may be arranged to be directed along a measurement beam axis 35. The aiming beam axis 25 may be co-axial with measurement beam axis 35.

The sensor or detector of the spectrometer module 160 may comprise one or more filters configured to transmit the measurement beam 30 but inhibit transmission of the aiming beam 20. In many configurations, the spectrometer module comprises one filter configured to inhibit transmission of visible light, thereby inhibiting transmission of portions of the aiming beam 20 and measurement beam 30 reflected from the sample that comprise visible light. In some configurations, the spectrometer module 160 may comprise a plurality of optical filters configured to inhibit transmission of a portion of the aiming beam 20 reflected the sample material S, and to transmit a portion of the measurement beam 30 reflected from the sample. In configurations of the spectrometer module comprising a plurality of optical channels, the spectrometer module may comprise a plurality of filters wherein each optical filter corresponds to an optical channel. Each filter may be configured to inhibit transmission of light within a specific range and/or within a specific angle of incidence, wherein the filtered specific range or specific angle of incidence may be specific to the corresponding channel. In some configurations, each optical channel of the spectrometer module may comprise a field of view. The field of view 40 of the spectrometer module may comprise a plurality of overlapping fields of view of a plurality of optical channels. The aiming beam and the measurement beam may overlap with the plurality of overlapping fields of view on the sample S. In many configurations, a diffuser may be disposed between the plurality of optical filters and the incident light from the sample, in which each optical filter corresponds to an optical channel. In such configurations, the plurality of optical channels may comprise similar fields of view through the diffuser, with each field of view at least partially overlapping with the fields of view of other optical channels. With the diffuser, the spectrometer may comprise a wide field of view, for example ±90°.

Optionally, the visible aiming beam 20 may be produced by a light source separate from the illumination module 140. In this case, the separate light source may be configured to produce the aiming beam such that the aiming beam illuminates a portion of the sample material that overlaps with the measurement area 50 of the sample.

The compact size of the spectrometer 102 can provide a hand held device that can be directed (e.g., pointed) at a material to rapidly obtain information about the material. As shown in FIGS. 1A and 1B, the spectrometer 102 may have a size and weight such that the spectrometer can be held by a user with only one hand H. The spectrometer can have a size and weight such that the spectrometer can be portable. The spectrometer can have a weight of about 1 gram (g), 5 g, 10 g, 15 g, 20 g, 25 g, 30 g, 35 g, 40 g, 45 g, 50 g, 55 g, 60 g, 65 g, 70 g, 80 g. 85 g, 90 g, 95 g, 100 g, 110 g, 120 g, 130 g, 140 g, 150 g, 160 g, 170 g, 180 g, 190 g, or 200 g. The spectrometer can have a weight less than 1 g. The spectrometer can have a weight greater than 200 g. The spectrometer can have a weight that is between any of the two values given above. For example, the spectrometer can have a weight within a range from about 1 g to about 200 g, about 1 g to about 100 g, about 5 g to about 50 g, about 5 g to about 40 g, about 10 g to about 40 g, about 10 g to about 30 g, or about 20 g to about 30 g.

The spectrometer can have a total volume of at most about 200 cm³, 150 cm³, 100 cm³, 95 cm³, 90 cm³, 85 cm³, 80 cm³, 75 cm³, 70 cm³, 65 cm³, 60 cm³, 55 cm³, 50 cm³, 45 cm, 40 cm³, 35 cm³, 30 cm³, 25 cm³, 20 cm³, 15 cm³, 10 cm³, 5 cm³, or 1 cm³. The spectrometer can have a volume less than 1 cm³. The spectrometer can have a volume greater than 100 cm³. The spectrometer can have a volume that is between any of the two values given above. For example, the spectrometer may have a volume within a range from about 1 cm³ to about 200 cm³, about 40 cm³ to about 200 cm³, about 60 cm³ to about 150 cm³, about 80 cm³ to about 120 cm³, about 80 cm³ to about 100 cm³, or about 90 cm³.

The spectrometer shape can comprise a rectangular prism, cylinder, or other three-dimensional shape. The spectrometer can have a length of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a length less than 5 mm. The spectrometer can have a length greater than 500 mm. The spectrometer can have a length that is between any of the two values given above. For example, the spectrometer have a length within a range from about 10 mm to about 100 mm, about 25 mm to about 75 mm, or about 50 mm to about 70 mm. The spectrometer can have a width of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a width less than 5 mm. The spectrometer can have a width greater than 500 mm. The spectrometer can have a width that is between any of the two values given above. For example, the spectrometer may have a width within a range from about 10 mm to about 75 mm, about 20 mm to about 60 mm, or about 30 mm to about 50 mm. The spectrometer can have a height of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a height less than 5 mm. The spectrometer can have a height greater than 500 mm. The spectrometer can have a height that is between any of the two values given above. For example, the spectrometer may have a height within a range from about 1 mm to about 50 mm, about 5 mm to about 40 mm, or about 10 mm to about 20 mm. The spectrometer may, for example, have dimensions within a range from about 0.1 cm×0.1 cm×2 cm to about 5 cm×5 cm×10 cm. In the case of a cylindrical spectrometer the spectrometer can have a radius of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a radius less than 5 mm. The spectrometer can have a radius greater than 500 mm. The spectrometer can have a radius that is between any of the two values given above.

One or more of the components of the spectrometer can be powered by a battery. The battery can be on-board the spectrometer. The battery can have a weight of at most about 50 g, 45 g, 40 g, 35 g, 30 g, 25 g, 20 g, 15 g, 10 g, 5 g, 1 g, or 0.1 g. The battery can have a weight less than 0.1 g. The battery can have a weight greater than 50 g. The battery can have a weight that is between any of the two values given above. For example, the batter may have a weight that is within a range from about 2 g to about 6 g, about 3 g to about 5 g, or about 4 g.

The compact spectrometer 102 may have an optical resolution of less than 10 nm, less than 5 nm, less than 4 nm, less than 3 nm, less than 2 nm, less than 1 nm, less than 0.5 nm, or less than 0.1 nm. The spectrometer can have an optical resolution that is between any of the two values given above. For example, the spectrometer may have an optical resolution that is within a range from about 0.1 nm to about 100 nm, about 1 nm to about 50 nm, about 1 nm to about 10 nm, or about 2 nm to about 5 nm. The spectrometer may have an optical resolution of approximately 5 nm, which is equivalent to approximately 100 cm$^{-1}$ at a wavelength of about 700 nm and equivalent to approximately 40 cm$^{-1}$ at a wavelength of about 1100 nm. The spectrometer may have an optical resolution that is between 100 cm$^{-1}$ and 40 cm$^{-1}$. The spectrometer can have a temporal signal-to-noise ratio (SNR) of about 1000 for a single sensor reading (without averaging, at maximum spectral resolution) for a wavelength of about 1000 nm, or an SNR of about 2500 for a wavelength of about 850 nm. The compact spectrometer, when configured to perform algorithmic processing or correction of measured spectral data, may be able to detect changes in normalized signals in the order of about $1\times10^{-3}$ to about $1\times10^{-4}$, or about $5\times10^{-4}$. The light source of the illumination module may be configured to have a stabilization time of less than 1 min, less than 1 s, less than 1 ms, or about 0 s.

Spectrometer Using Secondary Emission Illumination with Filter-Based Optics

Figure 4:
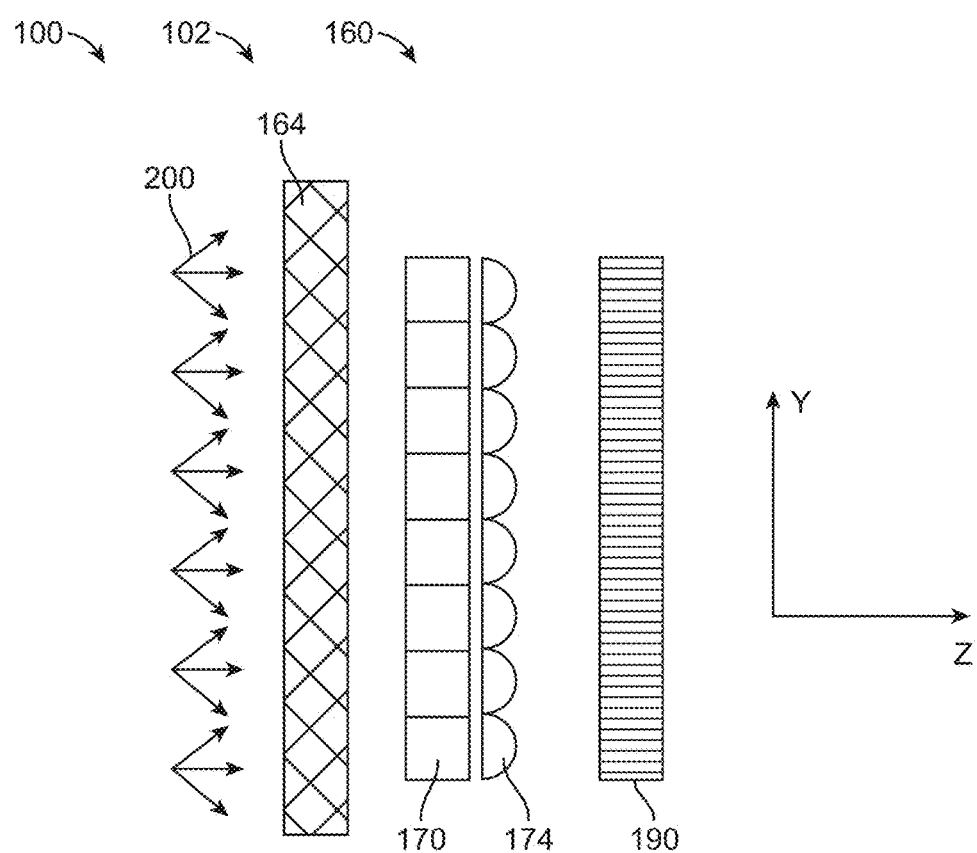
FIG. 4 shows a schematic diagram of an optical layout in accordance with configurations.

Reference is now made to FIG. 4, which illustrates non-limiting configurations of the compact spectrometer system 100 herein disclosed. The system comprises a spectrometer 102, which comprises various modules such as a spectrometer module 160. As illustrated, the spectrometer module 160 may comprise a diffuser 164, a filter matrix 170, a lens array 174 and a detector 190.

The spectrometer system may comprise a plurality of optical filters of filter matrix 170. The optical filter can be of any type known in the art. Non-limiting examples of suitable optical filters include Fabry-Perot (FP) resonators, cascaded FP resonators, and interference filters. For example, a narrow bandpass filter (≤10 nm) with a wide blocking range outside of the transmission band (at least 200 nm) can be used. The center wavelength (CWL) of the filter can vary with the incident angle of the light impinging upon it.

The central wavelength of the central band can vary by 10 nm or more, such that the effective range of wavelengths passed with the filter is greater than the bandwidth of the filter. In many instances, the central wavelength varies by an amount greater than the bandwidth of the filter. For example, the bandpass filter can have a bandwidth of no more than 10 nm and the wavelength of the central band can vary by more than 10 nm across the field of view of the sensor.

The spectrometer system may comprise a filter matrix. The filter matrix can comprise one or more filters, for example a plurality of filters. The use of a single filter can limit the spectral range available to the spectrometer. A filter can be an element that only permits transmission of a light signal with a predetermined incident angle, polarization, wavelength, and/or other property. For example, if the angle of incidence of light is larger than 30°, the system may not produce a signal of sufficient intensity due to lens aberrations and the decrease in the efficiency of the detector at large angles. For an angular range of 30° and an optical filter center wavelength (CWL) of ~850 nm, the spectral range available to the spectrometer can be about 35 nm, for example. As this range can be insufficient for some spectroscopy based applications, configurations with larger spectral ranges may comprise an optical filter matrix composed of a plurality of sub-filters. Each sub-filter can have a different CWL and thus covers a different part of the optical spectrum. The sub-filters can be configured in one or more of many ways and be tiled in two dimensions, for example.

Depending on the number of sub-filters, the wavelength range accessible to the spectrometer can reach hundreds of nanometers. In configurations comprising a plurality of sub-filters, the approximate Fourier transforms formed at the image plane (i.e. one per sub-filter) overlap, and the signal obtained at any particular pixel of the detector can result from a mixture of the different Fourier transforms.

The filter matrixes may be arranged in a specific order to inhibit cross talk on the detector of light emerging from different filters and to minimize the effect of stray light. For example, if the matrix is composed of 3×4 filters then there are 2 filters located at the interior of the matrix and 10 filters at the periphery of the matrix. The 2 filters at the interior can be selected to be those at the edges of the wavelength range. Without being bound by a particular theory, the selected inner filters may experience the most spatial cross-talk but be the least sensitive to cross-talk spectrally.

The spectrometer module may comprise a lens array 174. The lens array can comprise a plurality of lenses. The number of lenses in the plurality of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

The spectrometer system may comprise a detector 190, which may comprise an array of sensors. In many cases, the detector is capable of detecting light in the wavelength range of interest. The compact spectrometer system disclosed herein can be used from the UV to the IR, depending on the nature of the spectrum being obtained and the particular spectral properties of the sample being tested. The detector can be sensitive to one or more of ultraviolet wavelengths of light, visible wavelengths of light, or infrared wavelengths of light. In some cases, a detector that is capable of measuring intensity as a function of position (e.g. an array detector or a two-dimensional image sensor) is used.

In some instances the spectrometer does not comprise a cylindrical beam volume hologram (CVBH).

The detector can be located in a predetermined plane. The predetermined plane can be the focal plane of the lens array. Light of different wavelengths (X1, X2, X3, X4, etc.) can arrive at the detector as a series of substantially concentric circles of different radii proportional to the wavelength. The relationship between the wavelength and the radius of the corresponding circle may not be linear.

The detector may receive non-continuous spectra, for example spectra that can be unlike a dispersive element would create. The non-continuous spectra can be missing parts of the spectrum. The non-continuous spectrum can have the wavelengths of the spectra at least in part spatially out of order, for example. In some cases, first short wavelengths contact the detector near longer wavelengths, and second short wavelengths contact the detector at distances further away from the first short wavelengths than the longer wavelengths.

The detector may comprise a plurality of detector elements, such as pixels for example. Each detector element may be configured so as to receive signals of a broad spectral range. The spectral range received on a first and second pluralities of detector elements may extend at least from about 10 nm to about 400 nm. In many instances, spectral range received on the first and second pluralities of detector elements may extend at least from about 10 nm to about 700 nm. In many instances, spectral range received on the first and second pluralities of detector elements may extend at least from about 10 nm to about 1600 nm. In many instances, spectral range received on the first and second pluralities of detector elements may extend at least from about 400 nm to about 1600 nm. In many instances, spectral range received on the first and second pluralities of detector elements may extend at least from about 700 nm to about 1600 nm.

The spectrometer system may comprise a diffuser. In configurations in which the light emanating from the sample is not sufficiently diffuse, a diffuser can be placed in front of other elements of the spectrometer. The diffuser can be placed in a light path between a light emission and a detector and/or filter. Collimated (or partially collimated light) can impinge on the diffuser, which then produces diffuse light which then impinges on other aspects of the spectrometer, e.g. an optical filter.

In many cases, the lens array, the filter matrix, and the detector are not centered on a common optical axis. In many cases, the lens array, the filter matrix, and the detector are aligned on a common optical axis.

The principle of operation of compact spectrometer may comprise one or more of the following attributes. Light impinges upon the diffuser and at least a fraction of the light is transmitted through the diffuser. The light next impinges upon the filter matrix at a wide range of propagation angles and the spectrum of light passing through the sub-filters is angularly encoded. The angularly encoded light then passes through the lens array (e.g. Fourier transform focusing elements) which performs (approximately) a spatial Fourier transform of the angle-encoded light, transforming it into a spatially-encoded spectrum. Finally the light reaches the detector. The location of the detector element relative to the optical axis of a lens of the array corresponds to the wavelength of light, and the wavelength of light at a pixel location can be determined based on the location of the pixel relative to the optical axis of the lens of the array. The intensity of light recorded by the detector element such as a pixel as a function of position (e.g. pixel number or coordinate reference location) on the sensor corresponds to the resolved wavelengths of the light for that position.

In some cases, an additional filter is placed in front of the compact spectrometer system in order to block light outside of the spectral range of interest (i.e. to prevent unwanted light from reaching the detector).

In configurations in which the spectral range covered by the optical filters is insufficient, additional sub-filters with differing CWLs can be used.

In some instances, shutters allow for the inclusion or exclusion of light from part of the spectrometer 102. For example, shutters can be used to exclude particular sub-filters. Shutters may also be used to exclude individual lens.

Figure 5:
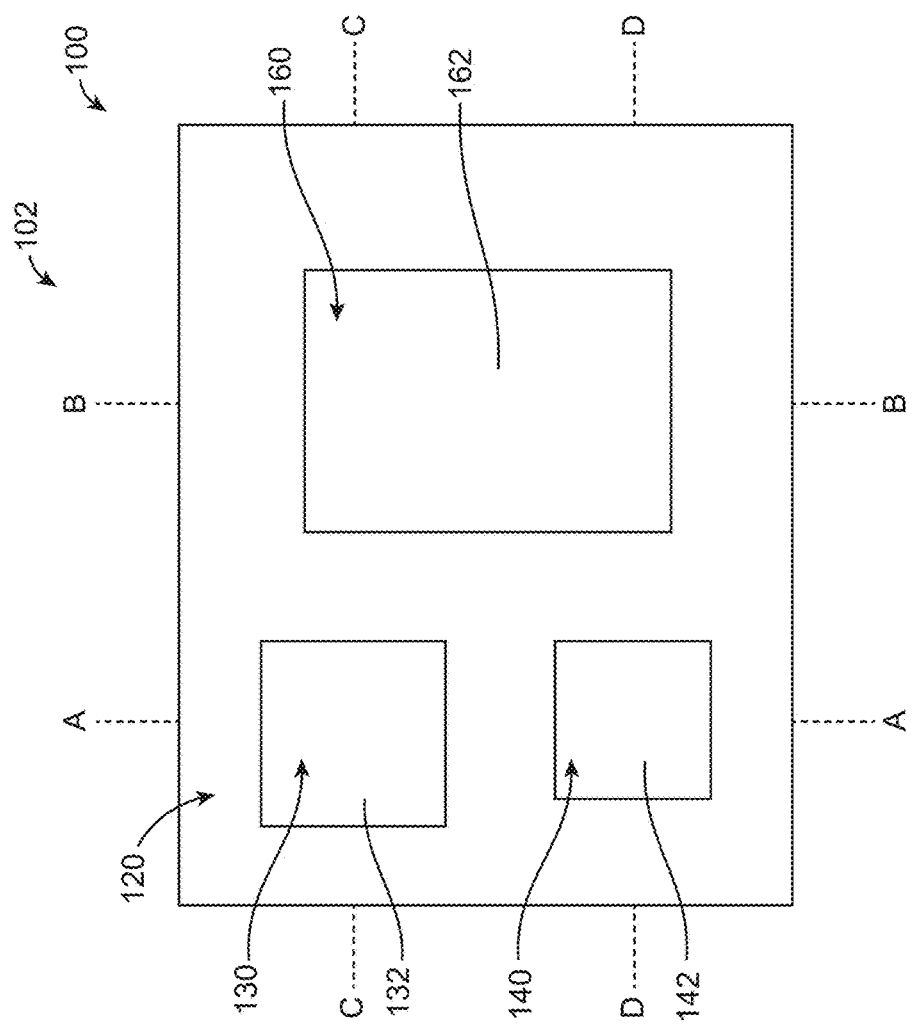
FIG. 5 shows a schematic diagram of a spectrometer head, in accordance with configurations.

FIG. 5 shows a schematic diagram of spectrometer head in accordance with configurations. In many cases, the spectrometer 102 comprises a spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a sensor window 132, and the illumination module 140 can comprise an illumination window 142.

The illumination module and the spectrometer module may be configured to have overlapping fields of view at the sample. The overlapping fields of view can be provided in one or more of many ways. For example, the optical axes of the illumination source, the temperature sensor and the matrix array can extend in a substantially parallel configuration. Alternatively, one or more of the optical axes can be oriented toward another optical axis of another module.

Figure 6:
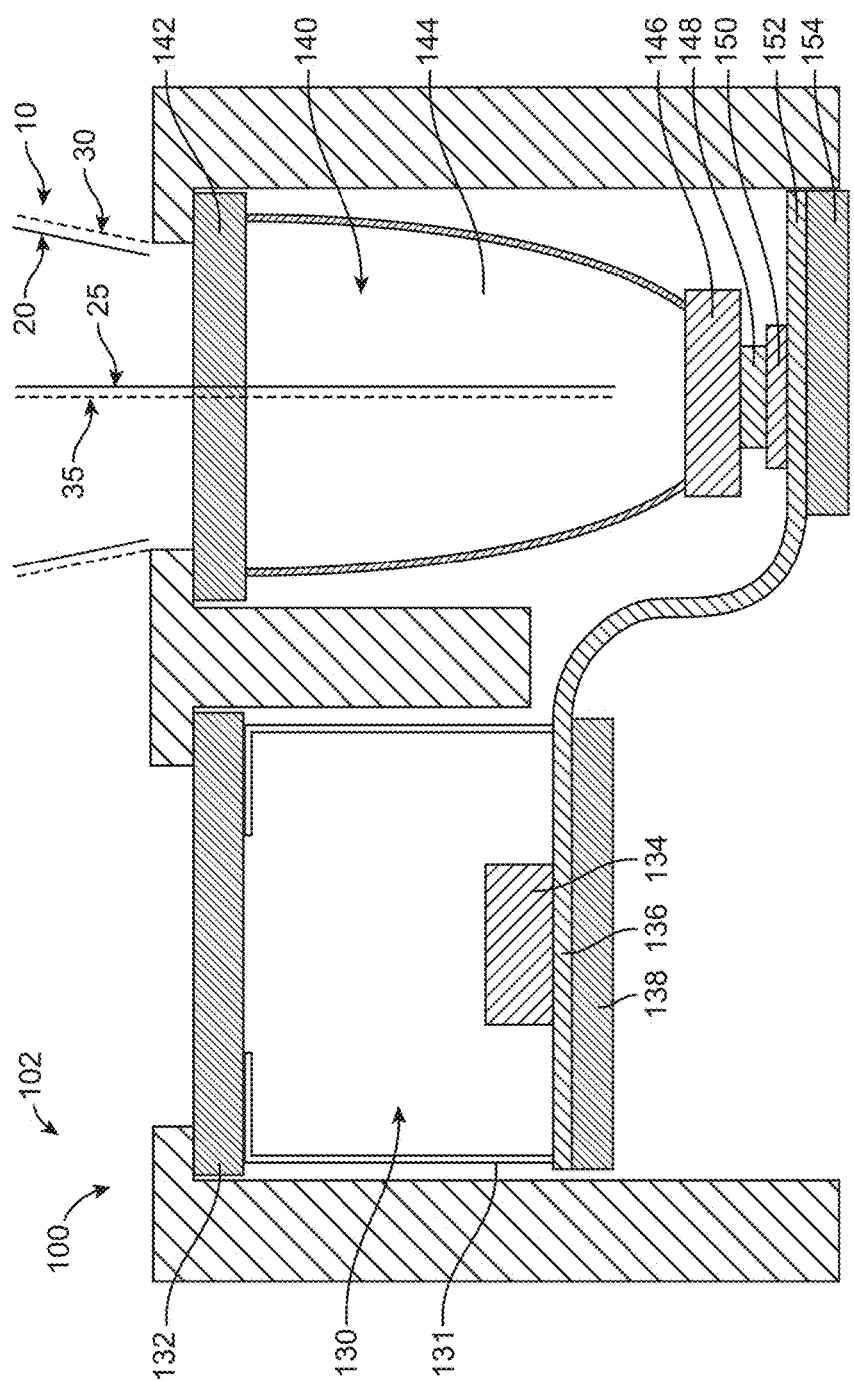
FIG. 6 shows a schematic drawing of cross-section A of the spectrometer head of FIG. 5, in accordance with configurations.

FIG. 6 shows a schematic drawing of cross-section A of the spectrometer head of FIG. 3, in accordance with configurations. In order to lessen the noise and/or spectral shift produced from fluctuations in temperature, a spectrometer head 120 comprising a temperature sensor module 130 can be used to measure and record the temperature during the measurement. The temperature sensor element can measure the temperature of the sample in response to infrared radiation emitted from the sample, and transmit the temperature measurement to a processor. Accurate and/or precise temperature measurement can be used to standardize or modify the spectrum produced. For example, different spectra of a given sample can be measured based on the temperature at which the spectrum was taken. A spectrum can be stored with metadata relating to the temperature at which the spectrum was measure. The temperature sensor module 130 may comprise a temperature sensor window 132. The temperature sensor window can seal the sensor module. The temperature sensor window 132 can be made of material that is substantially non-transmissive to visible light and transmits light in the infrared spectrum. The temperature sensor window 132 may comprise germanium, for example. The temperature sensor window can be about 0.2, 0.3, 0.4, 0.5, 0.6, 0.7, 0.8, 0.9 or 1.0 mm thick.

The temperature sensor can comprise a field of view (herein after "FoV") limiter. In many instances, the temperature sensor has a field of view oriented to overlap with a field of view of the detector and a field of view of an illuminator. For example, the field of view can be limited by an aperture formed in a material supporting the window 132 of temperature sensor module and the dimensions of the temperature sensor 134. In some instances, the temperature sensor module has a limited field of view and comprises a heat conductive metal cage disposed on a flex printed circuit board (PCB) 136. The PCB 136 can be mounted on a stiffener 138 in order to inhibit movement relative to the other modules on the sensor head. The flexible circuit board may be backed by stiffener 138 comprising a metal. The temperature sensor 134 can be a remote temperature sensor. The temperature sensor can give a temperature that is accurate to within about 5, 4, 3, 2, 1, 0.7, 0.4, 0.3, 0.2 or 0.1 degree Celsius of the ambient temperature of the sample. The temperature sensor may measure the ambient temperature with precision to 3, 2, 1, 0.5, or 0.1 degree Celsius.

The spectrometer head may comprise an illumination module 140. The illumination module can illuminate a sample with light. In some instances, the illumination module comprises an illumination window 142. The illumination window can seal the illumination module. The illumination window can be substantially transmissive to the light produced in the illumination module. For example, the illumination window can comprise glass. The illumination module can comprise a light source 148. The light source can comprise one or more light emitting diodes (LED). For example, the light source may comprise a blue LED, red LED, green LED, infrared LED, or a combination thereof.

The light source 148 can be mounted on a mounting fixture 150. The mounting fixture may comprise a ceramic package. For example, the light fixture can be a flip-chip LED die mounted on a ceramic package. The mounting fixture 150 can be attached to a flexible printed circuit board (PCB) 152 which can optionally be mounted on a stiffener 154 to reduce movement of the illumination module. The flex PCB of the illumination module and the PCT of temperature sensor modules may comprise different portions of the same flex PCB, which may also comprise portions of spectrometer PCB.

The wavelength of the light produced by the light source 148 can be shifted by a plate 146. Plate 146 can be a wavelength shifting plate. Plate 146 may comprise phosphor embedded in glass. Alternatively or in combination, plate 146 can comprise a nano-crystal, a quantum dot, or combinations thereof. The plate can absorb light from the light source and release light having a frequency lower than the frequency of the absorbed light. In some cases, a light source produces visible light, and plate 146 absorbs the light and emits near infrared light. The light source may be in close proximity to or directly touching the plate 146. The light source and associated packaging may be separated from the plate by a gap to limit heat transfer. For example, the gap between the light source and the plate can be at least 0.1, 0.2, 0.3, 0.4, 0.5, 0.6, 0.7, 0.8, 0.9, 1.0, 1.5, 2.0, 2.5, 3.0, 3.5, 4.0, 5.0, 6.0, 7.0, 8.0, 9.0, or 10.0 mm. Alternatively, the light source packaging may touch the plate 146 in order to conduct heat from the plate such that the light source packaging comprises a heat sink.

The illumination module can further comprise a light concentrator such as a parabolic concentrator 144 or a condenser lens in order to concentrate the light. The parabolic concentrator 144 may be a reflector. The parabolic concentrator 144 may comprise stainless steel or gold-plated stainless steel. The concentrator can concentrate light to a cone. For example, the light can be concentrated to a cone with a field of view of about 30-45, 25-50, or 20-55 degrees.

The illumination module may be configured to transmit light and the spectrometer module may be configured to receive light along optical paths extending substantially perpendicular to an entrance face of the spectrometer head. The modules can be configured such that light can be transmitted from one module to an object (such as a sample S) and reflected or scattered to another module which receives the light.

The optical axes of the illumination module and the spectrometer module may be configured to be non-parallel such that the optical axis representing the spectrometer module is at an offset angle to the optical axis of the illumination module. This non-parallel configuration can be provided in one or more of many ways. For example, one or more components can be supported on a common support and offset in relation to an optic such as a lens in order to orient one or more optical axes toward each other. Alternatively or in combination, a module can be angularly inclined with respect to another module. The optical axis of each module may be aligned at an offset angle of greater than 1, 2, 3, 4, 5, 6, 7, 8, 9, 10, 12, 14, 16, 18, 20, 25, 30, 35, 40, 45, or 50 degrees. The illumination module and the spectrometer module may be configured to be aligned at an offset angle of less than 1, 2, 3, 4, 5, 6, 7, 8, 9, 10, 12, 14, 16, 18, 20, 25, 30, 35, 40, 45, or 50 degrees. The illumination module and the spectrometer module can be configured to be aligned at an offset angle between than 1-10, 11-20, 21-30, 31-40 or 41-50 degrees. The offset angle of the modules may be set firmly and not adjustable, or the offset angle may adjustable. The offset angle of the modules may be automatically selected based on the distance of the spectrometer head from the sample. Two modules may have parallel optical axes. Two or more modules may have offset optical axes. In some instances, the modules can have optical axes offset such that they converge on a sample. The modules can have optical axes offset such that they converge at a set distance. For example, the modules can have optical axes offset such that they converge at a distance of about 10, 20, 30, 40, 50, 60, 70, 80, 90, 100, 150, 200, 250, 300, 350, 400, or 500 mm away.

Figure 7:
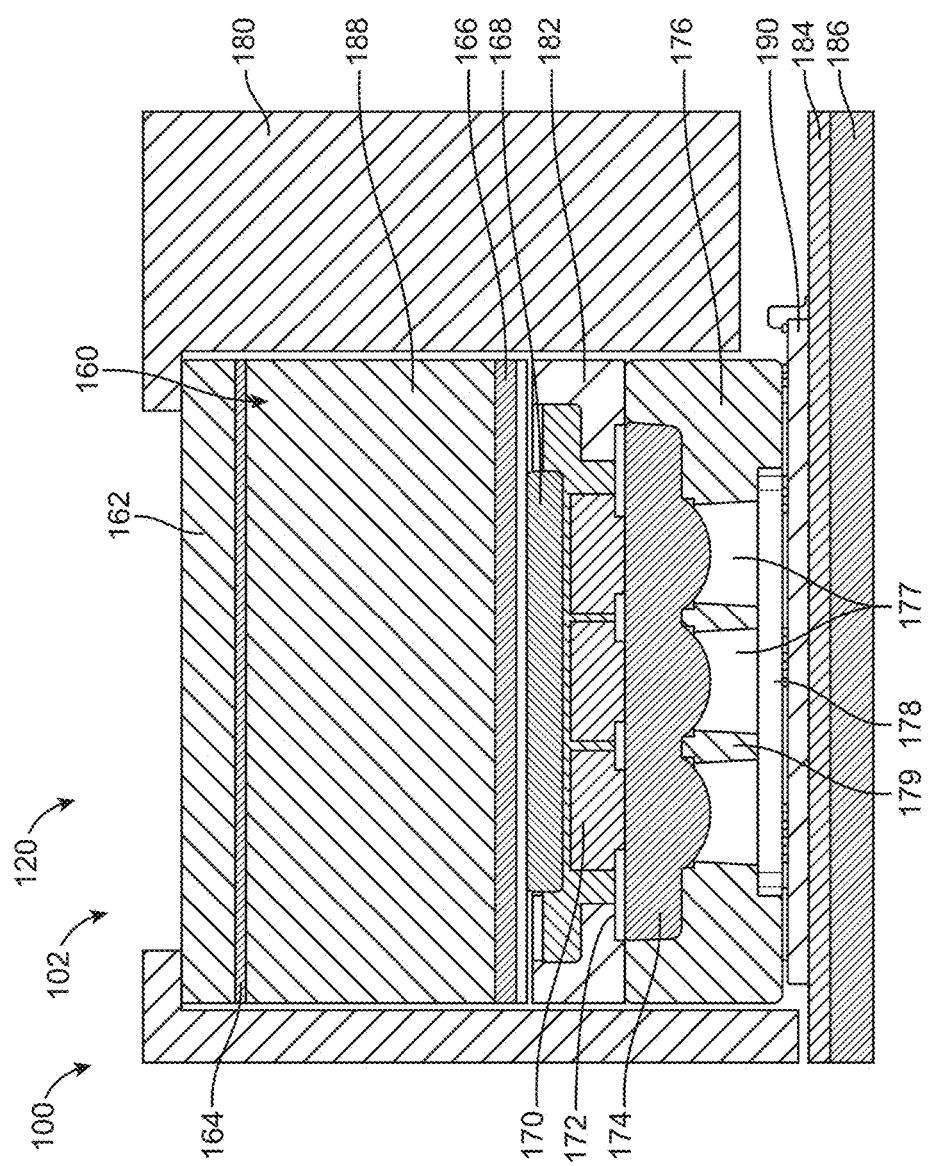
FIG. 7 shows a schematic drawing of cross-section B of the spectrometer head of FIG. 5, in accordance with configurations.

FIG. 7 shows a schematic drawing of cross-section B of the spectrometer head of FIGS. 3 and 4, in accordance with configurations. The spectrometer head 120 may comprise spectrometer module 160. The spectrometer module can be sealed by a spectrometer window 162. The spectrometer window 162 may be selectively transmissive to light with respect to the wavelength in order to analyze the spectral sample. For example, spectrometer window 162 can be an IR-pass filter. In some instances, the window 162 can be glass. The spectrometer module can comprise one or more diffusers. For example, the spectrometer module can comprise a first diffuser 164 disposed below the spectrometer window 162. The first diffuser 164 can distribute the incoming light. For example, the first diffuser can be a cosine diffuser. Optionally, the spectrometer module may comprise a light filter 188. Light filter 188 can be a thick IR-pass filter. For example, filter 188 can absorb light below a threshold wavelength. Filter 188 can absorb light with a wavelength below about 1000, 950, 900, 850, 800, 750, 700, 650, or 600 nm. The spectrometer module may further comprise a second diffuser 166. The second diffuser can generate Lambertian light distribution at the input of the filter matrix 170. The filter assembly can be sealed by a glass plate 168. Alternatively or in combination, the filter assembly can be further supported by a filter frame 182, which can attach the filter assembly to the spectrometer housing 180. The spectrometer housing 180 can hold the spectrometer window 162 in place and further provide mechanical stability to the module.

The first filter and the second filter can be arranged in one or more of many ways to provide a substantially uniform light distribution to the filters. The substantially uniform light distribution can be uniform with respect to an average energy to within about 25%, for example to within about 10%, for example. The first diffuser may distribute the incident light energy spatially on the second diffuser with a substantially uniform energy distribution profile. The first diffuser may make the light substantially homogenous with respect to angular distribution. The second diffuser can further diffuse the light energy of the substantially uniform energy distribution profile to a substantially uniform angular distribution profile, such that the light transmitted to each filter can be substantially homogenous both with respect to the spatial distribution profile and the angular distribution profile of the light energy incident on each filter. For example, the angular distribution profile of light energy onto each filter can be uniform to within about +/−25%, for example substantially uniform to within about +/−10%.

The spectrometer module comprises a filter matrix 170. The filter matrix can comprise one or more filters. In many instances, the filter matrix comprises a plurality of filters.

In some instances, each filter of the filter matrix 170 is configured to transmit a range of wavelengths distributed about a central wavelength. The range of wavelengths can be defined as a full width half maximum (hereinafter "FWHM") of the distribution of transmitted wavelengths for a light beam transmitted substantially normal to the surface of the filter as will be understood by a person of ordinary skill in the art. A wavelength range can be defined by a central wavelength and by a spectral width. The central wavelength can be the mean wavelength of light transmitted through the filter, and the band spectral width of a filter can be the difference between the maximum and the minimum wavelength of light transmitted through the filter. Each filter of the plurality of filters may be configured to transmit a range of wavelengths different from other filters of the plurality. The range of wavelengths overlaps with ranges of said other filters of the plurality and wherein said each filter comprises a central wavelength different from said other filters of the plurality.

The filter array comprises a substrate having a thickness and a first side and a second side, the first side oriented toward the diffuser, the second side oriented toward the lens array. In some instances, each filter of the filter array comprises a substrate having a thickness and a first side and a second side, the first side oriented toward the diffuser, the second side oriented toward the lens array. The filter array can comprise one or more coatings on the first side, on the second side, or a combination thereof. Each filter of the filter array can comprise one or more coatings on the first side, on the second side, or a combination thereof. In some instances, each filter of the filter array comprises one or more coatings on the second side, oriented toward the lens array. In some instances, each filter of the filter array comprises one or more coatings on the second side, oriented toward the lens array and on the first side, oriented toward the diffuser. The one or more coatings on the second side can be an optical filter. For example, the one or more coatings can permit a wavelength range to selectively pass through the filter. Alternatively or in combination, the one or more coatings can be used to inhibit cross-talk among lenses of the array. In some instances, the plurality of coatings on the second side comprises a plurality of interference filters, said each of the plurality of interference filters on the second side configured to transmit a central wavelength of light to one lens of the plurality of lenses. In some instances, the filter array comprises one or more coatings on the first side of the filter array. The one or more coatings on the first side of the array can comprise a coating to balance mechanical stress. In some instances, the one or more coatings on the first side of the filter array comprises an optical filter. For example, the optical filter on the first side of the filter array can comprise an IR pass filter to selectively pass infrared light. In many instances, the first side does not comprise a bandpass interference filter coating. In some instances, the first does not comprise a coating.

In many instances, the array of filters comprises a plurality of bandpass interference filters on the second side of the array. The placement of the fine frequency resolving filters on the second side oriented toward the lens array and apertures can inhibit cross-talk among the filters and related noise among the filters. In many instances, the array of filters comprises a plurality of bandpass interference filters on the second side of the array, and does not comprise a bandpass interference filter on the first side of the array.

In many instances, each filter defines an optical channel of the spectrometer. The optical channel can extend from the filter through an aperture and a lens of the array to a region of the sensor array. The plurality of parallel optical channels can provide increased resolution with decreased optical path length.

The spectrometer module can comprise an aperture array 172. The aperture array can prevent cross talk between the filters. The aperture array comprises a plurality of apertures formed in a non-optically transmissive material. In some instances, the plurality of apertures is dimensioned to define a clear lens aperture of each lens of the array, wherein the clear lens aperture of each lens is limited to one filter of the array. In some instances, the clear lens aperture of each lens is limited to one filter of the array.

In many instances the spectrometer module comprises a lens array 174. The lens array can comprise a plurality of lenses. The number of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

In many instances, each lens of the lens array comprises one or more aspheric surfaces, such that each lens of the lens array comprises an aspherical lens. In many instances, each lens of the lens array comprises two aspheric surfaces. Alternatively or in combination, one or more individual lens of the lens array can have two curved optical surfaces wherein both optical surfaces are substantially convex. Alternatively or in combination, the lenses of the lens array may comprise one or more diffractive optical surfaces.

In many instances, the spectrometer module comprises a support array 176. The support array 176 comprises a plurality of channels 177 defined with a plurality of support structures 179 such as interconnecting annuli. The plurality of channels 177 may define optical channels of the spectrometer. The support structures 179 can comprises stiffness to add rigidity to the support array 176. The support array may comprise a stopper to limit movement and fix the position the lens array in relation to the sensor array. The support array 176 can be configured to support the lens array 174 and fix the distance from the lens array to the sensor array in order to fix the distance between the lens array and the sensor array at the focal length of the lenses of the lens array. In many instances, the lenses of the array comprise substantially the same focal length such that the lens array and the sensor array are arranged in a substantially parallel configuration.

The support array 176 can extend between the lens array 174 and the stopper mounting 178. The support array 176 can serve one or more purposes, such as 1) providing the correct separation distance between each lens of lens array 170 and each region of the plurality of regions of the image sensor 190, and/or 2) preventing stray light from entering or exiting each channel, for example. In some instances, the height of each support in support array 176 is calibrated to the focal length of the lens within lens array 174 that it supports. In some instances, the support array 176 is constructed from a material that does not permit light to pass such as substantially opaque plastic. In some instances, support array 176 is black, or comprises a black coating to further reduce cross talk between channels. The spectrometer module can further comprise a stopper mounting 178 to support the support array. In many instances, the support array comprises an absorbing and/or diffusive material to reduce stray light, for example.

In many instances, the support array 176 comprises a plurality of channels having the optical channels of the filters and lenses extending therethrough. In some instances, the support array comprise a single piece of material extending from the lens array to the detector (i.e. CCD or CMOS array).

The lens array can be directly attached to the aperture array 172, or can be separated by an air gap of at least 1, 2, 3, 4, 5, 6, 7, 8, 9, 10, 12, 14, 16, 18, 20, 30, 40, or 50 micrometers. The lens array can be directly on top of the support array 178. Alternatively or in combination, the lens array can be positioned such that each lens is substantially aligned with a single support stopper or a single optical isolator in order to isolate the optical channels and inhibit cross-talk. In some instances, the lens array is positioned to be at a distance approximately equal to the focal length of the lens away from the image sensor, such that light coming from each lens is substantially focused on the image sensor.

In some instances, the spectrometer module comprises an image sensor 190. The image sensor can be a light detector. For example, the image sensor can be a CCD or 2D CMOS or other sensor, for example. The detector can comprise a plurality of regions, each region of said plurality of regions comprising multiple sensors. For example, a detector can be made up of multiple regions, wherein each region is a set of pixels of a 2D CMOS. The detector, or image sensor 190, can be positioned such that each region of the plurality of regions is directly beneath a different channel of support array 176. In many instances, an isolated light path is established from a single of filter of filter array 170 to a single aperture of aperture array 172 to a single lens of lens array 174 to a single stopper channel of support array 176 to a single region of the plurality of regions of image sensor 190. Similarly, a parallel light path can be established for each filter of the filter array 170, such that there are an equal number of parallel (non-intersecting) light paths as there are filters in filter array 170.

The image sensor 190 can be mounted on a flexible printed circuit board (PCB) 184. The PCB 184 can be attached to a stiffener 186. In some instances, the stiffener comprises a metal stiffener to prevent motion of the spectrometer module relative to the spectrometer head 120.

Figure 8:
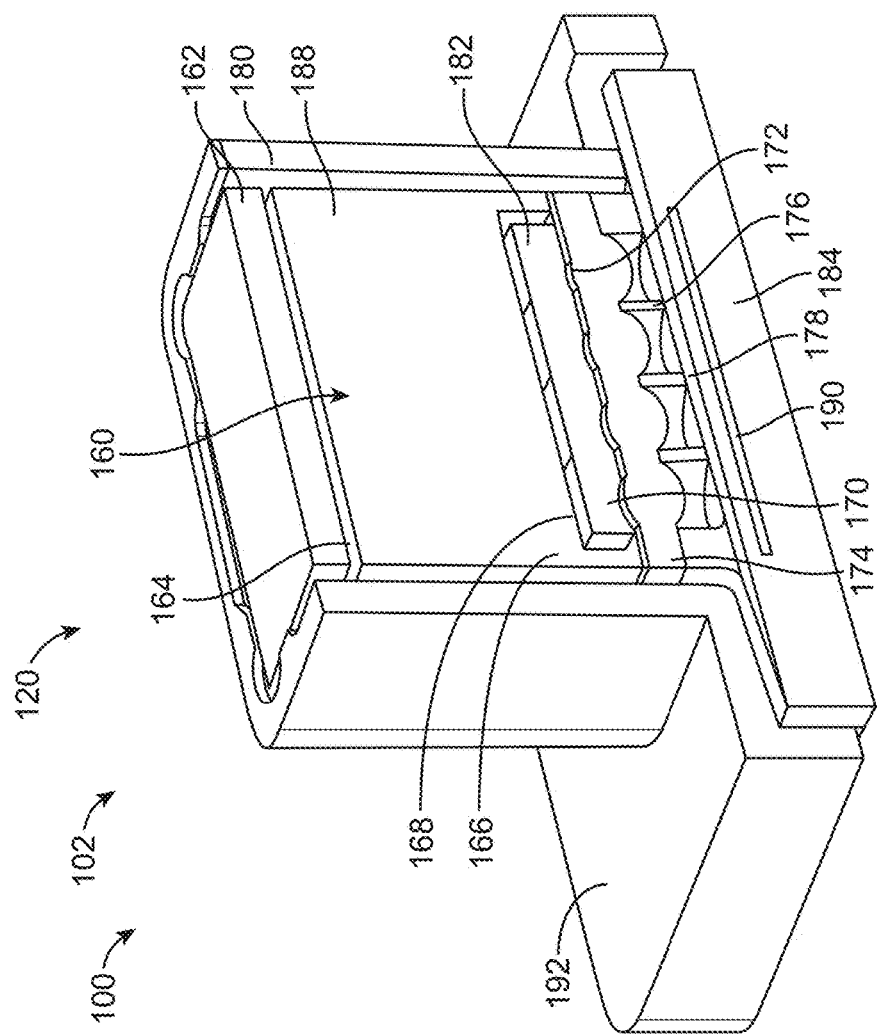
FIG. 8 shows an isometric view of a spectrometer module in accordance with configurations.

FIG. 8 shows an isometric view of a spectrometer module 160 in accordance with configurations. The spectrometer module 160 comprises many components as described herein. In many instances, the support array 176 can be positioned on a package on top of the sensor. In many instances, the support array can be positioned over the top of the bare die of the sensor array such that an air gap is present. The air gap can be less than 10, 9, 8, 7, 6, 5, 4, 3, 2 or 1 micrometer(s).

Figure 9:
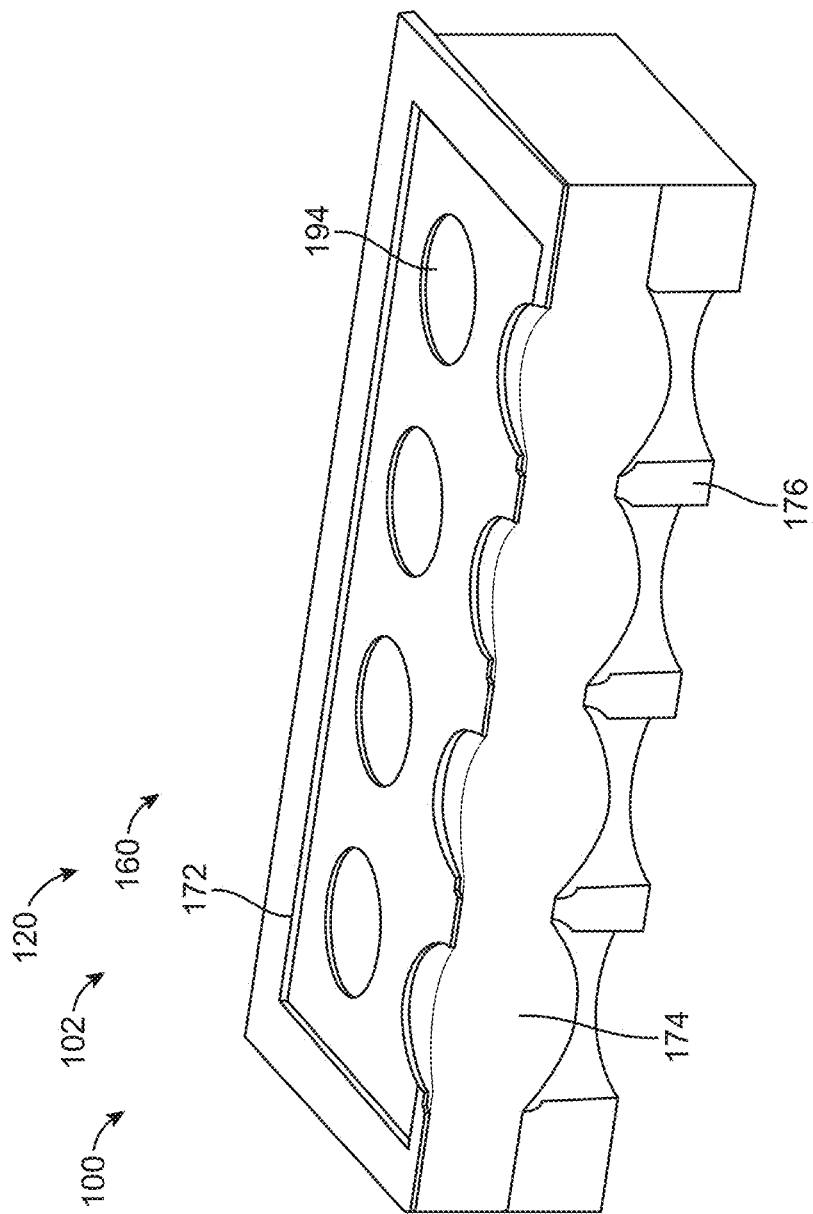
FIG. 9 shows the lens array within the spectrometer module, in accordance with configurations.

FIG. 9 shows the lens array 174 within the spectrometer module 160, in accordance with configurations. This isometric view shows the apertures 194 formed in a non-transmissive material of the aperture array 172 in accordance with configurations. In many instances, each channel of the support array 176 is aligned with a filter of the filter array 170, a lens of the lens array 174, and an aperture 194 of the aperture array in order to form a plurality of light paths with inhibited cross talk.

The glass-embedded phosphor of plate 146 may be a near-infrared (NIR) phosphor, capable of emitting infrared or NIR radiation in the range from about 700 nm to about 1100 nm.

The light filter 188 may be configured to block at least a portion of visible radiation included in the incident light.

In some cases, the first wavelength range of the first filter and the second wavelength range of the second filter fall within a wavelength range of about 400 nm to about 1100 nm. In some instances, the second wavelength range overlaps the first wavelength range by at least 2% of the second wavelength range. In some instances, the second wavelength range overlaps the first wavelength range by an amount of about 1% to about 5% of the second wavelength range. The overlap in the range of wavelengths of the filters may be configured to provide algorithmic correction of the gains across different channels, for example across the outputs of a first filter element and a second filter element.

The coating of the filter array and/or the support array may comprise a black coating configured to absorb most of the light that hits the coated surface. For example, the coating may comprise a coating commercially available from Anoplate (as described on http://www.anoplate.com/capabilities/anoblack_ni.html), Acktar (as described on the world wide web at the Acktar web site, www.acktar.com), or Avian Technologies (as described on http://www.aviantechnologies.com/products/coatings/diffuse_black.php), or other comparable coatings.

The stopper and the image sensor may be configured to have matching coefficients of thermal expansion (CTE). For example, the stopper and the image sensor may be configured to have a matching CTE of about $7 \cdot 10^{-6}$ $K^{-1}$. In order to match the CTE between the stopper and the image sensor where the stopper and image sensor have different CTEs, a liquid crystal polymer, such as Vectra E130, may be applied between the stopper and the image sensor.

The lens may be configured to introduce some distortion in the output of the lens, in order to improve performance in analyzing the obtained spectral data. The filters described herein may typically allow transmission of a specific wavelength for a specific angle of propagation of the incident light beam. As the light transmitted through the filters pass through the lens, the output of the lens may generate concentric rings on the sensor for different wavelengths of incident light. With typical spherical lens performance, as the angle of incidence grows larger, the concentric ring for that wavelength becomes much thinner (for a typical light bandwidth of ~5 nm). Such variance in the thickness of the rings may cause reduced linearity and related performance in analyzing the spectral data. To overcome this non-linearity, some distortion may be introduced into the lens, so as to reduce the thickness of the rings that correspond to incident light having smaller angles of propagation, and increase the thickness of the rings that correspond to incident light having larger angles of propagation, wherein non-linearity of ring size related to incident angle is decreased. Lenses configured to produce such distortion in the output can produce a more even distribution of ring thicknesses along the supported range of angles of incidence, consequently improving performance in the analysis of the generated spectral data. The distortion can be provided with one or more aspheric lens profiles to increase the depth of field (DoF) and increase the size of the point spread function (PSF) as described herein.

Figure 10:
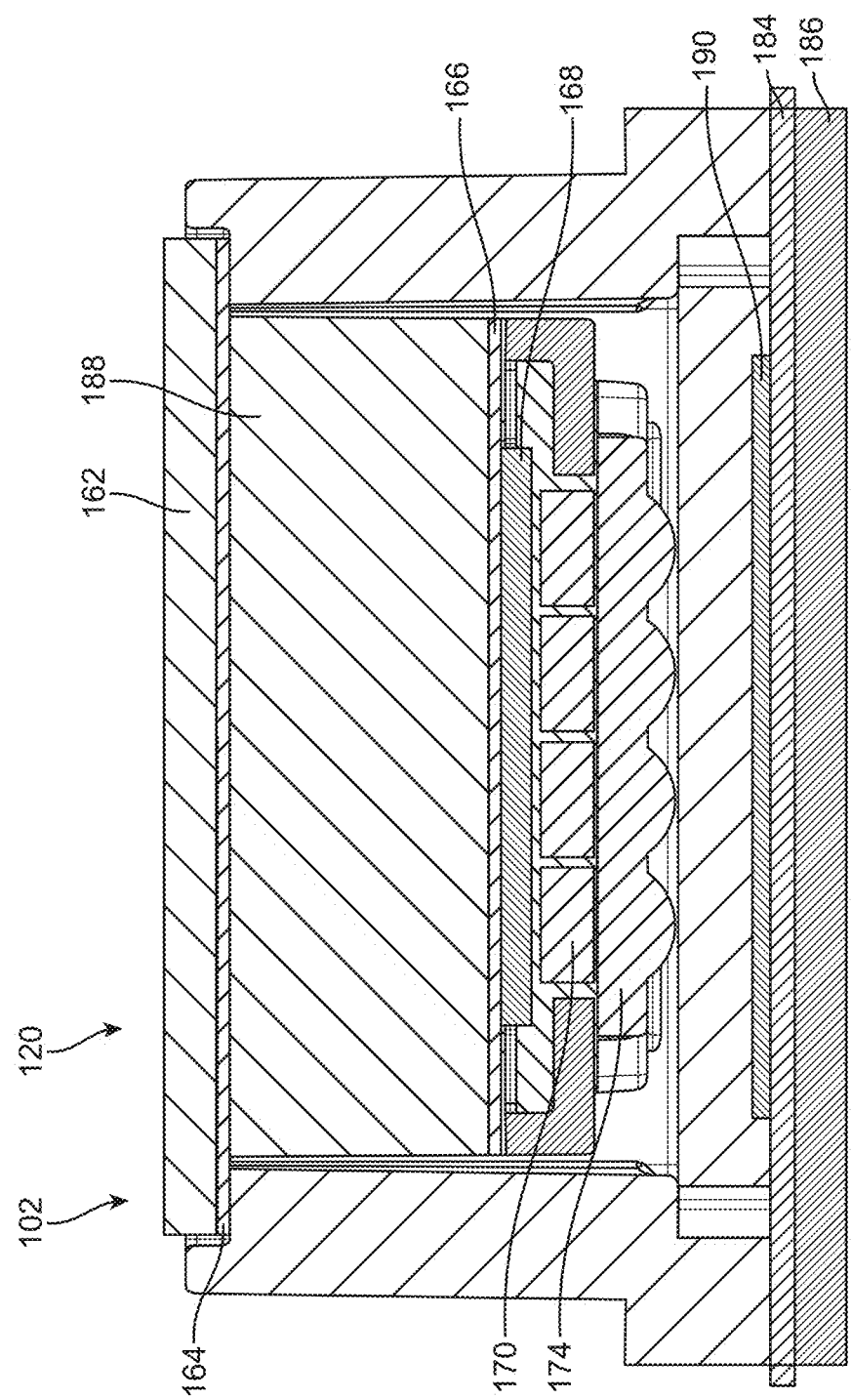
FIG. 10 shows a schematic diagram of an alternative embodiment of the spectrometer head, in accordance with configurations.

FIG. 10 shows a schematic drawing of a cross-section B of an alternative embodiment of the spectrometer head of FIG. 5. In some instances, the spectrometer module may be configured to purposefully induce cross-talk among sensor elements. For example, the spectrometer module may comprise the filter matrix and lens array as shown in FIG. 7, but omit one or more structural features that isolate the optical channels, such as the aperture array 172 or the isolated channels 177 of the support array 176. Without the isolated optical channels, light having a particular wavelength received by the first filter may result in a pattern of non-concentric rings on the detector. In addition, a first range of wavelengths associated with a first filter may partially overlap a second range of wavelengths associated with a second filter. Without the isolated optical channels, at least one feature in the pattern of light output by a first filter may be associated with at least one feature in the pattern of light output by a second filter. For example, when light comprising two different wavelengths, separated by at least five times the spectral resolution of the device, passes through the filter matrix, the light from at least two filters of the filter matrix may impinge on at least one common pixel of the detector. The spectrometer module may further comprise at least one processing device configured to stitch together light output by multiple filters to generate or reconstruct a spectrum associated with the incident light. Inducing cross-talk among sensor elements can have the advantage of increasing signal strength, and of reducing the structural complexity and thereby the cost of the optics.

Referring again to FIG. 6, the illumination module 140 can be configured to produce an optical beam 10, which may comprise a visible aiming beam 20 and a measurement beam 30. The aiming beam 20 and measurement beam 30 may be produced by the same light source 148, which may generate light including visible light. As described herein, the illumination module 140 may comprise a plate 146, such as a phosphor embedded glass plate. The plate may be configured to absorb a portion of the optical beam 10 produced by the light source 148, such that the absorbed light generates an electronic effect resulting in an emission of light with a wavelength different from the wavelength of the absorbed light. Alternatively or in combination, a portion of the optical beam 10 produced by light source 148 may be configured to be transmitted through plate 146 without being absorbed or wavelength-shifted. The unabsorbed, transmitted light can form the visible aiming beam 20, which can help the user visualize of the measurement area of a sample. A portion of the optical beam 10 may be wavelength-shifted by the plate 146 and can form the measurement beam 30, which may comprise light outside the visible spectrum and/or light in the visible spectrum, as described herein. For example, measurement beam 30 may comprise near infrared light. Parabolic concentrator 144 may be arranged to receive the aiming beam 20 and the measurement beam 30 and direct the aiming beam and measurement beam toward a sample material S. As described herein, the aiming beam 20 and measurement beam 30 may be partially or completely overlapping, aligned, or coaxial. For example, the aiming beam 20 may be arranged to be directed along an aiming beam axis 25, while the measurement beam 30 may be arranged to be directed along a measurement beam axis 35, and the aiming beam axis 25 may be co-axial with measurement beam axis 35. The aiming beam and measurement beam may overlap on the sample.

The power or visible light output of the aiming beam 20 may vary depending on the amount of optical beam 10 that is configured to pass through the plate 146 without being absorbed or wavelength-shifted. About 0.1% to about 10%, about 0.5% to about 5%, about 1% to about 4%, or about 2% to about 3% of optical beam 10 may be transmitted through plate 146 without being wavelength-shifted. The transmission of the optical beam 10 through plate 146 may be affected by the thickness of the plate 146. Further, the transmission of the optical beam 10 through plate 146 may be affected by the type of light source 148. For example, different types of light sources can be absorbed by the plate 146 at different efficiencies, consequently affecting the amount of light that is transmitted through the plate 146 without being wavelength-shifted. For a light source 148 comprising a blue LED and a plate 146 comprising phosphor-embedded glass, about 10 mW to about 15 mW (or about 0.4 to about 0.6 lumens) of light may transmit through the plate 146 to form the aiming beam 20. By comparison, light produced by a light source comprising a red LED may not absorb as efficiently by a phosphor-embedded glass plate, and consequently more light, for example about 15 mW to about 30 mW (or about 1 to about 2 lumens) of the light, may transmit through the plate to form the aiming beam 20.

The spectrometer module 160 may comprise one or more filters configured to transmit the measurement beam 30 but inhibit transmission of the aiming beam 20. In many configurations, the spectrometer module comprises one filter, such as light filter 188, configured to inhibit transmission of visible light, thereby inhibiting transmission of portions of the aiming beam 20 and measurement beam 30 reflected from the sample that comprise visible light. In some configurations, the spectrometer module may comprise a plurality of optical filters configured to inhibit transmission of a portion of the aiming beam 20 reflected the sample material S, and to transmit a portion of the measurement beam 30 reflected from the sample. For example, the plurality of optical filters may comprise the optical filters of the filter matrix 170, wherein each filter in the filter matrix 170 corresponds to an optical channel of the plurality of channels 177. Each filter may be configured to inhibit transmission of light within a specific range and/or within a specific angle of incidence, wherein the filtered specific range or specific angle of incidence may be specific to the corresponding channel. In some configurations, each optical channel may comprise a field of view. The field of view of the spectrometer module 160 may hence comprise a plurality of overlapping fields of view of the plurality of optical channels 177. The aiming beam 20 and the measurement beam 30 may overlap with the plurality of overlapping fields of view on the sample S.

Spectrometer Using Multiple Illumination Sources

Figure 11:
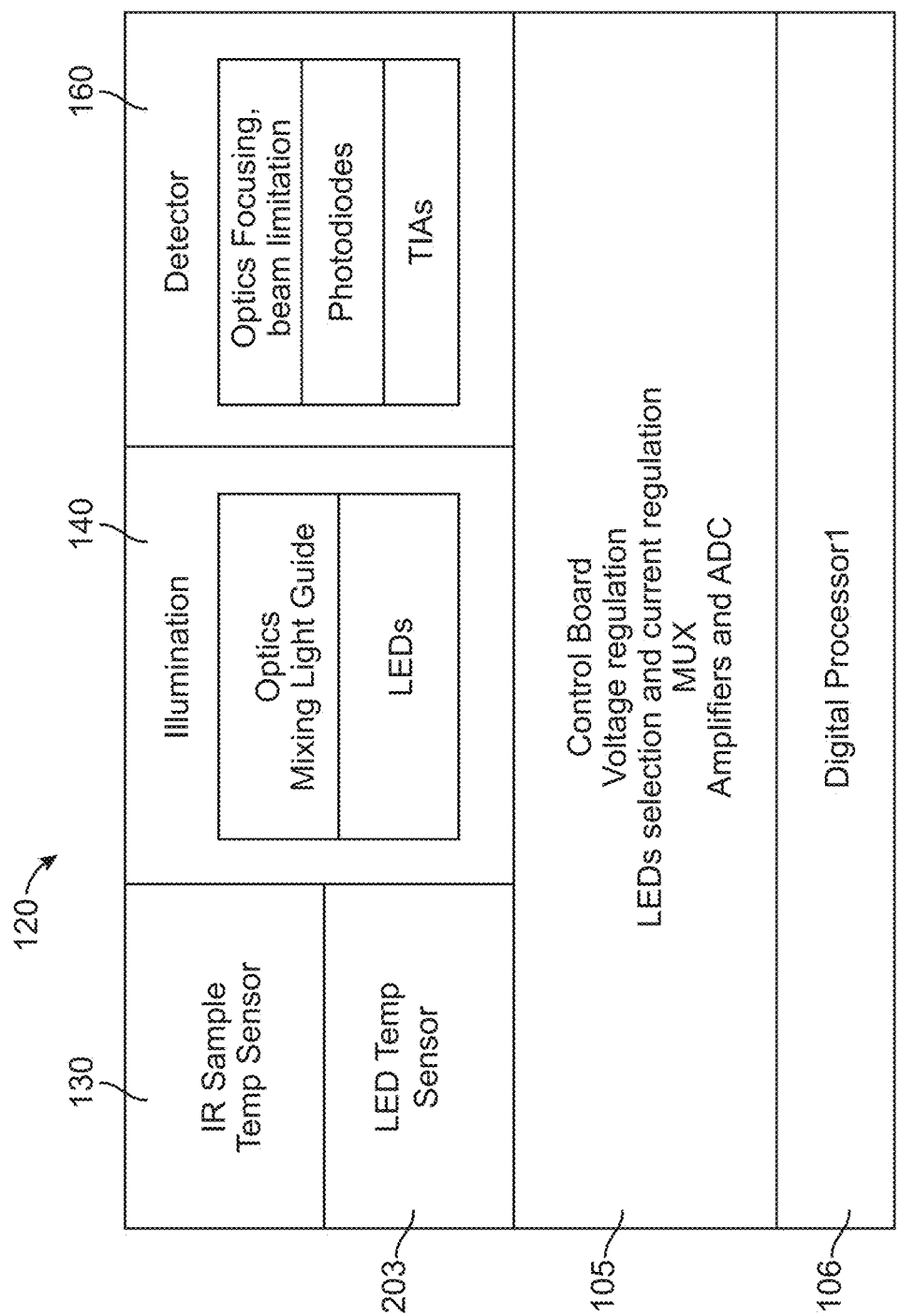
FIG. 11 shows a schematic diagram of an alternative embodiment of the spectrometer head, in accordance with configurations.

FIG. 11 shows a schematic diagram of an alternative embodiment of the spectrometer head 120. The spectrometer head 120 comprises an illumination module 140, a spectrometer module 160, a control board 105, and a processor 106. The spectrometer 102 further comprises a temperature sensor module 130 as described herein, configured to measure and record the temperature of the sample in response to infrared radiation emitted from the sample. In addition to the temperature sensor module 130, the spectrometer 102 may also comprise a separate temperature sensor 203 for measuring the temperature of the light source in the illumination module 140.

Figure 12:
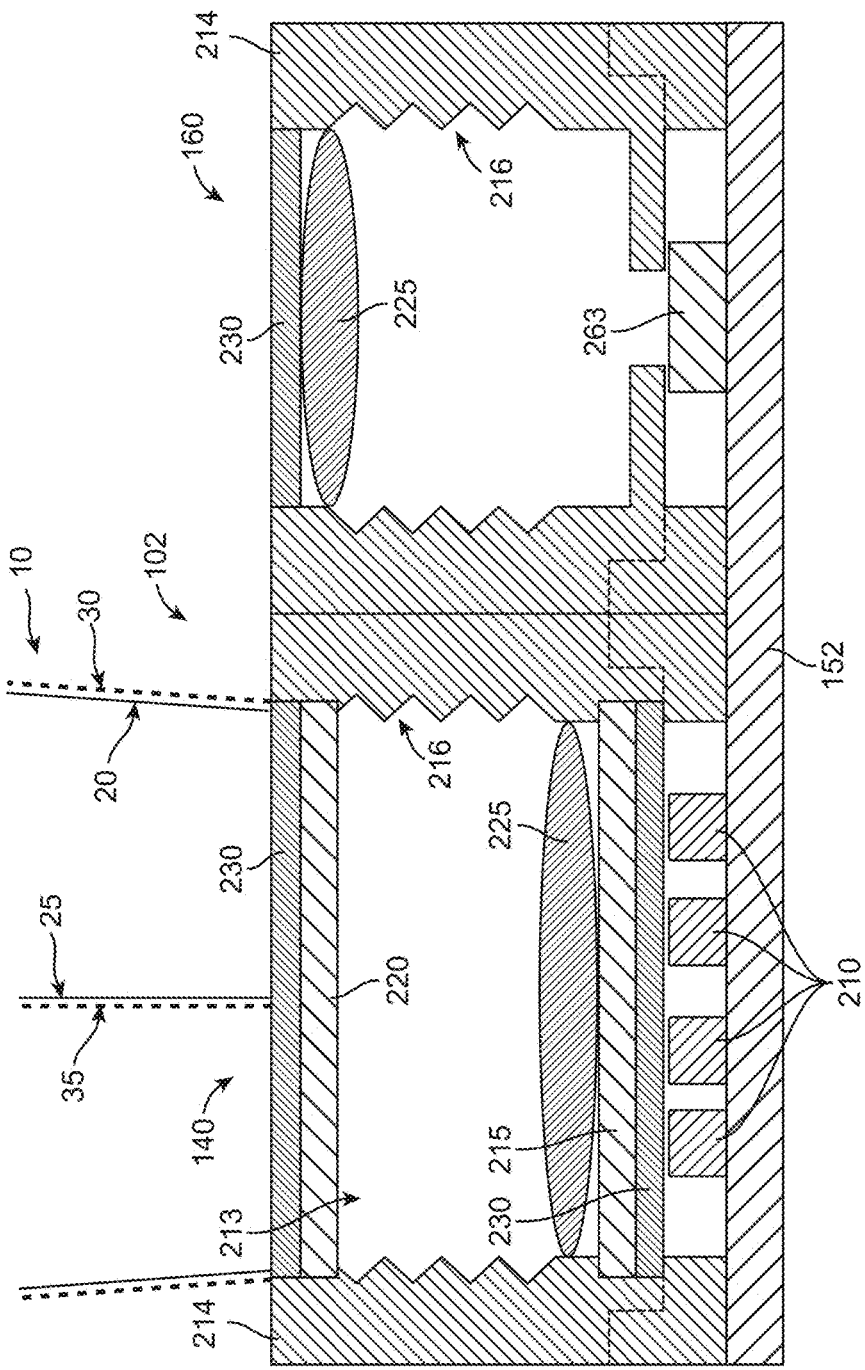
FIG. 12 shows a schematic diagram of a cross-section of the spectrometer head of FIG. 11.

FIG. 12 shows a schematic diagram of a cross-section of the spectrometer head of FIG. 11 (the sample temperature sensor 130 and the light source temperature sensor 203 are not shown). The spectrometer head comprises an illumination module 140 and a spectrometer module 160.

The illumination module 140 comprises at least two light sources, such as light-emitting diodes (LEDs) 210. The illumination module may comprise at least about 10 LEDs. The illumination module 140 further comprises a radiation diffusion unit 213 configured to receive the radiation emitted from the array of LEDs 210, and provide as an output illumination radiation for use in analyzing a sample material. The radiation diffusion unit may comprise one or more of a first diffuser 215, a second diffuser 220, and one lens 225 disposed between the first and second diffusers. The radiation diffusion unit may further comprise additional diffusers and lenses. The radiation diffusion unit may comprise a housing 214 to support the first diffuser and the second diffuser with fixed distances from the light sources. The inner surface of the housing 214 may comprise a plurality of light absorbing structures 216 to inhibit reflection of light from an inner surface of the housing. For example, the plurality of light absorbing structures may comprise one or more of a plurality of baffles or a plurality of threads, as shown in FIG. 12. A cover glass 230 may be provided to mechanically support and protect each diffuser. Alternatively or in combination with the LEDs, the at least two light sources may comprise one or more lasers.

The array of LEDs 210 may be configured to generate illumination light composed of multiple wavelengths. Each LED may be configured to emit radiation within a specific wavelength range, wherein the wavelength ranges of the plurality of LEDs may be different. The LEDs may have different specific power, peak wavelength and bandwidth, such that the array of LEDs generates illumination that spans across the spectrum of interest. There can be between a few LEDs and a few tens of LEDs in a single array.

Figure 13:
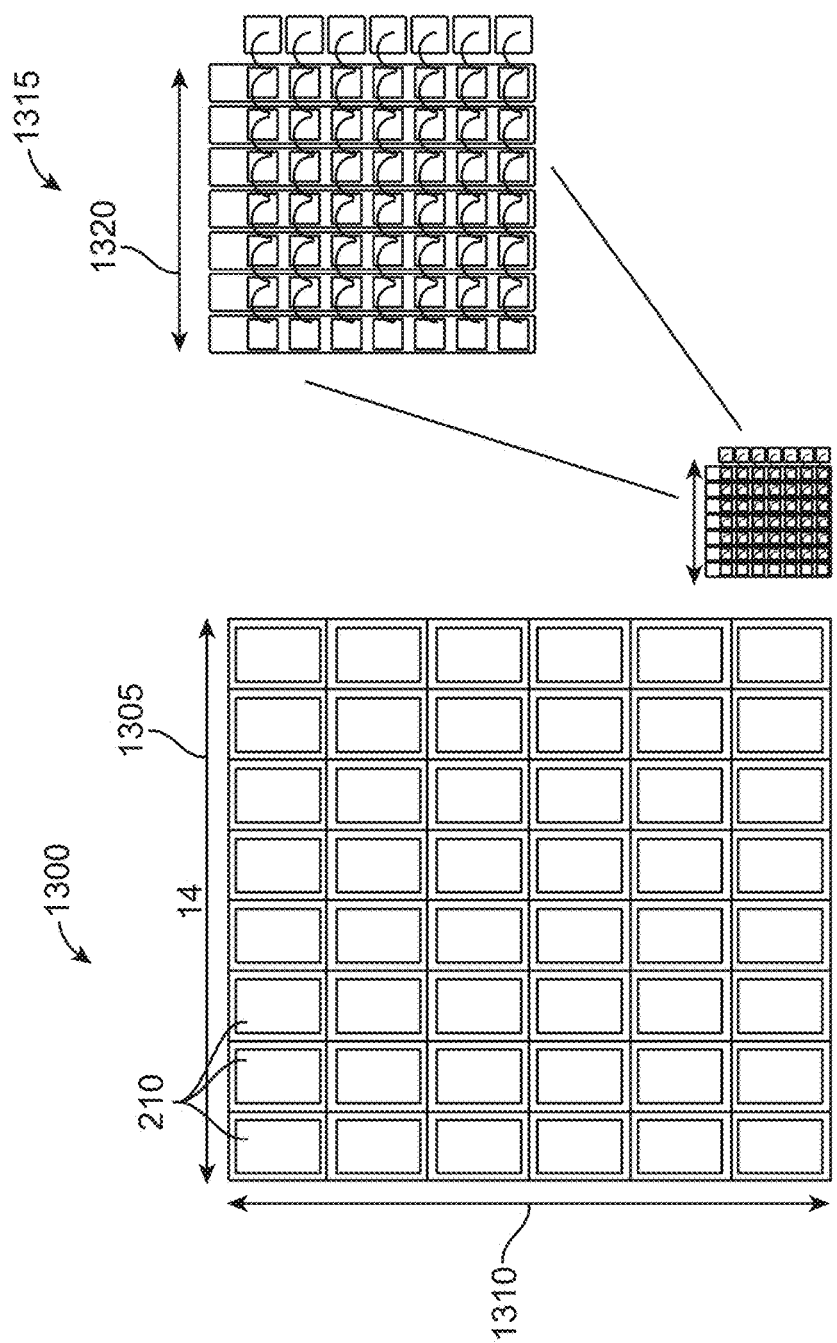
FIG. 13 shows an array of LEDs of the spectrometer head of FIG. 11 arranged in rows and columns, in accordance with configurations.

In some instances, the LED array is placed on a printed circuit board (PCB) 152. In order to reduce the size, cost and complexity of the PCB and LED driving electronics and reduce the number of interconnect lines, the LEDs may preferably be arranged in rows and columns, as shown in FIG. 13. The LED array may comprise a packaged LED array 1300 as shown, comprising a 2-dimensional array of LEDs 210, wherein the array may be about 14 mm in width 1305 and about 15 mm in length 1310, for example. The LED array may comprise a dice array 1315 as shown, which may be about 2.8 mm in width 1320 and comprise about 46 LEDs covering a spectral range of about 375 nm to about 1550 nm, for example. All anodes on the same row may be connected together and all cathodes on the same column may be connected together (or vice versa). For example, the LED in the center of the array may be turned on when a transistor connects the driving voltage to the anodes' fourth row and another transistor connects the cathodes' fourth column to a ground. None of the other LEDs is turned on at this state, as either its anodes are disconnected from power or its cathodes are disconnected from the ground. Preferably, the LEDs are arranged according to voltage groups, to simplify the current control and to improve spectral homogeneity (LEDs of similar wavelengths are placed close together). While bi-polar transistors are provided herein as examples, the circuit may also use other types of switches (e.g., field-effect transistors).

The LED currents can be regulated by various means as known to those skilled in the art. In some instances, Current Control Regulator (CCR) components may be used in series to each anode row and/or to each cathode column of the array. In some instances, a current control loop may be used instead of the CCR, providing more flexibility and feedback on the actual electrode currents. Alternatively, the current may be determined by the applied anode voltages, though this method should be used with care as LEDs can vary significantly in their current to voltage characteristics.

An optional voltage adjustment diode can be useful in reducing the difference between the LED driving voltages of LEDs sharing the same anode row, so that they can be driven directly from the voltage source without requiring a current control circuit. The optional voltage adjustment diode can also help to improve the stability and simplicity of the driving circuit. These voltage adjustment diodes may be selected according to the LEDs' expected voltage drops across the row, in opposite tendency, so that the total voltage drop variation along a shared row is smaller.

Referring to FIG. 12, the radiation diffusion unit 213, positioned above the LED array, is configured to mix the illumination emitted by each of the LEDs at different spatial locations and with different angular characteristics, such that the spectrum of illumination of the sample will be as uniform as possible across the measured area of the sample. What is meant by a uniform spectrum is that the relations of powers at different wavelengths do not depend on the location on the sample. However, the absolute power can vary. This uniformity is highly preferable in order to optimize the accuracy of the reflection spectrum measurement.

Figure 14:
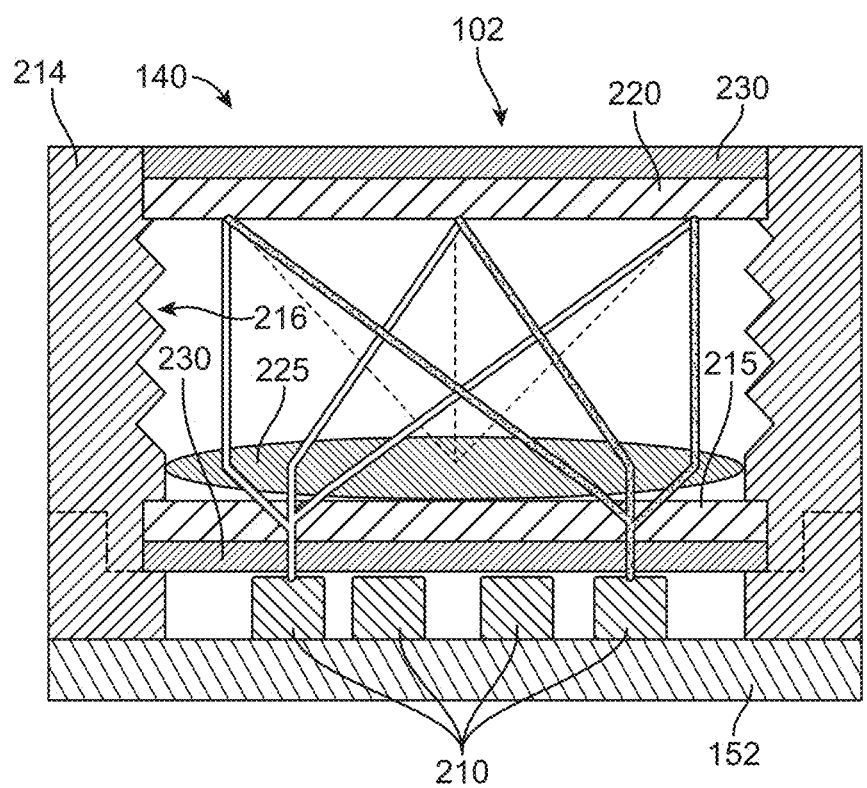
FIG. 14 shows a schematic diagram of a radiation diffusion unit of the spectrometer head of FIG. 11, in accordance with configurations.

The first diffuser 215, preferably mechanically supported and protected by a cover glass 230, may be placed above the array of LEDs 210. The diffuser may be configured to equalize the beam patterns of the different LEDs, as the LEDs will typically differ in their illumination profiles. Regardless of the beam shape of any LED, the light that passes through the first diffuser 215 can be configured to have a Lambertian beam profile, such that the emitted spectrum at each of the directions from first diffuser 215 is uniform. Ideally, the ratios between the illuminations at different wavelengths do not depend on the direction to the plane of the first diffuser 215, as observed from infinity. Such directions are indicated schematically by the dashed lines shown in FIG. 14, referring to the directions of rays at the output of the first diffuser 215 towards the first surface of lens 225.

The first diffuser 215 is preferably placed at the aperture plane of the lens 225. Thus, parallel rays can be focused by the lens to the same location on the focal plane of the lens, where the second diffuser 220 is placed (preferably supported and protected by cover glass 230). Since all illumination directions at the output of the first diffuser 215 have the same spectrum, the spectrum at the input plane of the second diffuser 220 can be uniform (though the absolute power may vary). The second diffuser 220 can then equalize the beam profiles from each of the locations in its plane, so that the output spectrum is uniform both in location and in direction, leading to uniform spectral illumination across the sample irrespective of the sample distance from the device (when the sample is close to the device it is more affected by the spatial variance of spectrum, and when the sample is far from the device it is more affected by the angular variation of the spectrum).

Figure 15A:
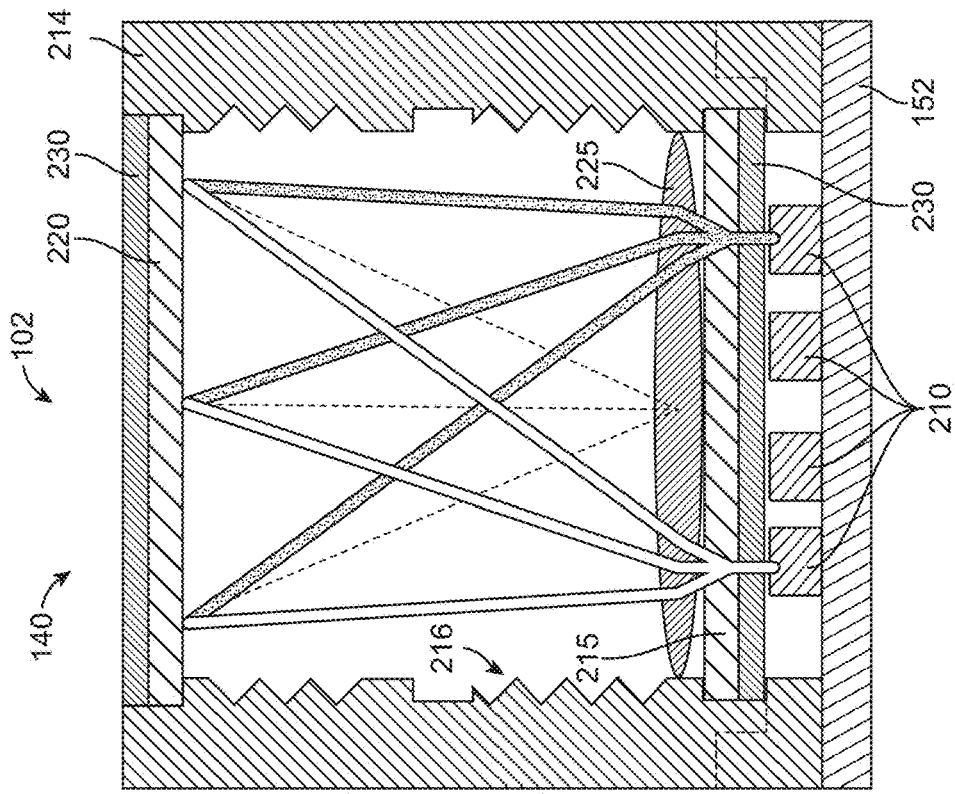
FIGS. 15A and 15B show examples of design options for the radiation diffusion unit of FIG. 13, in accordance with configurations.
Figure 15B:
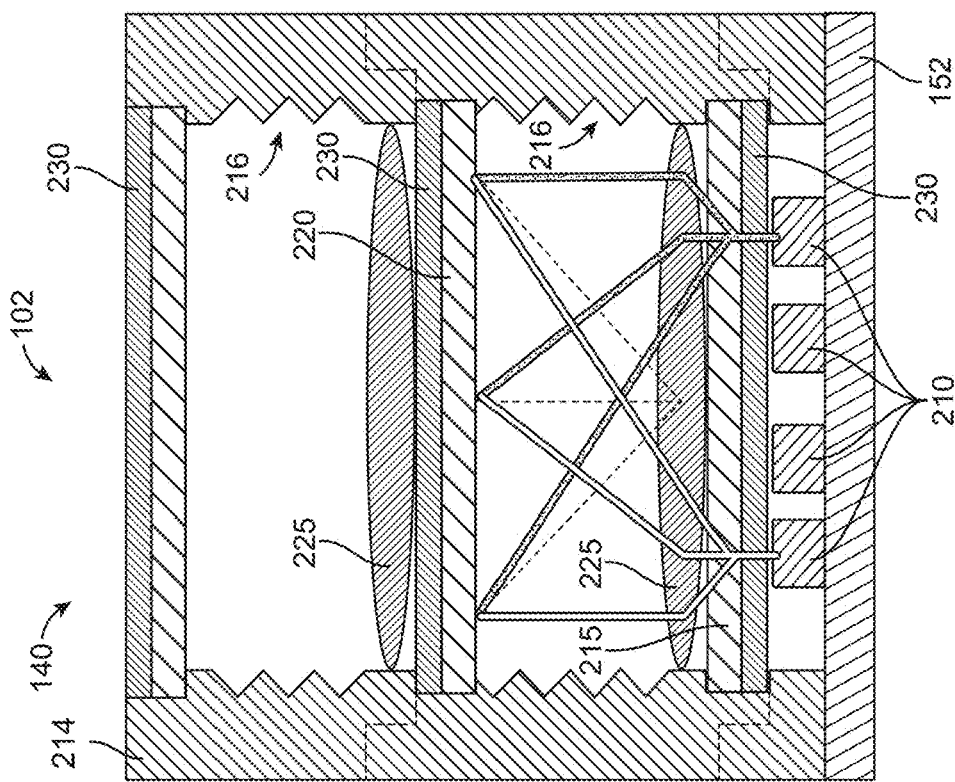

In designing the radiation diffusion unit 213 configured to improve spectral uniformity, size and power may be traded off in order to achieve the required spectral uniformity. For example, as shown in FIG. 15A, the radiation diffusion unit 213 may be duplicated (additional diffusers and lenses added), or as shown in FIG. 15B, the radiation diffusion unit 213 may be configured with a longer length between the first and second diffusers, in order to achieve increased uniformity while trading off power. Alternatively, if uniformity is less important, some elements in the optics can be omitted (e.g., first diffuser or lens), or simplified (e.g., weaker diffuser, simpler lens).

Referring back to FIG. 12, the spectrometer module 160 comprises one or more photodiodes 263 that are sensitive to the spectral range of interest. For example, a dual Si—InGaAs photodiode can be used to measure the sample reflection spectrum in the range of about 400 nm to about 1750 nm. The dual photodiode structure is composed of two different photodiodes positioned one above the other, such that they collect illumination from essentially the same locations in the sample.

The one or more photodiodes 263 are preferably placed at the focal plane of lens 225, as shown in FIG. 12. The lens 225 can efficiently collect the light from a desired area in the sample to the surface of the photodiode. Alternatively, other light collection methods known in the art can be used, such as a Compound Parabolic Concentrator.

The photodiode current can be detected using a transimpedance amplifier. For the dual photodiode architecture embodiment, the photocurrent can first be converted from current to voltage using resistors with resistivity that provides high gain on the one hand to reduce noise, while having a wide enough bandwidth and no saturation on the other hand. An operational amplifier can be connected in photovoltaic mode amplification to the photodiodes, for minimum noise. Voltage dividers can provide a small bias to the operational amplifier (Op Amp) to compensate for possible bias current and bias voltage at the Op Amp input. Additional amplification may be preferable with voltage amplifiers.

In the embodiment of the spectrometer head shown in FIG. 12, each photodiode 263 is responsive to the illumination from typically many LEDs (or wavelengths). In order to identify the relative contribution of light from each of the LEDs, the LED current may be modulated, then the detected photocurrent of the photodiodes may be demodulated.

In some instances, the modulation/demodulation may be achieved by time division multiplexing (TDM). In TDM, each LED is switched "on" in a dedicated time slot, and the photocurrent sampled in synchronization to that time slot represents the contribution of the corresponding LED and its wavelength. Black level and ambient light is measured at the "off" times between "on" times.

In some instances, the modulation/demodulation may be achieved by frequency division modulation (FDM). In FDM, each LED is modulated at a different frequency. This modulation can be with any waveform, and preferably by square wave modulation for best efficiency and simplicity of the driving circuit. This means that at any given time, one or more of the LEDs can be "on" at the same time, and one of more of the LEDs can be "off" at the same time. The detected signal is decomposed to the different LED contributions, for example by using matched filter or fast Fourier transform (FFT), as known to those skilled in the art.

FDM may be preferable with respect to TDM as FDM can provide lower peak current than TDM for the same average power, thus improving the efficiency of the LEDs. The higher efficiency allows for lower LED temperatures, which in turn provide better LED spectrum stability. Another advantage of FDM is that FDM has lower electromagnetic interference than TDM (since slower current slopes can be used), and smaller amplification channel bandwidth requirement than TDM.

In some instances, the modulation/demodulation may be achieved by amplitude modulation, each at a different frequency.

When the LED array uses a shared-electrodes architecture, a single LED can be turned "on" when the corresponding row and column are connected (e.g., anode to power and cathode to GND). However, when more than one row and one column is switched "on", all the LEDs sharing the connected rows and columns will be switched on. This can complicate the modulation/demodulation scheme. In order to resolve such a complication, TDM may be used, wherein a single row and a single column is enabled at each "on"

time slot. Alternatively, combined TDM and FDM may be used, wherein a single row is selected with TDM, and FDM is applied on the columns (or vice versa). Alternatively, a 2-level FDM may be used, wherein each row and each column is modulated at different frequencies. The LEDs can be decoupled using matched filter or spectrum analysis, while taking special care to avoid overlapping harmonics of base frequencies.

Referring again to FIG. 12, the illumination module 140 can be configured to produce an optical beam 10, which may comprise a visible aiming beam 20 and a measurement beam 30. As described herein, the visible aiming beam 20 and measurement beam 30 may be partially or completely overlapping, aligned, or coaxial (e.g., around co-axial aiming beam axis 25 and measurement beam axis 35). The aiming beam 20 and measurement beam 30 may be produced by the same light source, which may comprise two or more LEDs 210. One or more of the two or more LEDs 210 may produce light in the visible spectrum, and output enough visible light to form the aiming beam 20. All or a portion of the light output from the one or more LEDs in the visible range may form the visible aiming beam 20. Optionally, operation of one or more of the LEDs 210 may be adjusted such that the visibility of the aiming beam 20 is enhanced.

Spectrometer System

In some embodiments, the spectrometer system described herein includes a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the spectrometer system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the spectrometer system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the spectrometer system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the spectrometer system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Referring again to FIG. 2, the spectrometer system 100 typically comprises a spectrometer 102 as described herein and a hand held device 110 in wireless communication 116 with a cloud based server or storage system 118. The spectrometer system 100 can provide a system for analyzing a material in real time, to determine the identity and/or additional properties of the material. The obtained information regarding the material can then guide users in making decisions relating to the identified material. The spectrometer 102 may have a warm-up time of less than 5 seconds, in some instances less than 1 second, in order to support real-time material analysis. The spectrometer can then send the data to a hand held device 110, for example via communication circuitry 104 having a communication link such as Bluetooth™. The hand held device 110 can transmit the data to the cloud based storage system 118. The data can be processed and analyzed by the cloud based server 118, and transmitted back to the hand held device 110 to be displayed to the user. The hand held device 110 may provide a user interface (UI) for controlling the operation of the spectrometer 102 and/or viewing data as described in further detail herein.

The hand held device 110 may comprise one or more of a smartphone, tablet, or smartwatch, for example. In some cases, a single device having internet connectivity is configured to communicate with the spectrometer on the one hand and with the cloud based server on the other hand. In some cases, the spectrometer system 100 comprises two or more hand held devices, connected via Bluetooth communication and/or internet connection. Each of the two or more hand held devices may be configured to communicate with the other devices of the system either directly or through another hand held device of the system. For example, the system may comprise a mobile phone and a smartwatch, wherein the mobile phone is in communication with the spectrometer and the cloud based server as described. The smartwatch may be configured to communicate with the mobile phone via a wireless data connection such as Bluetooth, wherein the smartwatch can be configured to control the user interface of the mobile phone and/or display data received from the mobile phone. In some cases, the smartwatch may be configured to have internet connection, and may be used in place of the mobile phone to function as the data relay point between the spectrometer and the cloud based server, and to present the user interface to the user.

One or more of the spectrometer, hand held device, and cloud based server of the system may comprise a computer system configured to regulate various aspects of data acquisition, transfer, analysis, storage, and/or display. The computer system typically comprises a central processing unit (also "processor" herein), a memory, and a communication interface (also "communication circuitry" herein). The processor can execute a sequence of machine-readable instructions, which can be embodied in a program or software. The instructions may be stored in a memory location. Each device of the spectrometer system may communicate with one or more of the other devices of the system via the communication interface.

Figure 16:
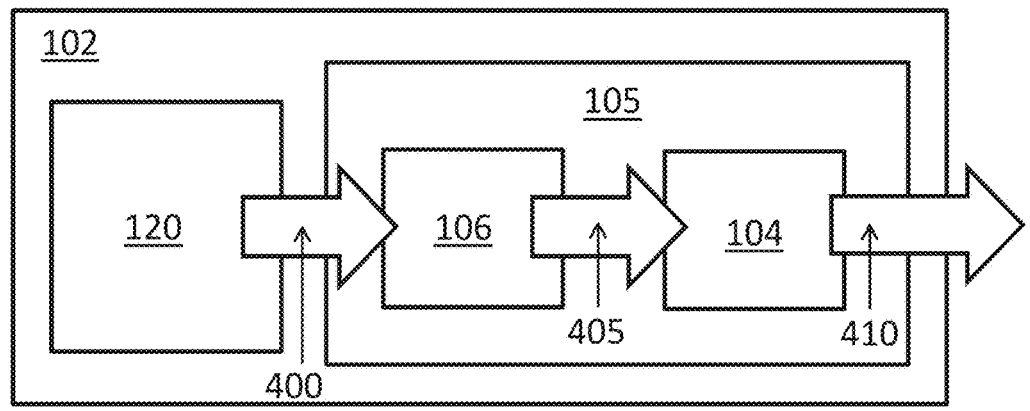
FIG. 16 shows a schematic diagram of the data flow in the spectrometer, in accordance with configurations.

FIG. 16 shows a schematic diagram of the data flow in the spectrometer 102, in accordance with configurations. The spectrometer head 120 is configured to acquire raw intensity data for a material when a user scans a material with the spectrometer 102. In addition to the raw spectral data, non-spectral data may also be obtained if the spectrometer 102 includes a sensor module such as a temperature sensor module described herein. The raw data 400 generated by the spectrometer head 120 may be transmitted to a processor 106 of the control board 105. The processor 106 may comprise a tangible medium comprising instructions of a computer program; for example, the processor may comprise a digital signal processing unit, which can be configured to compress the raw data. The compressed raw data signal 405 can then be transmitted to the communication circuitry 104, which may comprise a data encryption/transmission component such as Bluetooth™. Once encrypted, the compressed encrypted raw data signal 410 can be transmitted via Bluetooth to the hand held device 110.

Compression of raw data may be necessary since raw intensity data will generally be too large to transmit via Bluetooth in real time. The compression may be performed using a data compression algorithm tailored according to the physical properties of the optical system that create the spatial distribution of light onto the light detector of the spectrometer module. The data generated by the optical system described herein typically contains symmetries that allow significant compression of the raw data into much more compact data structures.

Figure 17:
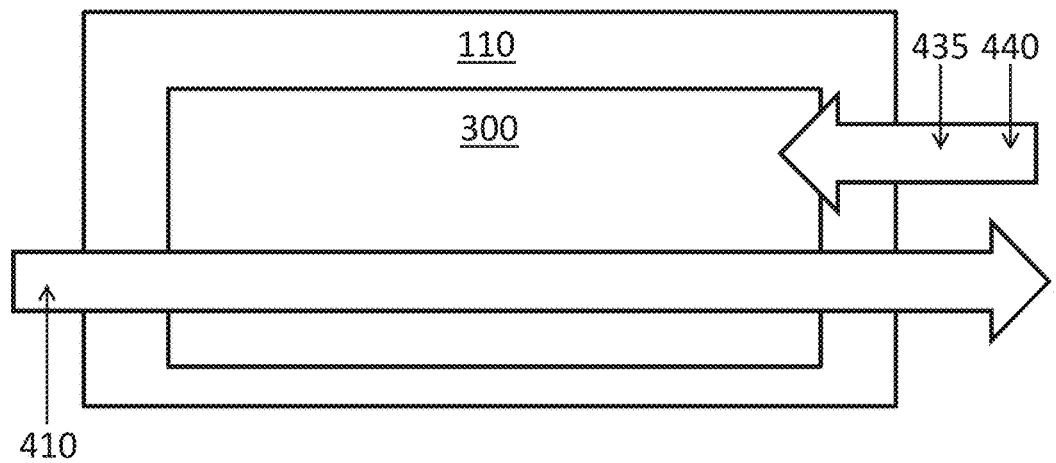
FIG. 17 shows a schematic diagram of the data flow in the hand held device, in accordance with configurations.

FIG. 17 shows a schematic diagram of the data flow in the hand held device 110. The hand held device 110 can comprise a processor having a computer readable memory, the memory embodying instructions for presenting a user interface (UI) 300 for the spectrometer system via a display of the hand held device 110. For example, in configurations comprising a mobile phone, a readable memory of the phone may comprise machine executable code in the form of a mobile application, providing instructions for presenting the UI. The hand held device 110 can also comprise a means for receiving user input to the UI, such as a touch-screen interface. The UI provides a space where users may interact with the spectrometer 102 and with the cloud server 118. For example, the UI can provide a user with the means for controlling the operation of the spectrometer 102, selecting analyses types to perform on the data generated from the sample scan, viewing the analyzed data from a sample scan, and/or viewing data from a database stored on the processor of the hand held device 110 or on the cloud server 118. In configurations of the system comprising two or more hand held devices 110 in communication with one another, the spectrometer may be in communication with a first device, and the first device may be in communication with a second device comprising the display for the UI.

The encrypted, compressed raw data signal 410 from the spectrometer may be received by the UI 300 of the hand held device 110, wherein the UI is provided by a processor of the hand held device. The UI may then transmit the data 410 to the cloud server 118, for example via a wireless internet connection. Data may be transmitted automatically in real time or at certain intervals, or data may be transmitted when requested by a user. The UI can optionally add metadata 415 such as time, location, and user information to the raw data and transmit the data set. A user may also provide instructions to the UI to perform one or more specific types of analysis; in this case, the UI may transmit, along with the compressed, encrypted raw data 410 and/or metadata 415, user instructions for performing the analysis.

Figure 18:
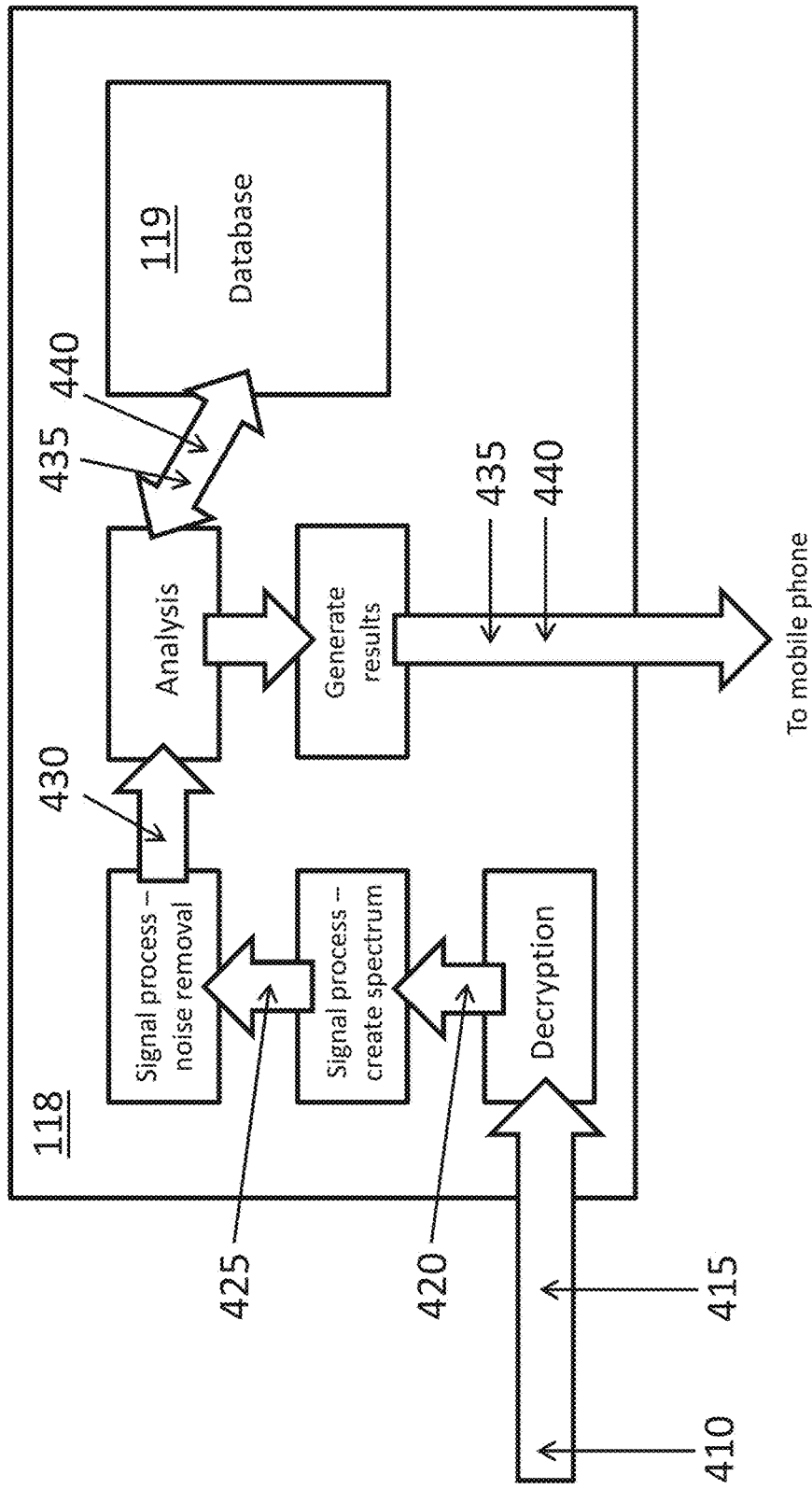
FIG. 18 shows a schematic diagram of the data flow in the cloud based storage system, in accordance with configurations.

FIG. 18 shows a schematic diagram of the data flow in the cloud based storage system or server 118. The cloud server 118 can receive compressed, encrypted data 410 and/or metadata 415 from the hand held device 110. A processor or communication interface of the cloud server can then decrypt the data, and a digital signal processing unit of the cloud server can perform signal processing on the decrypted signal 420 to transform the signal into spectral data 425. The server may perform additional pre-processing of the spectrum, such as noise reduction, to produce pre-processed spectral data 430. Analysis of the pre-processed spectrum 430 can then be performed by a processor of the server having instructions stored thereon for performing various data analysis algorithms. The analyzed spectral data 435 and/or additional analysis results 440 (e.g., nutritional content of food, quality of gems, etc.) may be transmitted back from the server to the hand held device, so that the results may be displayed to the user via the display of the hand held device. In addition, the analyzed spectral data 435 and/or related additional analysis results 440 may be dynamically added to a universal database 119 operated by the cloud server, where spectral data associated with sample materials may be stored. The spectral data stored on the database 119 may comprise data generated by the one or more users of the spectrometer system 100, and/or pre-loaded spectral data of materials with known spectra. The cloud server may comprise a memory having the database 119 stored thereon.

The cloud based system or server 118 may be accessed remotely, for example via wireless internet connection, by one or more spectrometers and hand held devices of the spectrometer system. In many instances, the cloud server is simultaneously accessible by more than one users/hand held devices of the system. Hand held devices up to the order of millions can be simultaneously connected to the cloud server.

The multiple spectrometers 102 within a spectrometer system 100 may differ from one another, for example due to variations in manufacturing. Such differences among the multiple spectrometers may yield significant variations in the spectral data for the same material obtained by each spectrometer. In order to ensure that the data contributed to the universal database 119 by multiple users are comparable, the system may comprise a method for calibrating the data generated by each spectrometer, before adding the data to the universal database. For example, the specific optical response of each spectrometer may be characterized during manufacturing, by measuring how each spectrometer behaves in response to different kinds of inputs. The inputs may comprise a set of calibration patterns (spectra) that are measured with the spectrometer, and the corresponding spectrometer response function may be determined and output with the calibration data. This spectrometer-specific optical response data may be saved and stored as the calibration data for the specific spectrometer, typically in the cloud based server. The calibration data may be stored tagged with an identifier for the specific spectrometer, such that when the server receives raw data from the spectrometer, the server can identify and locate the appropriate calibration data for the specific spectrometer. The server may then apply the spectrometer-specific calibration data in producing the spectral data from the raw data received from the spectrometer. Such a calibration process can compensate for device-to-device variation, providing a way for multiple users of the system to make meaningful comparisons among data for the same material obtained using different spectrometers.

The cloud based server 118 may provide users of the spectrometer system 100 with a way of sharing the information obtained in a particular measurement. Database 119 located in the cloud server can constantly receive the results of measurements made by individual users and update itself in real time or at regular intervals. The updating of the database 119 based on user contribution can rapidly expand the number of substances for which a spectral signature is available. Thus, each measurement made by a user can contribute towards increasing the accuracy and reliability of future measurements made by any user of the spectrometer system.

The sharing of information among multiple users of the spectrometer system through the cloud based server can provide a useful tool for making informed decisions regarding materials of interest. For example, a user shopping for apples may be interested in finding out what stores may carry the sweetest apples. The spectrometer system may provide the user with a means for viewing a map of matter for apples, the map of matter presenting a comprehensive compilation of user-contributed, analyzed spectral and non-spectral data for specific materials, as described in further detail herein. The map of matter may be visualized based on geographical location, providing users with the ability to view what stores in the area carry relatively sweet apples. The map of matter may also be visualized based on time/date, such that users may view the data for apples for different time windows (e.g., within the last hour/day/week/month, on a certain date or over a certain date range, etc.). Alternatively or in combination, the map of matter may also provide visualization of material data based on store/branch, type of object, temperature, number of measurements, and many other factors. For example, the system may provide users with a location-based map displaying all data for apples in the universal database, and users may be click on a particular location/store to view the data summary for the selected store. The store-specific data summary may also be viewed on a timeline, allowing users to determine the trend in the sweetness of apples carried by the store over time. The spectrometer system may thus be used to make a more informed purchasing decision.

The spectrum of a sample material can be analyzed using any appropriate analysis method. The processor of the cloud server 118, hand held device 110, or spectrometer 102 may comprise one or more algorithms for spectrum analysis. Non-limiting examples of spectral analysis techniques that can be used include Principal Components Analysis, Partial Least Squares analysis, and the use of a neural network algorithm to determine the spectral components.

In configurations in which a Raman spectrum is obtained, the Raman signal can be separated from any fluorescence signal. Both Raman and fluorescence spectra can be compared to existing calibration spectra. After a calibration is performed, the spectra can be analyzed using any appropriate algorithm for spectral decomposition; non-limiting examples of such algorithms include Principal Components Analysis, Partial Least-Squares analysis, and spectral analysis using a neural network algorithm. This analysis provides the information needed to characterize the sample that was tested using the spectrometer. The results of the analysis can then be presented to the user.

The analysis may or may not be in real time, and the analysis may or may not be contemporaneous.

The spectrometer system may perform analysis of the raw data locally. The spectrometer system may comprise a memory with a database of spectral data stored therein, and a processor with analysis software programmed with instructions. The memory can be volatile or non-volatile in order to store the user's own measurements in the memory. Alternatively, the database of spectral data can be provided with a computer located near the spectrometer, for example in the same room. Alternatively or in combination, the spectrometer may partially analyze the raw data prior to transmission to a remote server, such as the cloud server 118 described herein, wherein heavier calculations for more complicated analyses may be performed.

An analyzed spectrum can determine whether a complex mixture being investigated contains a spectrum associated with components. The components can, for example, be a substance, mixture of substances, or microorganisms. The intensity of these components in the spectrum can be used to determine whether a component is at a certain concentration, and whether the concentration of an undesirable component is high enough to be of concern. Non-limiting examples of such substances include toxins, decomposition products, or harmful microorganisms. In some configurations of the invention, if it is deemed likely that the sample is not fit for consumption, the user is provided with a warning. Various possible applications of the compact spectrometer system are described in further detail herein.

The spectrometer system 100 may be configured to operate in an off-line mode, when the spectrometer system does not have access to an internet connection, for example. A sample may be measured by the spectrometer 102 in an area lacking internet connection, or the hand-held device 110 of the spectrometer system 100 may be unable to connect to the internet. Without access to an internet connection, the spectrometer 102 and hand-held device 100 may be unable to access the cloud based server 118 for data analysis. The spectrometer 102 may then store the raw data locally, for example in a memory of the spectrometer or in a hand-held device 110 such as a mobile phone, for later analysis. Alternatively or in combination, the spectrometer 102 may be configured to analyze the raw data locally using data analysis models or algorithms stored locally, for example in a memory of the spectrometer or in a hand-held device 110 such as a mobile phone. The data analysis models and algorithms may be downloaded by users from the cloud based server 118 to the hand-held device 110 or spectrometer 102, when the system has access to an internet connection.

Figure 30:
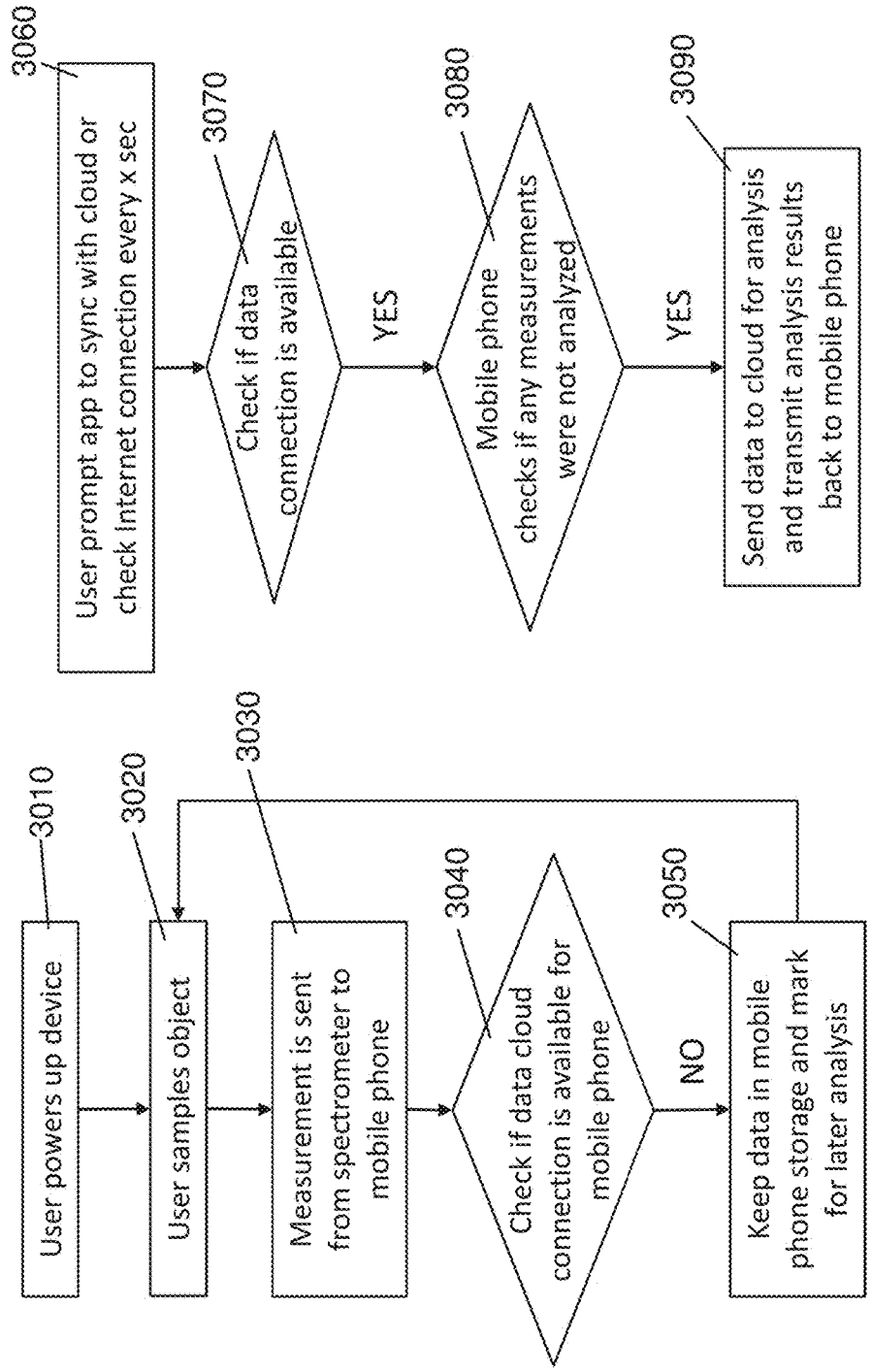
FIG. 30 shows a schematic diagram of an off-line mode of operation of the compact spectrometer, wherein the raw data is stored locally for later analysis.

FIG. 30 shows a schematic diagram of an off-line mode of operation of the compact spectrometer 102, wherein the raw data is stored locally for later analysis. At step 3010, the spectrometer 102 may be powered up, and then used to measure the spectra of a sample material or object at step 3020. At step 3030, the raw data, which may be a compressed and encrypted raw data signal 410 as shown in FIG. 16, may be transmitted from the spectrometer 102 to the hand-held device 110 such as a mobile phone. At step 3040, the hand-held device 110 may then check if connection to the cloud server 118 is available. If the hand-held device is unable to access the cloud server 118, at step 3050, the raw data may be stored locally, for example in a memory of the hand-held device 110, and marked for later analysis. At step 3060, the user may prompt the user interface (e.g., a mobile app) of the hand-held device to check internet connection or synchronize with the cloud server 118 at regular intervals, for example every few seconds. At step 3070, the user interface may check whether connection to the cloud server is available. If connection is available, at step 3080, the user interface may be configured to check whether there is any unanalyzed, raw data stored locally, for example in a mobile app of the hand-held device. If locally stored raw data is detected, at step 3090, the raw data may be sent to the cloud server 118 for analysis, where the analysis may be performed using models and algorithms stored on the server as described in further detail herein. The analyzed data (e.g., analyzed spectral data 435, additional analysis results 440, as shown in FIGS. 17 and 18) may be transmitted back from the server to the hand-held device to be displayed to the user.

Figure 31:
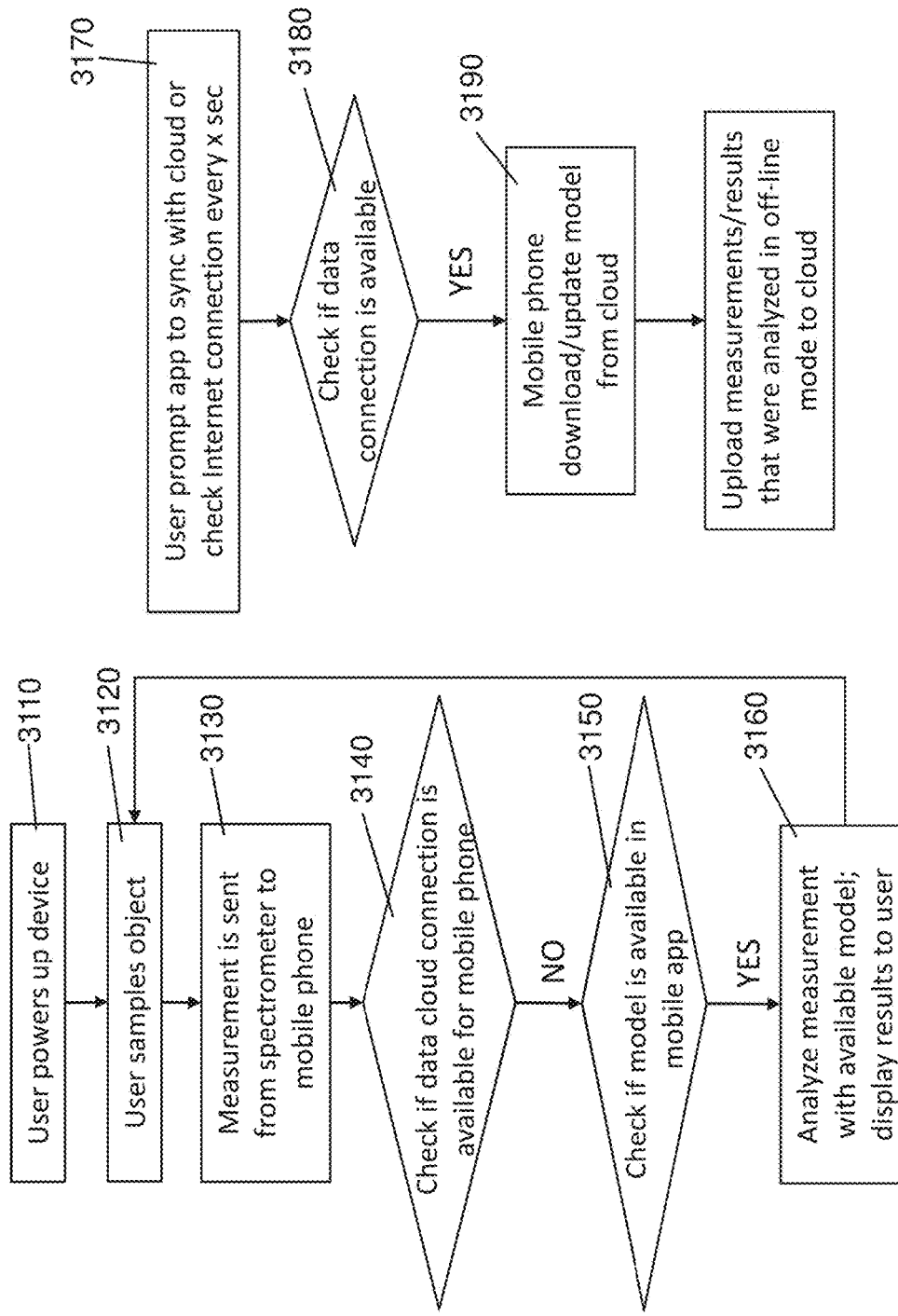
FIG. 31 shows a schematic diagram of an off-line mode of operation of compact spectrometer, wherein the raw data is analyzed locally.

FIG. 31 shows a schematic diagram of an off-line mode of operation of compact spectrometer 102, wherein the raw data is analyzed locally. At step 3110, the spectrometer may be powered up, and then used to measure the spectra of a sample material or object at step 3120. At step 3130, the raw data, which may be a compressed and encrypted raw data signal 410 as shown in FIG. 16, may be transmitted from the spectrometer 102 to the hand-held device 110 such as a mobile phone. At step 3140, the hand-held device 110 may then check if connection to the cloud server 118 is available. If the hand-held device is unable to access the cloud server 118, at step 3150, the user interface of the hand-held device may check if there are any available data analysis models or algorithms stored locally, for example in a mobile app of the hand-held device. If no such models are available, the raw data may be stored for later analysis as described in FIG. 30. If the models are available, at step 3160, the user interface may analyze the raw data off-line using the available models, and store and display to the user the analyzed data and results. At step 3170, the user may prompt the user interface (e.g., a mobile app) of the hand-held device to check internet connection or synchronize with the cloud server 118 at regular intervals, for example every few seconds. At step 3180, the user interface may check whether connection to the cloud server is available. If connection is available, at step 3190, the hand held device may download and/or update data analysis models and algorithms from the cloud server. At step 3120, any data that was analyzed off-line and stored locally may be uploaded to the server and added to the universal database of the server, as described in further detail herein.

Figure 32:
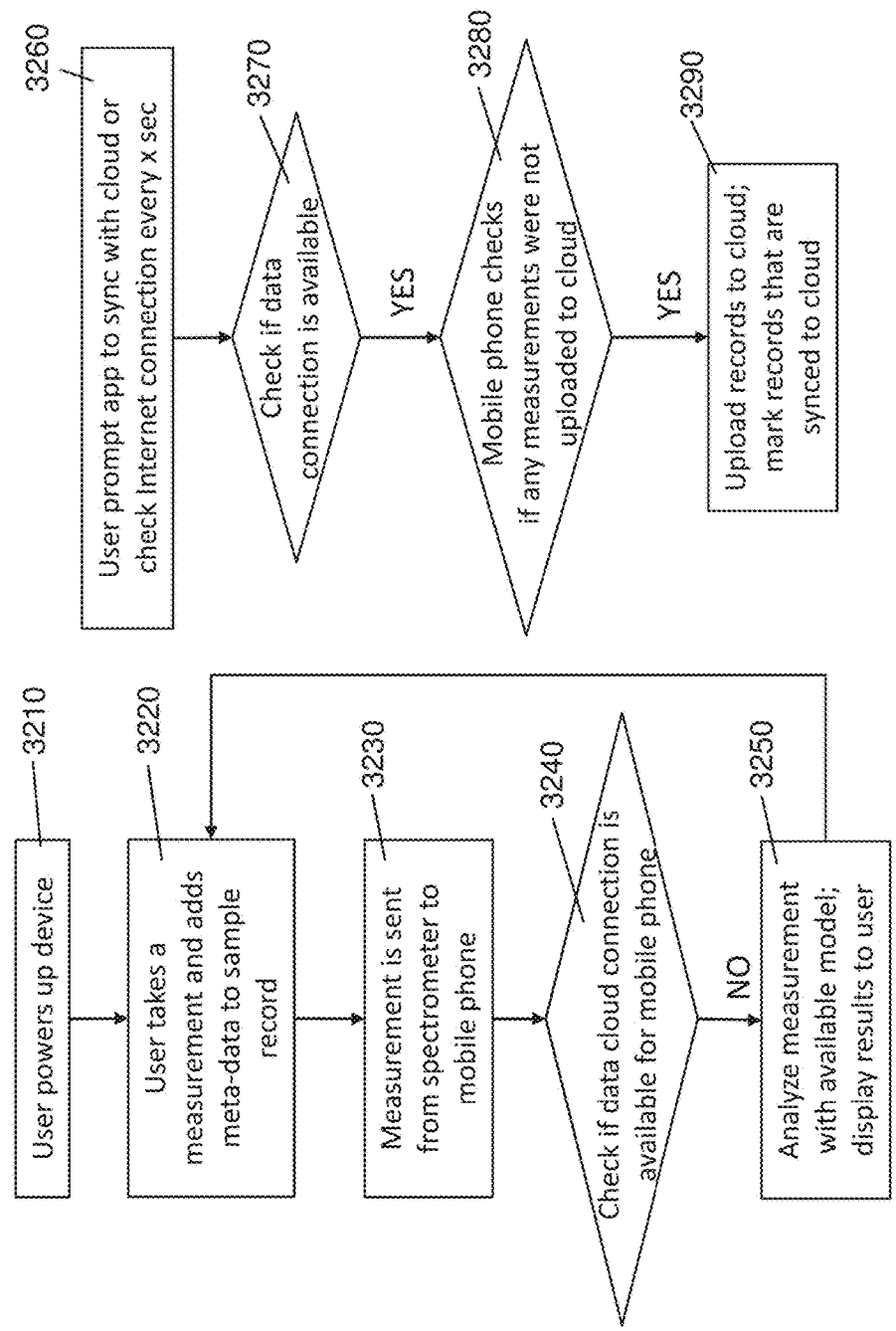
FIG. 32 shows a schematic diagram of an off-line mode of operation of compact spectrometer for developers.

FIG. 32 shows a schematic diagram of an off-line mode of operation of compact spectrometer 102 for developers. Users may be interested in developing applications for the spectrometer system, such as system databases, analysis models or algorithms, or the user interface. The spectrometer system may be configured to facilitate data collection and upload for developers when the spectrometer system does not have access to an internet connection. At step 3210, the spectrometer 102 may be powered up, and then used to measure the spectra of a sample material or object at step 3220. At this time, the user may also add meta-data to the sample measurement, such as time, location, or physical properties of the sample material. At step 3230, the measurement data, which may comprise the metadata in addition to the compressed and encrypted raw data signal 410 as shown in FIG. 16, may be transmitted from the spectrometer 102 to the hand-held device 110 such as a mobile phone. The raw data may be analyzed locally by a data analysis model or algorithm developed by the user. At step 3240, the hand-held device 110 may then check if connection to the cloud server 118 is available. If the hand-held device is unable to access the cloud server 118, at step 3250, the sample measurement data may be stored locally, for example in a memory of the hand-held device 110, and marked for later upload to the cloud server. At step 3260, the user may prompt the user interface (e.g., a mobile app) of the hand-held device to check internet connection or synchronize with the cloud server 118 at regular intervals, for example every few seconds. At step 3270, the user interface may check whether connection to the cloud server is available. If connection is available, at step 3280, the user interface may be configured to check whether there is any locally stored measurement data that has not yet been uploaded to the server. If such data is detected, at step 3290, the sample measurement data may be uploaded to the cloud server 118, where the data may be added to the universal database in the cloud as described in further detail herein. Once uploaded to the server, the locally stored measurement data may be marked accordingly.

User Interface

The spectrometer system 100 is typically provided with a user interface (UI) that provides a means for users to interact with the spectrometer system. The UI is typically provided on a display of the hand held device 110 of the spectrometer system, the hand held device comprising a processor that comprises instructions for providing the UI to the display, for example in the form of a mobile application. The display can be provided on a screen. The screen may comprise a liquid crystal display (LCD) screen, an LED screen, and/or a touch screen. The UI is typically presented to the user via a display of the hand held device 110, and is configured to receive input from the user via an input method provided by the hand held device 110.

Figure 19:
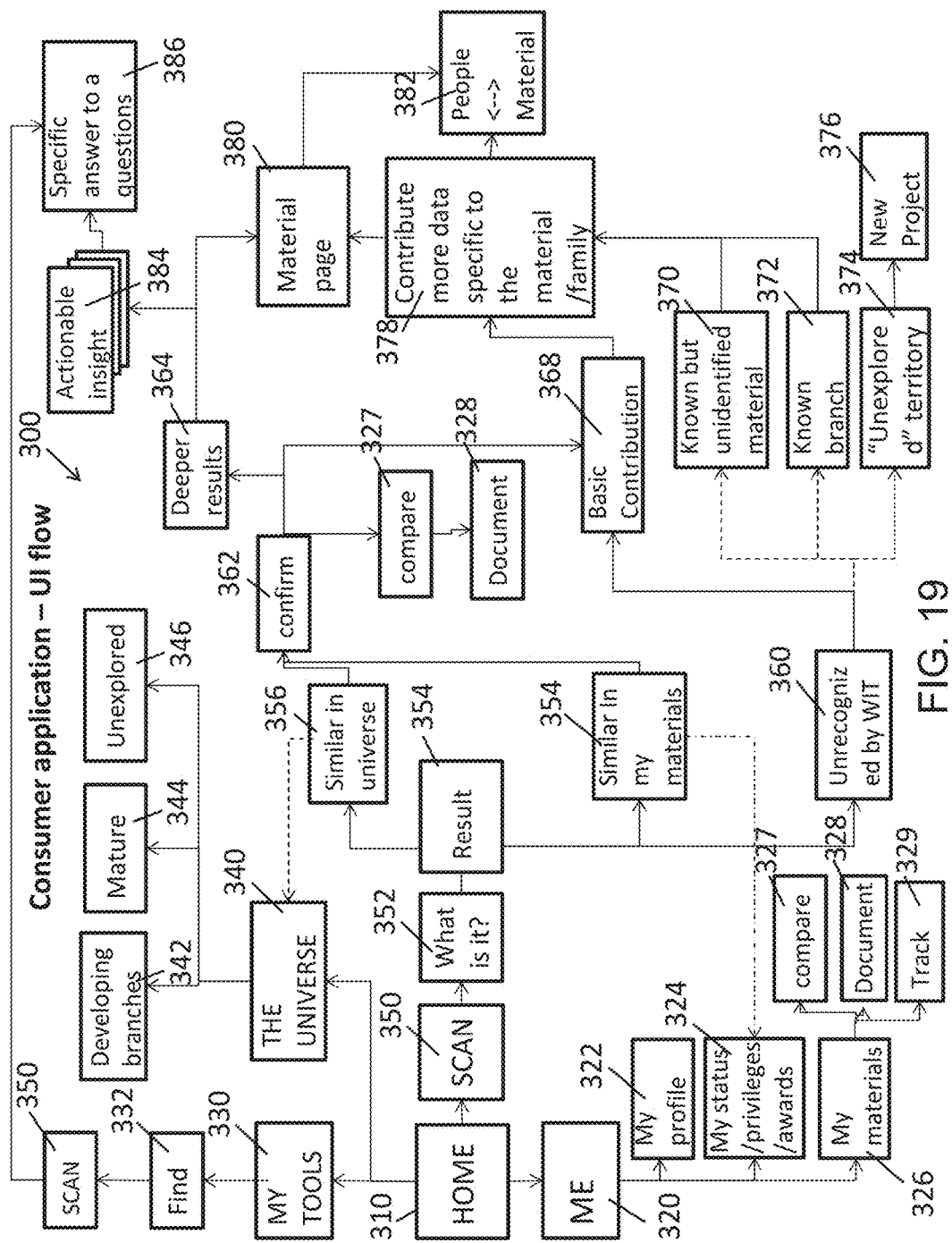
FIG. 19 shows a schematic diagram of the flow of the user interface (UI), in accordance with configurations.
Figure 20:
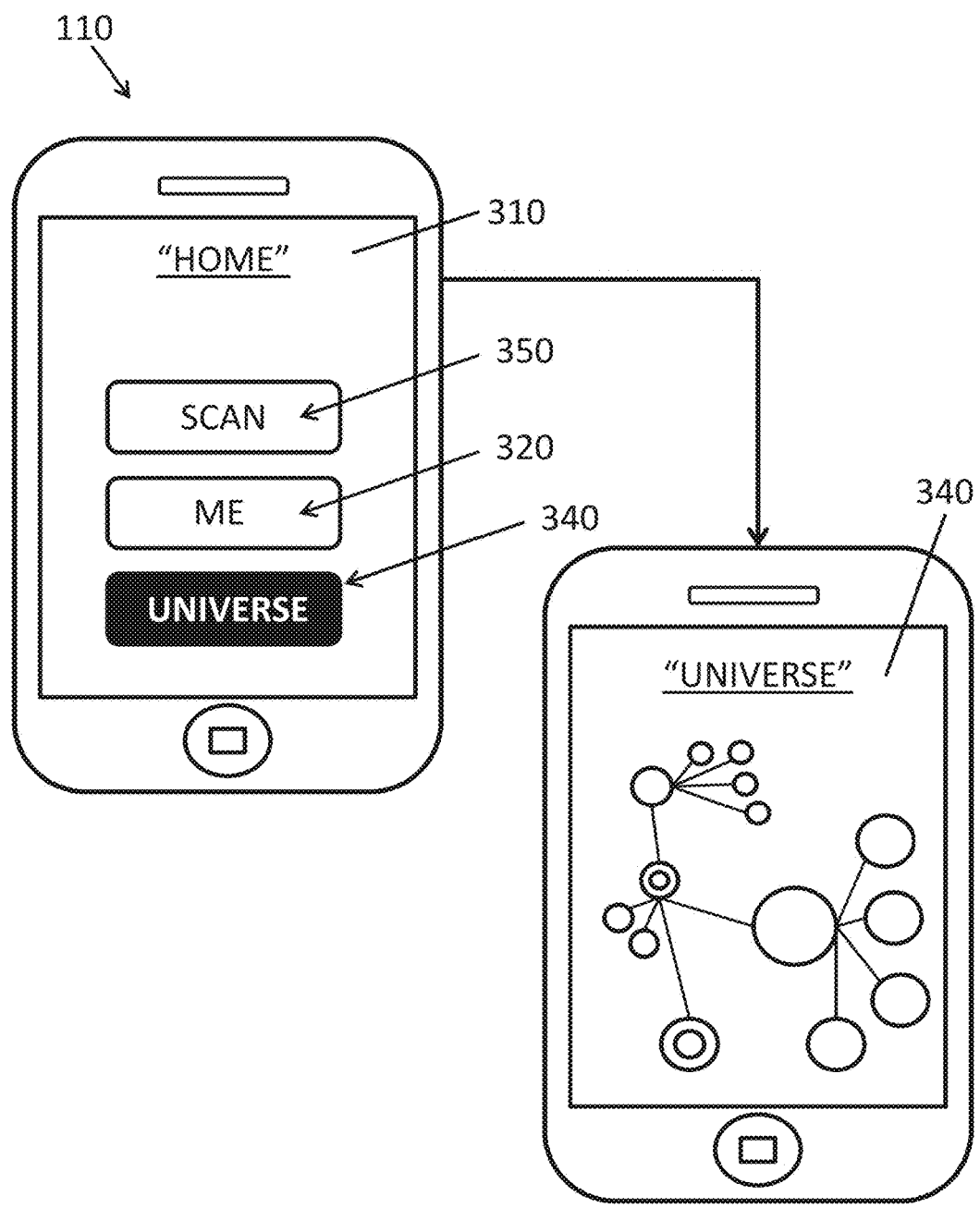
FIG. 20 illustrates an example of how a user may navigate through different components of the UI of FIG. 19.

FIG. 19 shows a schematic diagram of the flow of the user interface (UI) 300. The UI typically comprises a plurality of components as shown in FIG. 19, wherein each UI component may comprise a step of a method for the processor of the hand held device to provide the computer interface. The user may navigate through each component of the UI, wherein each component may have one or more corresponding screens configured to display user-selectable options, take user inputs, and/or display outputs of user-initiated actions (e.g., analyzed data, search results, actionable insights, etc.). A user-selectable option within a UI component may include an analysis identifier, such as an image or text, or an icon associated with a spectroscopic analysis application. When a user selects a user-selectable option within a UI component, for example, by touching the icon for a particular option, the processor providing the UI may carry out a set of instructions associated with the user-selected option. As a result, the UI may be directed to a new screen associated with a component of the UI related to the user-selected option. FIG. 20 illustrates an example of how a user may navigate through different components of a UI. In this example, the user begins from the screen of the UI associated with the component "Home" 310, described in further detail herein, as shown on the left. From "Home" 310, the user selects the option "Universe", which is associated with the component "Universe" 340 of the UI. As a result, the UI directs the user to the screen associated with the "Universe" 340 component, as shown on the right.

A person of ordinary skill in the art will recognize variations and adaptations that may be made to the UI flow as shown in FIG. 19, including, but not limited to, the removal or addition of one or more components, one or more components arranged in a different order, and/or one or more components comprising subcomponents of other components. One or more of the processors as described herein may comprise a tangible medium embodying instructions to provide one or more of the components of the user interface or to implement the method of the computer interface, and combinations thereof.

Figure 21A:
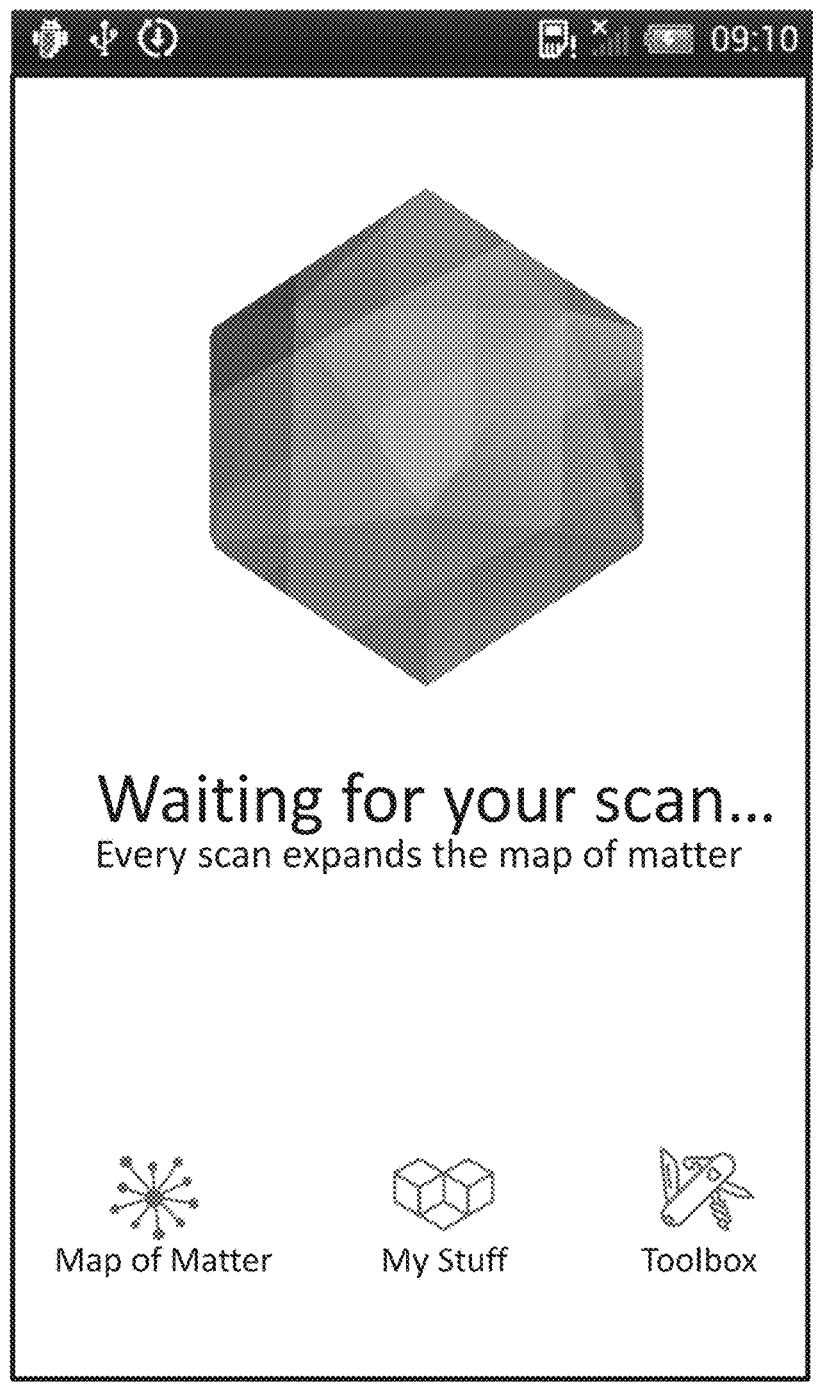
FIG. 21A shows an exemplary mobile application UI screen corresponding to a component of the UI of FIG. 19.

Typically, when a user opens the application providing the UI, the user is directed to the component "Home" 310. In the "Home" 310 component, the main action presented to the user may be an invitation to scan a sample material, via the "Scan" 350 component. FIG. 21A shows an exemplary mobile application UI screen corresponding to the "Home" 310 component of the UI. "Home" 310 is also the entry point to the components "Me" 320, "My Tools" 330, and "Universe" 340. "Me" 320 provides access to private user information. "My Tools" 330 provides access to personalized tools for scanning and analyzing materials. "Universe" 340 provides access to information in the universal database 119 operated by the cloud server 118 as described herein.

"Me" 320 may provide access to one or more of "My profile" 322, "My status/privileges/awards" 324, and "My materials" 326. "My profile" 322 may store a user's personal information, such as name and location, for example. "My profile" 322 can also store a user's personal settings for certain aspects of the system, such as privacy preferences, for example. "My status/privileges/awards" 324 may track a user's history of performing scans using the spectrometer system and contributing data to the universal database 119, for example. Based on the user's contribution to the universal database, the user may be given certain privileges, credits, or recognition, thereby providing an incentive for users to actively contribute data to the universal database. For example, "contribution scores" may be kept by the system for each user, and displayed under "My status/privileges/awards". Users may also be provided with a way of interacting with other users of the spectrometer system, either through "My status/privileges/awards" 324 or through a separate module. For example, users may be provided with a way of recommending/liking other users based on their contribution status, and such feedback from other users may be accessed via "My status/privileges/awards" 324 or another appropriate component. "My materials" 326 can allow users to view and compare data associated with their materials via the "Compare" 327 component. The scans performed by a user may be stored in "My materials" under a tag, and kept private or public (accessible by other users via the universal database 119) depending on user preference. "Compare" 327 can provide users with the ability to compare scans by tags, either across different tags or within a given tag. "My materials" 326 can also provide users with the ability to document their projects via the "Document 328" component, for example by adding notes or image data associated with a material. "My materials" 326 can also provide users with the ability to track their projects via the "Track" 329 component, wherein, for example, the UI may display a complete, sortable and/or searchable list of projects for the user. Scan data that users choose to store in the public domain may be accessed by other users of the system, and "Track" 329 may also provide a way for a user to track other users' projects.

"My tools" 330 can provide quick access to personalized tools for scanning and analyzing materials that may be initiated directly without going through the "Scan" 350 component. A user may directly build and save a specific analysis (e.g., if the user is interested in using the spectrometer to determine the percent fat in cheese, he/she may set up such an analysis by identifying the material and the parameter of interest for the analysis). Alternatively or in combination, once a user has used the spectrometer to perform scans, the user may be given the option of storing favorite tools/analyses. Alternatively or in combination, the system may automatically store frequently used tools/analyses for access under "My tools". "Find" 332 can provide users with a way of searching for a desired analysis tool among stored tools. "My tools" may also be configured to notify users about new tools that are made available by the system. Once a user selects a desired analysis method from the component "Find" 332, the user may be invited to initiate a scan through the UI component "Scan" 350, described in further detail herein. However, since the analysis method has already been selected, "Scan" 350 may be configured to skip over some intermediate steps (e.g., identification of the material), and proceed directly to displaying the answer to the user's query through the component "Specific answer to a question" 386.

"Universe" 340 can give users access to the universal database 119 operated by the cloud server 118, wherein spectral signatures of materials are stored for comparison against and analysis of scanned data. "Universe" 340 may be displayed as a graphical map, providing users with a generic visualization of the map of matter by different attributes. For example, the map may be organized by geographic, material, gender, maturity, or "popularity" attributes. A user may be able to zoom in and out of the map to get to a specific material page. The map of matter for a specific material may be visualized based on one or more of a geographical location, time/date, store/branch, type of object, temperature, number of measurements, and many other factors. Different types of materials in the map may develop at different paces, resulting in different "maturity" levels over time; accordingly, the visualization of the branches of the map may differ based on this maturity level. "Universe" 340 can thus provide users with a way to viewing the map through three separate UI components, "Developing branches" 342, "Mature" 344, and "Unexplored" 346, which may display different types of information, display the map using different visualizations, and/or present different user-selectable options. The map of matter may highlight a user's own contributions to the map in the display, so that the user may be able to visualize his/her scans in the context of the map. Users may be given the ability to search for material "soul mates" (e.g., materials having similar spectral signatures), or track down "experts" in a certain material branch by identifying users who have made significant contributions to a branch of interest. "Universe" 340 may also provide users with notifications regarding materials that the user is interested in, such as new contributions/map progress made on certain materials. Users may be given a way to set up "campaigns" to foster maturity of a certain branch in the map of matter, and the "Universe" may also send users notifications regarding such campaigns.

An exemplary workflow for scanning a material with the spectrometer system is now described with reference to FIG. 19. A user may initiate a scan from the screen corresponding to the UI component "Home" 310, such as the one shown in FIG. 21A, by pressing a button on the spectrometer or on the mobile application presenting the UI. When a scan is initiated, the UI directs the user to the screen corresponding to the component "Scan" 350, which may instruct the spectrometer to begin a measurement, compress and encrypt the raw data, and/or transmit the compressed and encrypted data to the UI of the hand held device.

When data is received by the UI, the UI may initiate the "What is it?" (WIT) 352 component, which may comprise the system's main classification algorithm. The main classification algorithm may, for example, attempt to determine the material's identity based on the spectrum of the material, by comparing the spectrum against the spectra of known materials stored in the user's personal database stored under the "My Materials" component and/or the universal database 119. The algorithm may yield three different results: the identification of similar spectra in the "Universe" database, the identification of similar spectra in the "My Materials" database, or a failure to find any matching spectra in either database. The outcome of the algorithm run by the "What is it?" 352 component may be presented to the user via the "Result" 354 component, wherein the user may view the preliminary identification results and provided with a range of selectable options for further actions, as described herein for each possible outcome.

If one or more similar materials are identified in the "Universe" database, the user may be directed to the screen corresponding to the UI component "Similar in universe" 356. From here, the user may be given the option to view the data relevant to the material in the universal database 119, directing the user to the UI component "Universe" 340. Alternatively, the user may be asked to confirm that the material indeed matches the identified material(s), through the UI component "Confirm" 362. If the system has found a plurality of materials with spectra similar to the sample, the user may be asked to select one or more of these "matching" materials for further analysis.

If one or more similar materials are identified in the "My materials" database, the user may be directed to the "Similar in My Materials" 355 component of the UI. From here, the user may choose to navigate to the "My status/privileges/awards" 324 component or the "My materials" 326 component, where the user may view and compare data associated with their materials. Alternatively, the user may be asked to confirm that the material indeed matches the identified material(s), through the UI component "Confirm" 362.

Figure 21B:
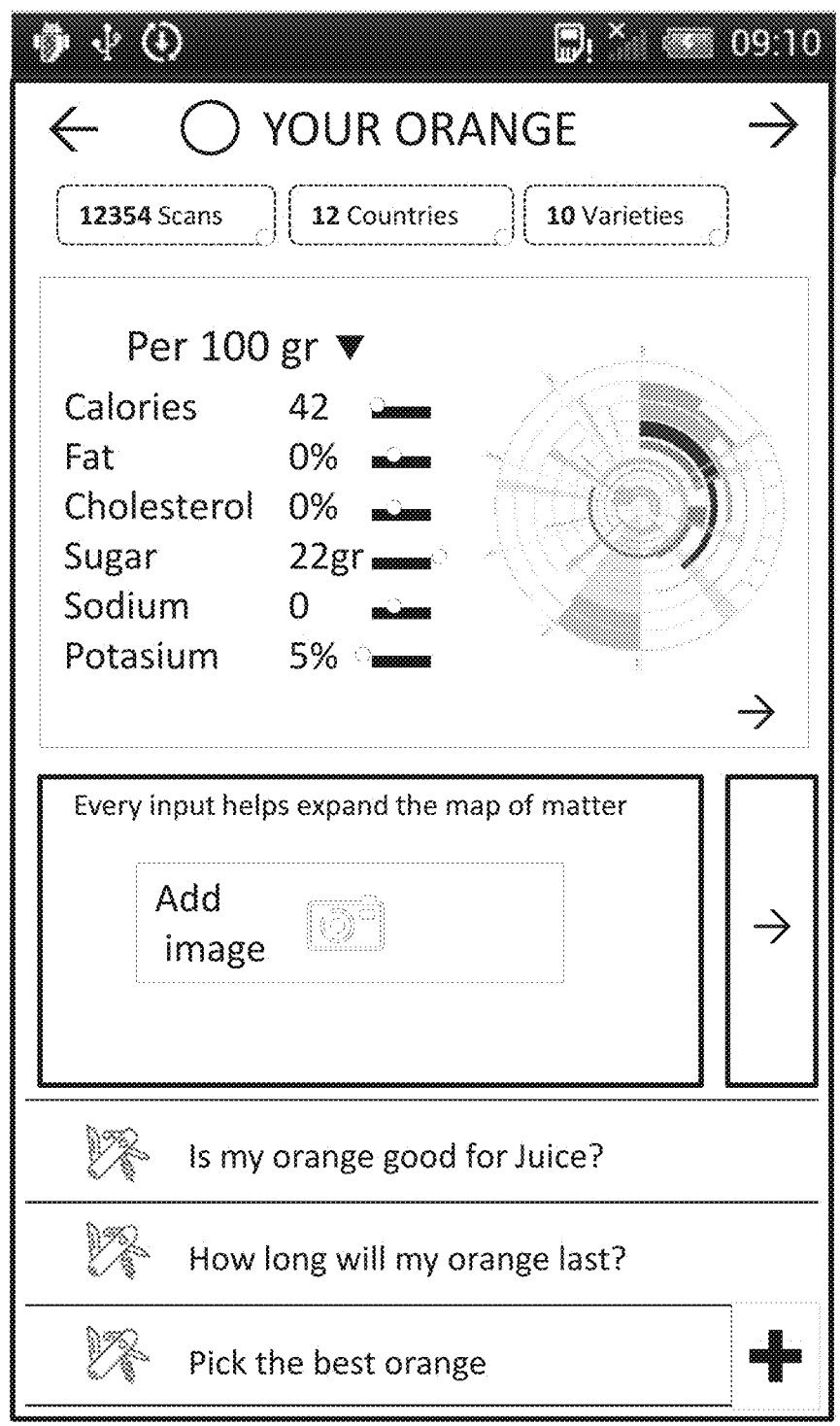
FIGS. 21B and 21C show an exemplary mobile application UI screen corresponding to components of the UI of FIG. 19.

If the identity of the measured material is positively confirmed by the user, the system may initiate the "Compare" 327 component to allow users to view and compare data associated with their material. The user may also document the results of the scan through the "Document" 328 component of the UI, which provide users with the option of adding notes or other miscellaneous data relating to the measurement. For example, as shown in FIG. 21B, an image of the measured material may be added, wherein the image may be acquired by an image capture device integrated with, or separate from but in communication with, the spectrometer system. The UI may also present users with the option of running further analyses of the material, through the UI component "Deeper results" 364. Further analyses may include, for example, analyses of specific nutritional attributes of a food item (e.g., percentage of fat/carbohydrates/protein, number of calories), specific contribution of a pharmaceutical product, or attributes of a plant (e.g., water content). The user may be given the option of selecting one or more types of analysis, for example by searching through a list of available analyses for the confirmed material. Alternatively or in combination, the system may automatically select one or more appropriate analysis tools, based on the identity of the material. For example, the system may further comprise an image capture device such as a camera, and may be configured to receive image data acquired by the image capture device, to use at least a portion of the image data in automatically selecting the appropriate analysis tools. In order to aid in the automatic selection of the analysis tool, a processing device of the spectrometer system may be configured to recognize a characteristic of the material based on the image data. In configurations where two or more different types of analyses are selected, the selection of the analysis types may be based on a predetermined hierarchy.

Figure 21C:
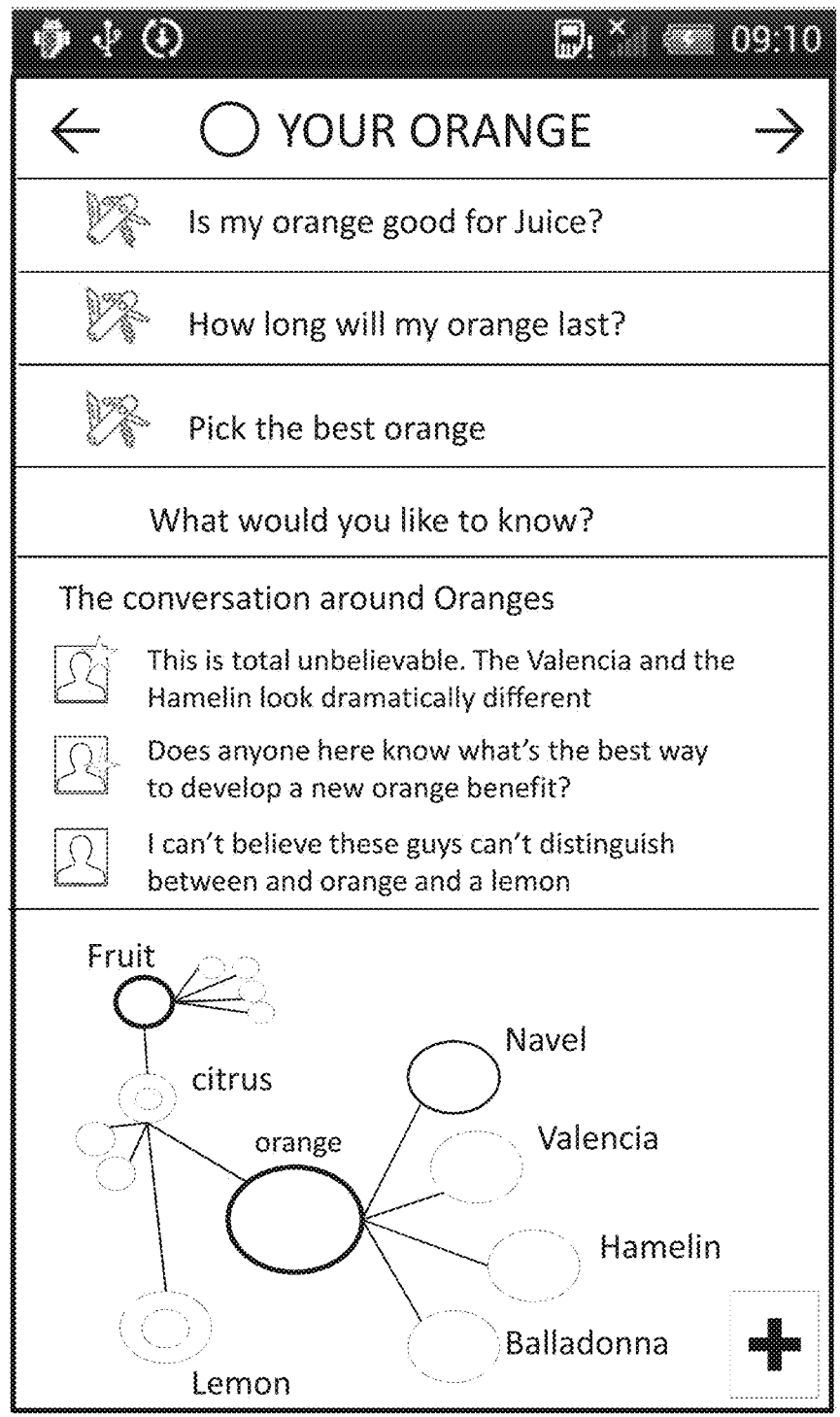

Once further analyses are completed, the UI can display the data for the measured material through the "Material page" 380 component of the UI. The UI may optionally provide the user with actionable insight via the "Actionable insight" 384 component. FIGS. 21B and 21C show an exemplary mobile application UI screen corresponding to the "Material page" 380 and "Actionable insight" 384 components of the UI (FIG. 21C shows the screen of FIG. 21B scrolled down). As shown in FIG. 21B, the UI may display results of the analysis, such as the identity and nutritional content analysis of the material; some additional parameters that may be displayed in the results include an image of a material, a freshness of a material, and a textual description of a material. A visual representation of the spectral data may also be displayed to the user. The display of results may also include a visualization of the map of matter of the component "Universe" 340. The UI may also provide the users with a way of connecting with other users interested in the measured material, through the "People↔Material" 382 component. For example, the component may enable users to participate in social messaging as shown in FIG. 21C, fostering conversations among system users related to the identified material.

The "Actionable insight" 384 component may provide users with the option of selecting one or more specific questions related to the measured material, such as those shown in FIG. 21C, whose answer may provide an insight that can be used as basis for taking a certain course of action. For example, if the identified material is an apple with a relatively high sugar content, the UI may inform the user that the user should select/consume the apple if the user desires a sweet fruit, or, conversely, that the user should not select/consume the apple if the user has a condition, such as diabetes, that would make the high sugar content an attribute that should be avoided. The UI may, optionally, have the ability to store personal data such as certain conditions and/or preferences, such that the UI may automatically select and display the most appropriate actionable insight for the specific user. The answer or actionable insight may be provided to the user via the "Specific answer to a question" 386 component. The component 386 may also be directly accessible via the "My Tools" 330 component, wherein a specific analysis method may be chosen prior to initiating a scan, and the user can directly obtain an answer or actionable insight to a specific question regarding a specific material.

Sometimes, the component "Confirm" 362 may not yield a positive confirmation by the user. If the identity of the measured material does not actually match the material(s) that the system has found to be a "match", the user may be prompted to provide basic information regarding the measured material, through the component "Basic contribution" 368. Once the basic identity of the material has been provided, users may optionally be asked to contribute additional data, through the component "Contribute more data specific to the material/family" 378. Users may, for example, contribute metadata such as physical properties of the material, or image data. From here, users may be directed to "Material page" 380 where they may view information regarding the material of interest, and/or users may participate in social conversations/interactions with other users of the system via the component "People↔Material" 382.

When a user generates spectral data through the "Scan" 350 component or contributes non-spectral data through the "Basic contribution" 368 and/or "Contribute more data" 378 components, the data may be added to the universal database 119. Data may be automatically added to the universal database 119, while giving the user the option to keep the contribution "private" (not accessible by other users of the system). Any data generated or contributed by a specific user may also be added to the user's personal database of materials stored in the "My Materials" component. Data in a user's personal database may be configured to be kept private or to be shared with other users of the system. Alternatively, some of the data in the personal database may be kept private, while some may be shared with other users.

In order to maintain the integrity and validity of the data contained in the universal database, a system check may be implemented before the database is updated with the data from a scan. The system check may be initiated, for example, at the "Document" 328 component (where newly generated spectral data is added to the database), or at the "Basic Contribution" 368/"Contribute more data" 378 component (where user-contributed non-spectral data is added to the database). The system check may, for example, comprise an outlier detection algorithm, wherein data for the relevant material family is sorted, and the new data point is compared against the existing data to verify the validity of the new data point (e.g., whether the new data point falls within a specified standard deviation from the average of the existing data points). Any data point identified as an "outlier" may be held back from being added to the database, and/or "quarantined" in a location separate from the universal database. An "outlier" may comprise, for example, a data point for a known material that differs significantly from the mean data for the material, or any data point for a previously unrecognized material/spectrum. A quarantined "outlier" data point may eventually be added to the universal database, as data points previously recognized as outliers may become recognized as valid as the size and breadth of the universal database grows over time. The system check for verifying the validity of new data may also be based on one or more conditions associated with collection of the acquired light spectrum, including at least one of a temperature, a geographic location, a category of a material, a type of a material, a chemical composition, a time, an appearance of a material, a color of a material, a taste of a material, a smell of a material, and an observable characteristic associated with a material.

After performing a scan through the "Scan" 350 component, the system may fail to find a match for the measured material's spectrum, in either the "Universe" database or the "My materials" database. In this case, the "Unrecognized by WIT" 360 component of the UI may be initiated. The user may be directed to the "Basic contribution" 368 component of the UI, described in further detail herein, where the user may be asked to contribute basic identity information (if known) regarding the sampled material. If the sampled material is a known material with a previously unidentified spectrum, the UI may initiate the "Known but unidentified material" 370 component, wherein the user may be asked to contribute additional data relating to the material via the "Contribute more data" 378 component. If the sampled material is a known material belonging to a known branch of the map of matter, the UI may initiate the "Known branch" 372 component, wherein the user may be asked to contribute additional data relating to the material via the "Contribute more data" 378 component. If the sampled material is a completely unknown material that doesn't appear to belong to any known branches comprising classes of classifications of the map of matter, the UI may initiate the "Unexplored territory" 374 component. The "Unexplored territory" 374 component may direct the UI to run the "New project" 376 component, which can create a new, exploratory branch in the map of matter (e.g., under the "Unexplored" 346 component of the "Universe" 340). The "Unexplored territory" 374 component may prompt the user to contribute as much information as possible regarding the material, including images and/or textual descriptions of the material.

The UI may further be configured to track user preferences and provide recommendations based on acquired light spectra. For example, a user may scan a product to obtain a light spectrum, and based on the spectrum and/or pre-stored user preference data, the system may send the user a recommendation about the scanned product. The universal database may be configured to store spectroscopic data and associated preference data for each system user, and a processing device of the system may be configured to receive a recommendation request from a device associated with a user, and generate and provide a recommendation based on the analyzed data. The processing device of the system can be configured to receive and process update requests for user preference settings. For example, a user may set his/her preferences regarding product tracking and recommendation functions through the "Me" component of the UI.

The UI may further provide means for supporting applications development by users, in order to encourage user involvement in developing and improving the system databases, algorithms, and/or user interface.

The UI may provide support for chemometric applications development, for example, for users/developers who are interested in developing new models, analysis algorithms, and/or databases of the materials they want to support in their applications. Developers may first collect relevant samples and measure them using the spectrometer system disclosed herein. Developers may then create a model or algorithm using a set of algorithms provided by the spectrometer system's infrastructure. Developers can test their model and see how well it functions, and then correct it to get optimal results. Once the model development is completed, developers can "publish" their model on the spectrometer system's infrastructure and allow other users to use the model. Users may use the model as part of the spectrometer system's mobile application, or developers may also develop their own mobile application that can run the developed model. If developers choose to develop their own mobile application, the newly created mobile application may communicate with the spectrometer system's infrastructure to run the model.

The UI may also provide support for mobile applications development, for users/developers who are interested in using the existing database structure and analysis algorithms to build new mobile applications. Developers may take advantage of existing chemometric applications and/or models to create a new user interface and a new user experience, possibly with new related content. Developers may "publish" their new mobile application on the spectrometer system's infrastructure, allowing others to access and use their mobile app.

The UI may also provide an option for researchers ("Researcher Mode"), where researchers are provided with the ability to generate their own database, then download the raw data of the database for their own use, outside of the spectrometer system's infrastructure. Such an option can provide researchers with maximum flexibility in handling data.

FIGS. 22A-22F show a method 500 for the processor of a hand held device to provide the user interface 300 for the spectrometer system, as described herein.

Figure 22A:
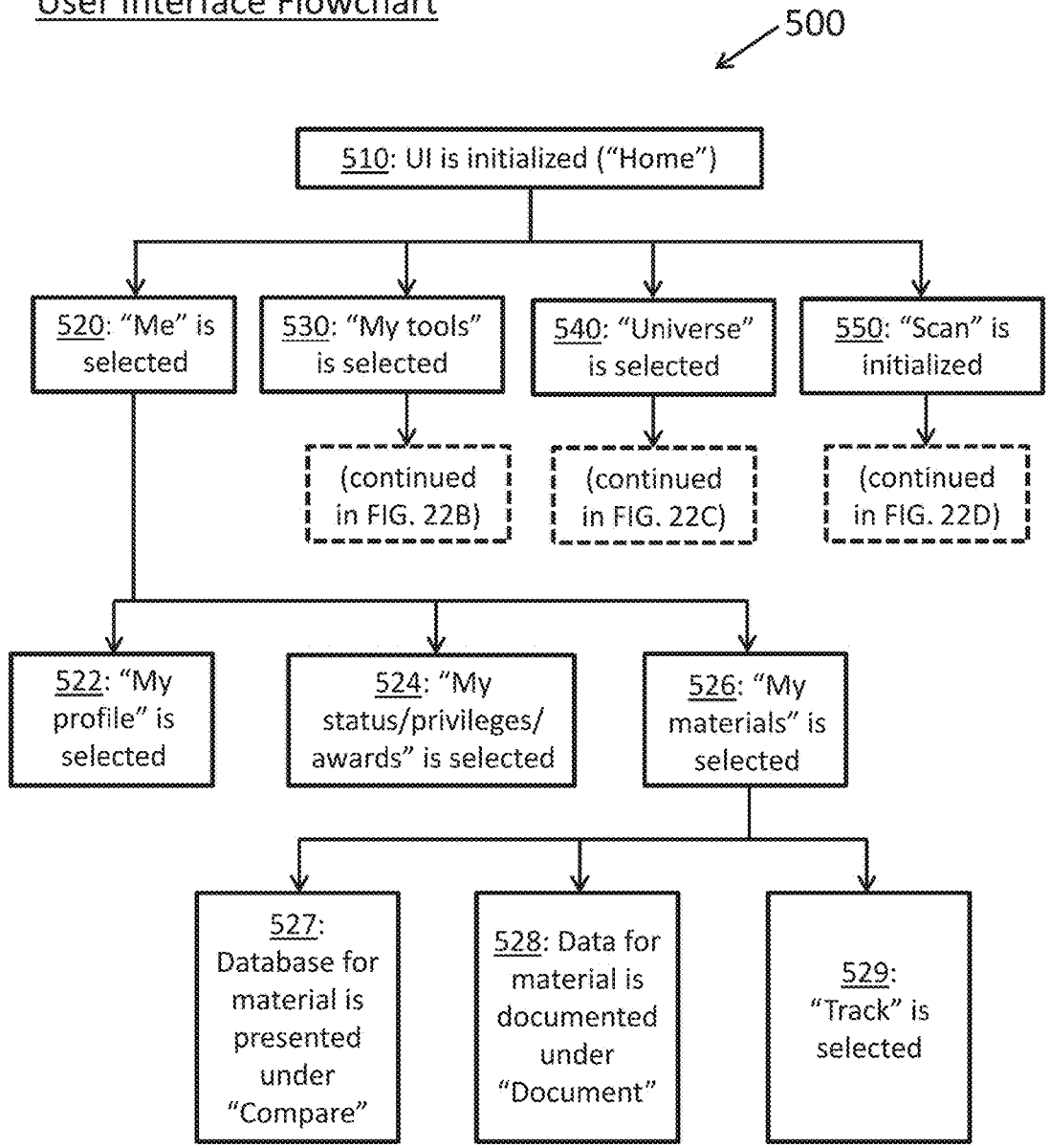
FIGS. 22A-22F show a method for a processor of a hand held device to provide the user interface of FIG. 19, in accordance with configurations.

Referring to FIG. 22A, at step 510, the UI is initialized, for example by a user starting a mobile application providing the UI, and the "Home" 310 component is presented to the user as described herein. The "Home" 310 component may present the user with the options of selecting one of "Me", "My Tools", "Universe", or "Scan".

At step 520, "Me" is selected from step 510, and the user is directed to the "Me" 320 component of the UI, as described herein. "Me" 320 may provide access to one or more of "My profile" 322, "My status/privileges/awards" 324, and "My materials" 326. At step 522, the "My profile" 322 component is executed, as described herein. At step 524, the "My status/privileges/awards" component 324 is executed, as described herein. At step 526, the "My materials" 326 component is executed, as described herein. "My materials" 326 may provide access to one or more of "Compare" 327, "Document" 328, or "Track" 329. At step 527, the "Compare" 327 component of the UI is executed, as described herein. At step 528, the "Document" 328 component of the UI is executed, as described herein. At step 529, the "Track" 329 component of the UI is executed, as described herein.

Figure 22B:
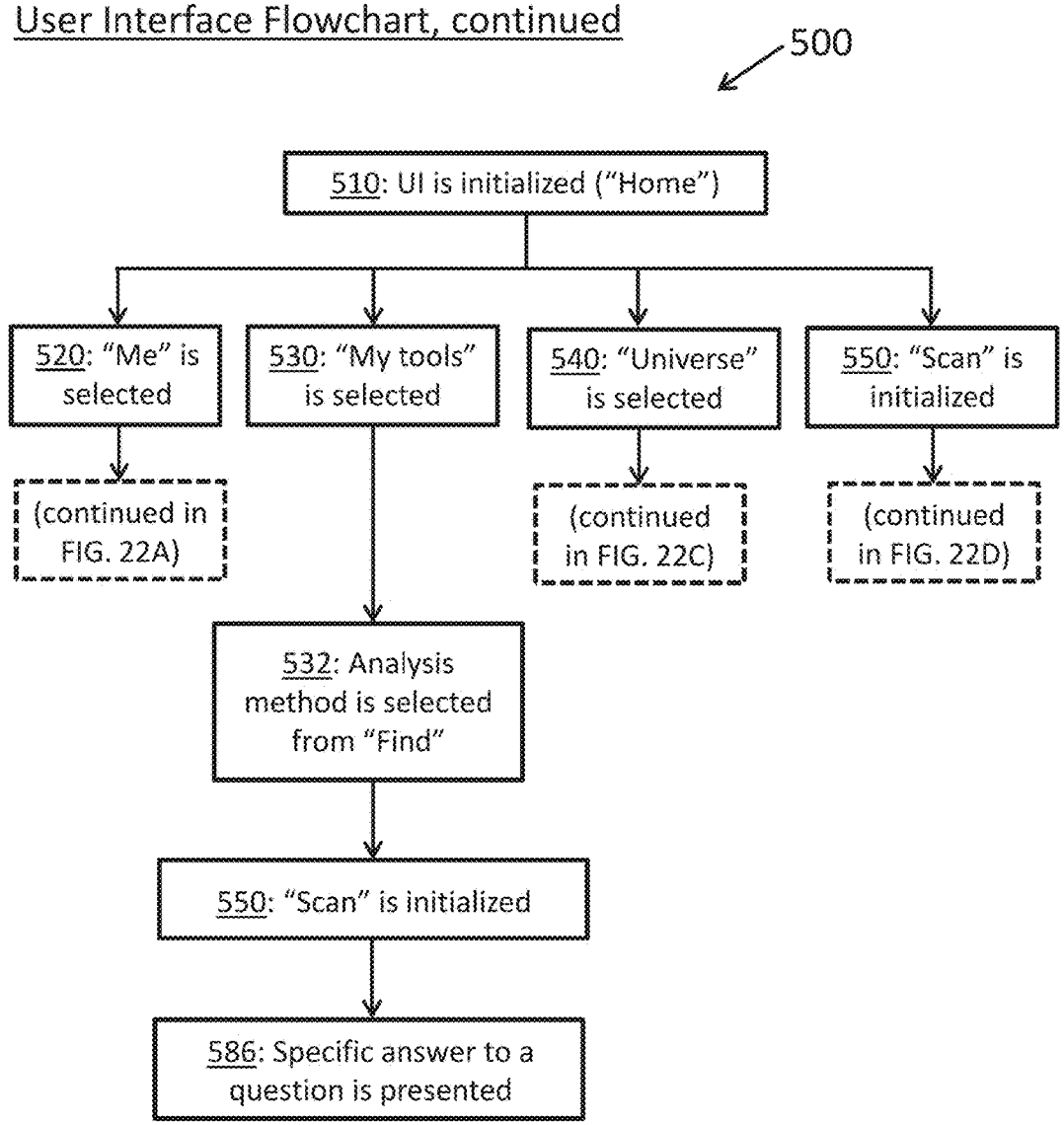

Now referring to FIG. 22B, at step 530, "My Tools" is selected from step 510, and the user is directed to the "My tools" 530 component of the UI, as described herein. At step 532, an analysis method is selected by the user from the UI component "Find" 332, as described herein. At step 550, the "Scan" 350 component of the UI is executed, as described herein, using the analysis method selected at step 532. At step 586, the "Specific answer to a question" 386 component of the UI is executed as described herein, wherein the user is presented with an actionable insight.

Figure 22C:
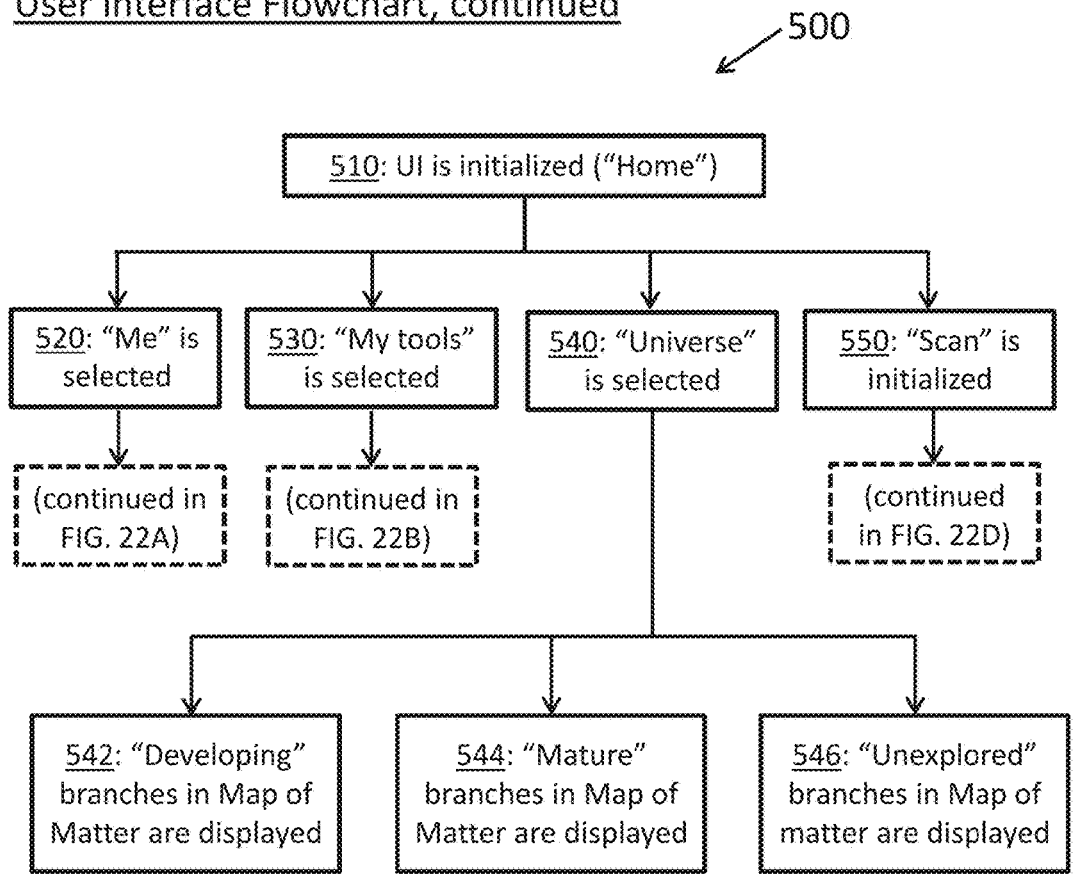

Now referring to FIG. 22C, at step 540, "Universe" is selected from step 510, and the user is directed to the "Universe" 340 component of the UI, as described herein. At step 542, the "Developing branches" 342 component is executed, as described herein. At step 544, the "Mature branches" 344 component is executed, as described herein. At step 546, the "Unexplored branches" 346 component is executed, as described herein.

Figure 22D:
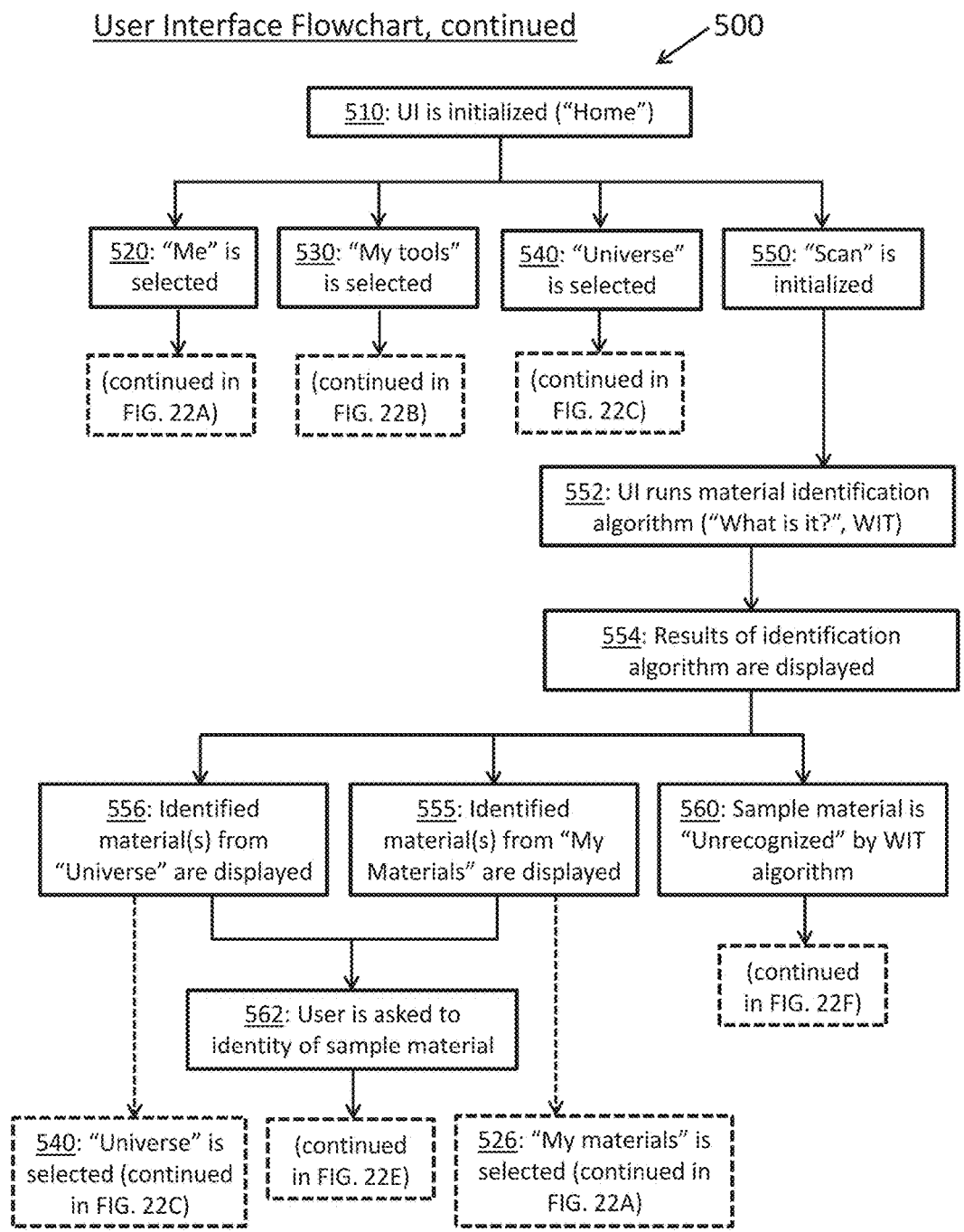

Now referring to FIG. 22D, at step 550, "Scan" is selected from step 510, and the user is directed to the "Scan" 350 component of the UI, as described herein. At step 552, the "What is it?" 352 component is executed, as described herein. At step 554, the "Result" 354 component is executed, as described herein. "Result" 354 may provide access to one or more of "Similar in universe" 356, "Similar in my materials" 355, or "Unrecognized by WIT" 360. At step 556, the "Similar in universe" 356 component is executed, as described herein, wherein the user may be provided with the option of selecting between "Universe" 340 and "Confirm" 362. At step 555, the "Similar in my materials" 355 component may be executed, as described herein. At step 555, the user may be provided with the option of selecting between "My materials" 326 or "Confirm" 362. At step 560, the "Unrecognized by WIT" 360 component of the UI is executed, as described herein.

Figure 22E:
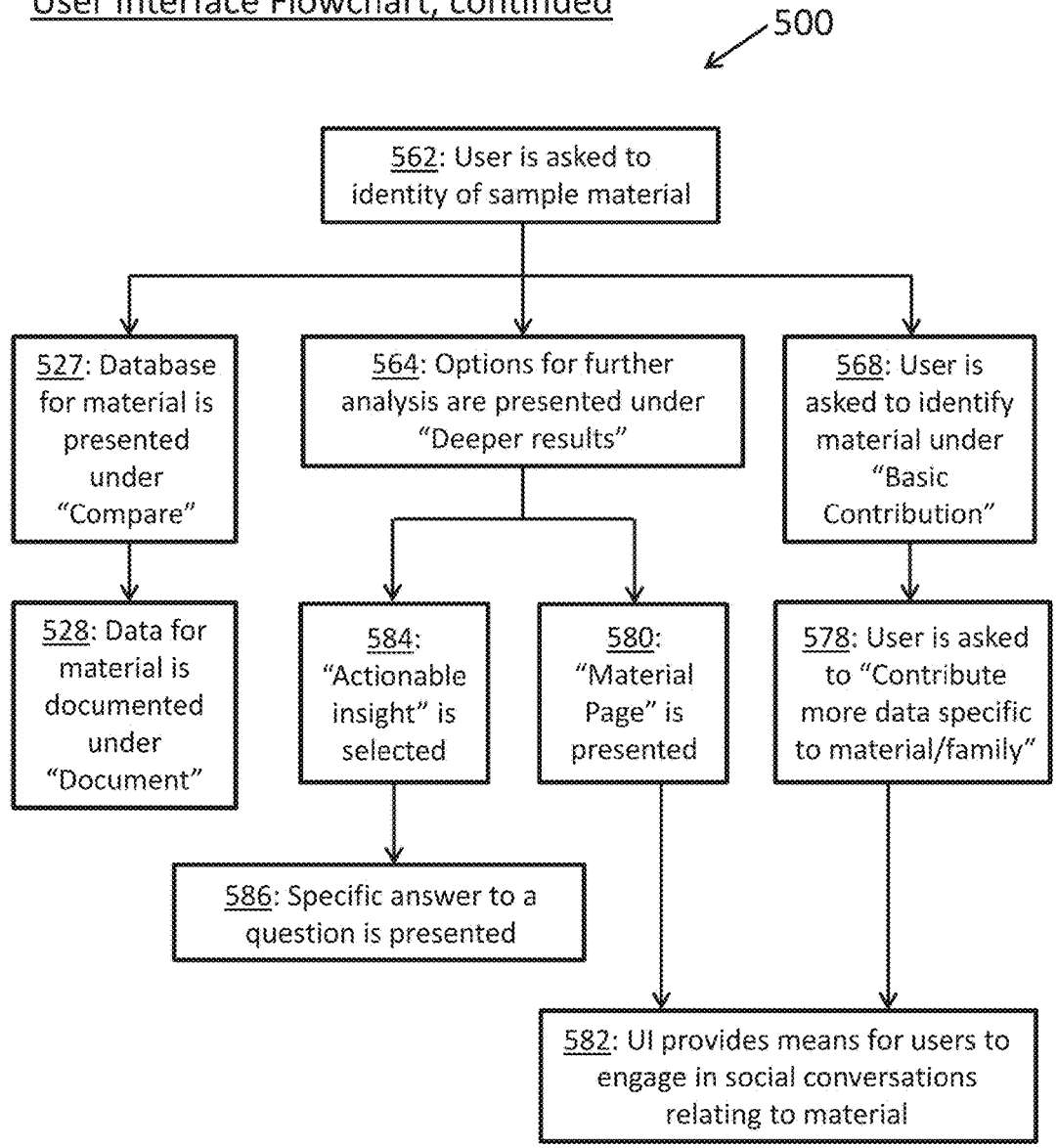

Now referring to FIG. 22E, at step 562, the "Confirm" 362 component of the UI is executed. At step 562, the user may be provided with the option of selecting one or more of "Compare" 327, "Deeper results" 364, or "Basic contribution" 368. At step 527, the "Compare" 327 component of the UI is executed, as described herein. At subsequent step 528, the "Document" 328 component of the UI is executed, as described herein. At step 564, the "Deeper results" 364 component of the UI is executed, as described herein. At step 564, the user may select between "Material page" 380 or "Actionable insight" 384. At step 584, the "Actionable insight" 384 component of the UI is executed, as described herein. At subsequent step 586, the "Specific answer to a question" 386 component of the UI is executed, as described herein. At step 580, the "Material page" 380 component of the UI is executed, as described herein. At subsequent step 582, the "People↔Material" 382 component of the UI is executed, as described herein. At 568, the "Basic contribution" 368 component of the UI is executed, as described herein. At step 578, the "Contribute more data specific to the material/family" 378 component of the UI is executed, as described herein. Subsequent to step 578, the user may be directed to step 582, as described herein.

Figure 22F:
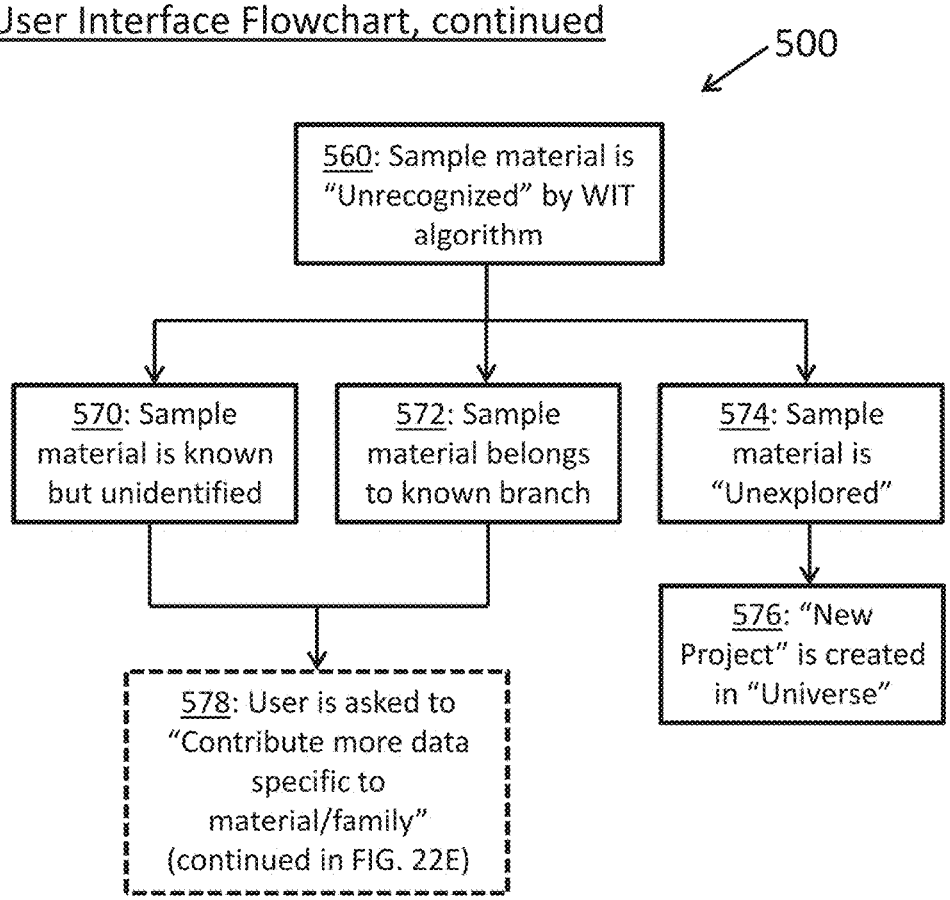

Now referring to FIG. 22F, at step 560, the "Unrecognized by WIT" 360 component of the UI is executed. At step 560, the user may be directed to one of the UI components "Known but unidentified material" 370, "Known branch" 372, or "Unexplored territory" 374. At step 370, the "Known but unidentified material" 370 component of the UI is executed, as described herein. At step 372, the "Known branch" 372 component of the UI is executed, as described herein. Subsequent to steps 370 or 372, the user may be directed to the component "Contribute more data" 378 in step 578, as described herein. At step 574, the "Unexplored territory" 374 component of the UI is executed, as described herein. At subsequent step 576, the "New project" 376 component of the UI is executed, as described herein.

Although the above steps show a method 500 of providing the UI 300 in accordance with configurations, a person of ordinary skill in the art will recognize many variations based on the teachings described herein. The steps may be completed in a different order. Steps may be added or deleted.

Some of the steps may comprise sub-steps of other steps. Many of the steps may be repeated as often as desired by the user.

Applications of the Compact Spectrometer System

The spectrometer system herein disclosed may be integrated into various devices and products across many industries. In order to facilitate the use of the system in various applications, the spectrometer system 100 may comprise a processor comprising instructions for performing various types of analyses for various applications. Some examples of these applications are described herein, but are in no way exhaustive.

Because of its small size and low cost, the spectrometer may be integrated into appliances commonly used in these various applications. For example, for food-related applications, the pocket size spectrometer may be integrated into kitchen appliances such as ovens (e.g. microwave ovens), food processors, and refrigerators. The user can then make a determination of the safety of the ingredients in real time during the course of food storage and preparation.

The spectrometer system disclosed herein may be used for agricultural applications. For example, the spectrometer system may be used to estimate the total solid solubles or "Brix" content in fruit. The pocket sized, hand-held spectrometer can easily be used to non-destructively measure the solid soluble content or water content of unpicked fruits, yielding information regarding the ripeness or firmness of the fruits. This will allow the farmer to monitor the fruits in a fast way and decide on appropriate picking time with no need to destroy products. Another example of an agricultural application for the spectrometer system is the field measurement of fertilization status of plants, such as grains, coffee, spices, oil-seeds, or forage. The hand-held spectrometer can be used to obtain information about the fertilization status of the plant by non-destructively measuring the near infrared (NIR) spectrum of the plant. The spectral signature of components such as nitrogen, phosphate, and potash can be analyzed to provide the fertilization status per plant. The spectrometer system may also be used for field measurements of plant status. A pocket-sized spectrometer can allow on-line in-field spectrum analysis of the different parts of the plants, and can be used for early detection of plants stress and diseases development. The spectrometer system may also be useful for providing soil analysis. Fast in-field analysis of the soil spectrum using the hand-held spectrometer may provide a tool to monitor fertilization, watering, and salinity of the soil in many points in the field. Such an analysis can provide a powerful decision tool for farmers. The spectrometer may also be used for analyzing milk, for example for analyzing the fat or melamine content of the milk.

The spectrometer system disclosed herein may be used for home gardening applications. For example, the spectrometer may be used to analyze the water content in leaves. The pocket-size spectrometer can be used to obtain the spectra of the leaves, and the spectral signature of water can be used to estimate the water content in the leaves. Such a tool can give the user a direct access to the plant's watering status. As discussed above, the spectrometer system may also be used to analyze soil. The spectral signature of water, nitrogen, phosphate, and potash, and other relevant soil components can be detected by a pocket size spectrometer. By scanning the soil with the spectrometer, the user may be able to estimate the watering and fertilization status of the soil.

The spectrometer system disclosed herein may be used for pharmaceutical applications. For example, the spectrometer system may be used to identify pills. Scanning medications with pocket size spectrometer can reveal the unique spectral signature that each medication has. The pill may be placed in a close and adjusted cave to enhance the signal that is reflected from it, and an analysis of the pill may be performed. The spectral signature of the pill can provide an exact and reliable way to identify the pill, thus helping to prevent confusion between similar medications and/or the use of counterfeit medications. Another example of a pharmaceutical application of the spectrometer system is the identification of active ingredients levels in Cannabis. The active ingredients (e.g., tetrahydrocannabinol (THC), cannabidiol (CBD)) of cannabis can impose unique features on the spectral range of both the wet (unpicked) inflorescence and on its dried form. Scanning the inflorescence with the hand-held spectrometer can provide a fast and accurate estimation of the content of the active ingredients in the inflorescence.

The spectrometer system disclosed herein may be used in food analysis applications. For example, the spectrometer may be used to obtain nutrient information of food. Fats, carbohydrates, water, and proteins have detectable spectral signatures. Scanning the food with a pocket size spectrometer, in tandem with on-line analysis of the spectrum, can provide an immediate way to get the food's macro-nutrients estimation, including accurate estimation of its caloric value. Another example of a food analysis application for the spectrometer system is oil quality assurance. Detecting changes of the spectrum of cooking oils by scanning the oils with pocket size spectrometer can give the users access to chemical changes of the oxidation and acidity levels of the oil. Analysis of these changes can provide an immediate and accurate oil quality measurement. The spectrometer system may also be used to monitor food quality. Bacterial by-products and enzymatic processes can leave chemical traces in the food, which may have unique spectral signatures. Analyzing these chemical fingerprints by scanning the food with pocket size spectrometer can be used to detect these changes and provide information on the food's quality. The spectrometer system can also be used to determine the ripeness of fruits. Enzymatic processes and changes in the water content can be detected by scanning a fruit with pocket size spectrometer, giving an accurate estimation of the fruit's ripeness level. The spectrometer system can also be used for gutter oil identification. The fatty acids composition (FAC) of oils determines the oils' spectra. Thus, the spectrum of an oil can be used to identify the FAC and by that to identify the type of the oil. In particular gutter oil can be identified as different types of edible oils. A pocket size spectrometer with on-line spectrum analysis can thus be used to detect and identify gutter oils. The spectrometer system may also be used to ensure food safety. The existence of hazardous materials in food products can be detected by scanning the food with the spectrometer and analyzing the resultant spectrum. Similarly, the spectrometer can be used to determine pet food quality. The pocket size spectrometer can be used to analyze the content of pet-food, such as the amount of meat and macro-nutrients in the food. Analysis of the spectral signature of the food can verify the food content and quality.

The spectrometer system disclosed herein may also be used in gemology applications. For example, the spectrometer may be used in the authentication of gems. Gems have different spectra than look-alike counterfeits. Scanning a gem with spectrometer can verify the authenticity of the gem and provide its declared quality, by comparing the spectrum of the measured gem with the spectra of gems of known identity and quality, pre-loaded in the database. The spectrometer can be used to sort multiple gems according to their quality. The quality of gems can be determined by analyzing the gem's spectrum, since impurities and processing can affect the spectral signature of the gem. Scanning multiple gems with a pocket size spectrometer gems can enable a quick yet rigorous classification of the gems according to their spectra.

The spectrometer system disclosed herein may also be used in law enforcement applications. For example, the spectrometer may be used to identify explosives. A pocket size spectrometer can provide the law enforcement personnel with an immediate analysis of the spectrum of the potential explosives. The spectrum of the material in question can be compared to an existing database of spectra of explosive materials. Uploading the explosive's spectrum can be used to link explosives that were found in different times and places, because of the unique spectra of non-standard explosives. The spectrometer can also provide the law enforcement personnel a fast and accurate way to identify illegal drugs. This is done by analyzing the spectrum of the material in question and comparing the spectrum to an existing database of drug spectra. Uploading the sampled drug's spectrum can be used to link drugs identified in different cases, because of the unique spectra that the drugs may have (resulting, for example, from adulteration with powders, processing, etc.).

The spectrometer system disclosed herein may also be used in authentication applications. For example, the spectrometer may be used for the authentication of alcoholic beverages. Alcoholic beverages of different brands have unique chemical compositions, determined by the many factors including the source of the ingredients and the processing of the ingredients. A pocket size spectrometer can provide these unique chemical signatures, providing a fast authentication procedure for verifying an expected alcoholic beverage composition. For example, the spectrometer may be configured to detect an amount of methanol or gamma-hydroxybutyric acid present in a beverage. The user may scan the product, and the spectrum can be instantly analyzed and compared to spectra from a pre-loaded database, and within seconds a proof of originality can be provided. The spectrometer system may also be used to obtain infrared spectra of goods, to serve as proofs of originality.

The spectrometer system disclosed herein may also be used in healthcare applications. For example, the spectrometer may be used for body fat estimation. Total body fat may be estimated by measuring the thickness of the subcutaneous adipose tissue at various locations of the human body. This can be done by scanning the skin in various places with pocket size spectrometer, and analyzing the spectra. The spectrometer may also be used to identify dehydration. A direct, non-invasive measurement of fluid balance may be obtained by observing skin surface morphology, which is associated with water content. A pocket-sized spectrometer can be used to scan the skin surface and thereby continuously monitor the dehydration level. A pocket size spectrometer can also provide a fast way to measure blood components non-destructively. The spectrometer can scan the sample inside test tubes, preserving the samples for further laboratory analysis. Such an analysis can yield immediate results that may be less accurate than laboratory test results, but can be followed up and verified by the lab test results at a later time point. For example, hemoglobin analysis can be performed using a pocket size spectrometer, which can identify hemoglobin levels in blood by taking non-invasive scans of blood samples. The small size and ease of use of the spectrometer can enable a continuous monitoring of hemoglobin levels, alerting the user to sharp changes in the levels and potential anemia. The spectrometer can also be used for analyzing the skin for various properties. For example, scanning the skin with the spectrometer can provide a direct way to analyze lesions, wounds, moles and spots, allowing a user to examine skin issues like tissue hypoxia, deep tissue injury, melanoma, etc., from home. In addition, skin analysis using the spectrometer may provide cosmetic information that allows customization of cosmetic products. Similarly, the spectrometer may provide a way to analyze hair. Scanning the hair with a pocket size spectrometer can provide valuable information about the hair (type, condition, damage, etc.) that can be used to customize cosmetic products like shampoo, conditioner, or other hair products.

Figure 23:
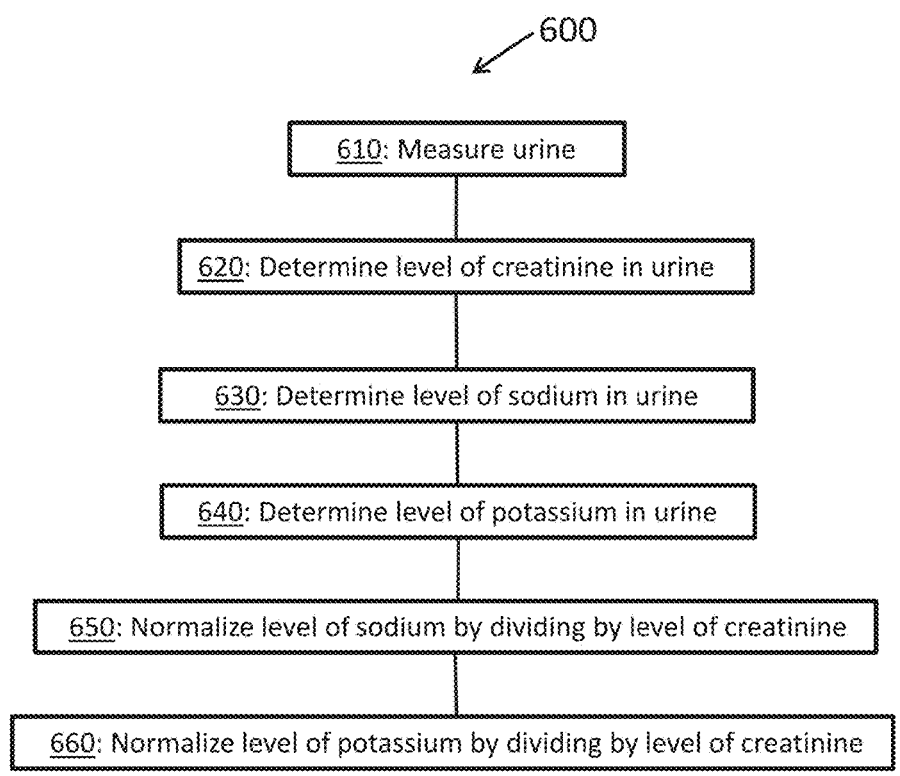
FIG. 23 shows a method for performing urine analysis using a spectrometer system in accordance with configurations.

The spectrometer may also be used for urine analysis at home. A spectrometer as disclosed herein may allow an immediate analysis of various solutes in the urine such as sodium, potassium, creatinine, and urea. In particular, a method 600 of urine salt analysis, as shown in FIG. 23, can be a useful tool for monitoring blood pressure. High blood pressure may be correlated with high levels of oral sodium intake, which can lead to high levels of sodium and potassium in the urine. However, an accurate determination of sodium intake via urine analysis can be difficult, as the absolute levels of sodium and potassium in the urine may be affected by confounding factors such as the volume of fluids consumed. In order to determine the levels of sodium and potassium in the urine that are truly correlated with sodium intake, measured levels of sodium and potassium may be normalized by measured levels of creatinine in the urine. For example, at step 610, a urine sample may be scanned using the spectrometer system described herein. At step 620, the spectrometer system may determine the level of creatinine in the urine based on the light spectrum of the urine sample. Similarly, at step 630, the spectrometer system may determine the level of sodium in the urine; at step 640, the spectrometer system may determine the level of potassium in the urine. At step 650, the level of sodium may be normalized, by dividing by the level of creatinine; similarly, at step 660, the level of potassium may be normalized, by dividing by the level of creatinine. The user interface may present to the user creatinine-normalized sodium and potassium levels in the urine, as indicators of the user's sodium intake. A spectrometer system configured to perform urine analysis methods such as method 600 can enable the continuous monitoring of urine solutes from home, as a way of monitoring related health conditions such as high blood pressure. The method 600 of urine salt analysis may also be performed using an electro-chemical sensor comprising parts of the spectrometer system described herein. The spectrometer or electro-chemical sensor may be embedded in a urinal and/or a toilet, in order to perform urine analysis as described herein.

The spectrometer system disclosed herein may also be used for fuel quality monitoring. For example, the spectrometer may be used to determine a type of fuel, a contaminant level, octane level, cetane level, or other substance composition. The spectrometer system for such applications may be configured for integration with a vehicle component. The vehicle component may be a fuel system component, such as a fuel tank, fuel line, or fuel injector of the vehicle.

The spectrometer system disclosed herein may also be used for monitoring power components. For example, the spectrometer may be used to determine the condition associated with a fluid of a power converting component.

The spectrometer system disclosed herein may be configured to measure a substance at a specific level of sensitivity suited for a specific application. For example, as described herein, the system may be used to determine the concentration of melamine in milk (powder or liquid). Generally, in many governments and regulatory agencies around the world, the allowable upper limit of melamine is in the range from about 0.1 to about 2 ppm, or approximately 1 ppm. However, such allowable upper limits may comprise aggressive margins designed to ensure that the melamine contaminants cause no damage even for the long term. For many consumers, an acceptable upper limit of melamine in milk may be closer to approximately 100 ppm, wherein levels above about 100 ppm may have potential implications for long term effects. Levels above about 1000 ppm may potentially cause short-term problems. Accordingly, for regulatory applications of the spectrometer system, the system may be configured to detect concentrations of melamine in milk of about 2 ppm or less, about 1 ppm or less, about 0.5 ppm or less, or about 0.1 ppm or less. For consumer uses of the spectrometer system in detecting potentially harmful levels of melamine in milk, the spectrometer system may be configured to detect concentrations of melamine in milk of about 5000 ppm or less, about 1000 ppm or less, about 500 ppm or less, about 250 ppm or less, or about 100 ppm or less.

For the urine analysis applications described herein, the spectrometer system may be configured to detect physical concentrations of the relevant substances at specific levels of sensitivity. For example, the spectrometer system may be configured to detect concentrations of sodium in the range from about 1.2 g/l to about 10 g/l, or about 20 g/l or less, about 15 g/l or less, about 10 g/l or less, about 5 g/l or less, about 2.5 g/l or less, or about 1.2 g/l or less. The spectrometer system may be configured to detect concentrations of potassium in the range from about 0.6 g/l to about 4 g/l, or about 10 g/l or less, about 5 g/l or less, about 4 g/l or less, about 2 g/l or less, about 1 g/l or less, or about 0.6 g/l or less. The spectrometer system may be configured to detect concentrations of creatinine in the range from about 0.4 g/l to about 2.6 g/l, or about 5 g/l or less, about 2.6 g/l or less, about 1.3 g/l or less, about 1 g/l or less, about 0.5 g/l or less, or about 0.4 g/l or less.

For the oil quality assurance applications described herein, the spectrometer system may be configured to detect oxidation levels of edible oils at specific levels of sensitivity. For example, in many countries, the recommended upper limit for the level of total polar compounds (TPC) in edible oils is about 27% or about 25%. Accordingly, for use in regulatory or consumer applications, the spectrometer system may be configured to detect levels of TPC in edible oils of about 27% or less, about 25% or less, about 20% or less, about 15% or less, or about 10% or less. The recommended upper limit for the level of free fatty acid (FFA) in edible oils is about 2% in many countries. Accordingly, for use in regulatory or consumer applications, the spectrometer system may be configured to detect levels of FFA in edible oils of about 2% or less, about 1.5% or less, about 1% or less, or about 0.5% or less.

The spectrometer system disclosed herein may be arranged in a custom configuration suited for use in a specific application. Due to its compact size, the spectrometer 102 may be removably or permanently embedded into various objects, appliances, or devices. The spectrometer 102 may be embedded in its entirety, for example in the configuration shown in FIG. 1, into another object, appliance, or device. Alternatively or in combination, one or more components of the spectrometer, such as the spectrometer head 120 or components thereof including the spectrometer module 160, illumination module 140, and sensor module 130, may be rearranged into a custom configuration suitable for embedding into a specific object, appliance, or device.

Figure 33A:
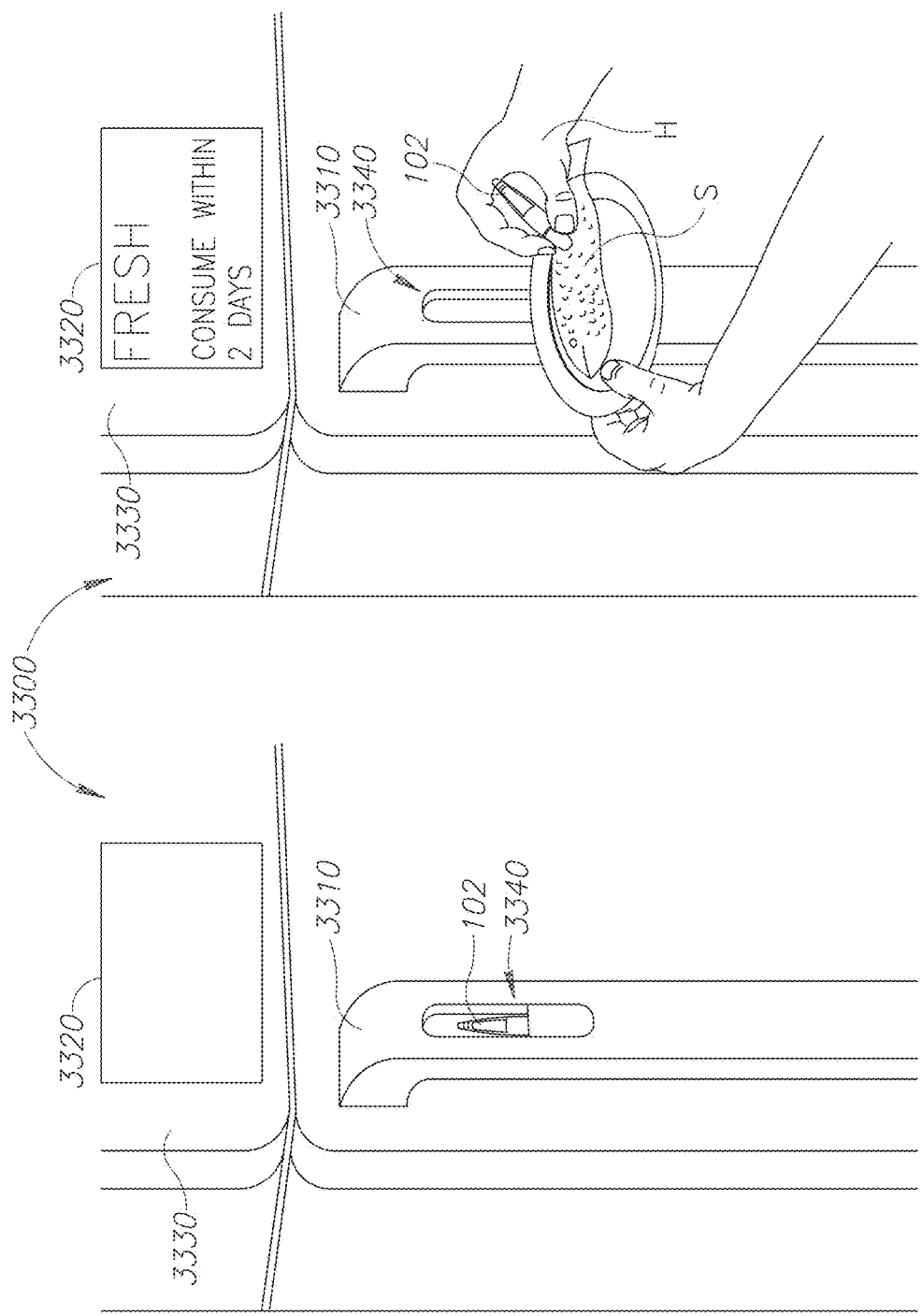
FIGS. 33A and 33B illustrate a spectrometer system integrated into a refrigerator.
Figure 33B:
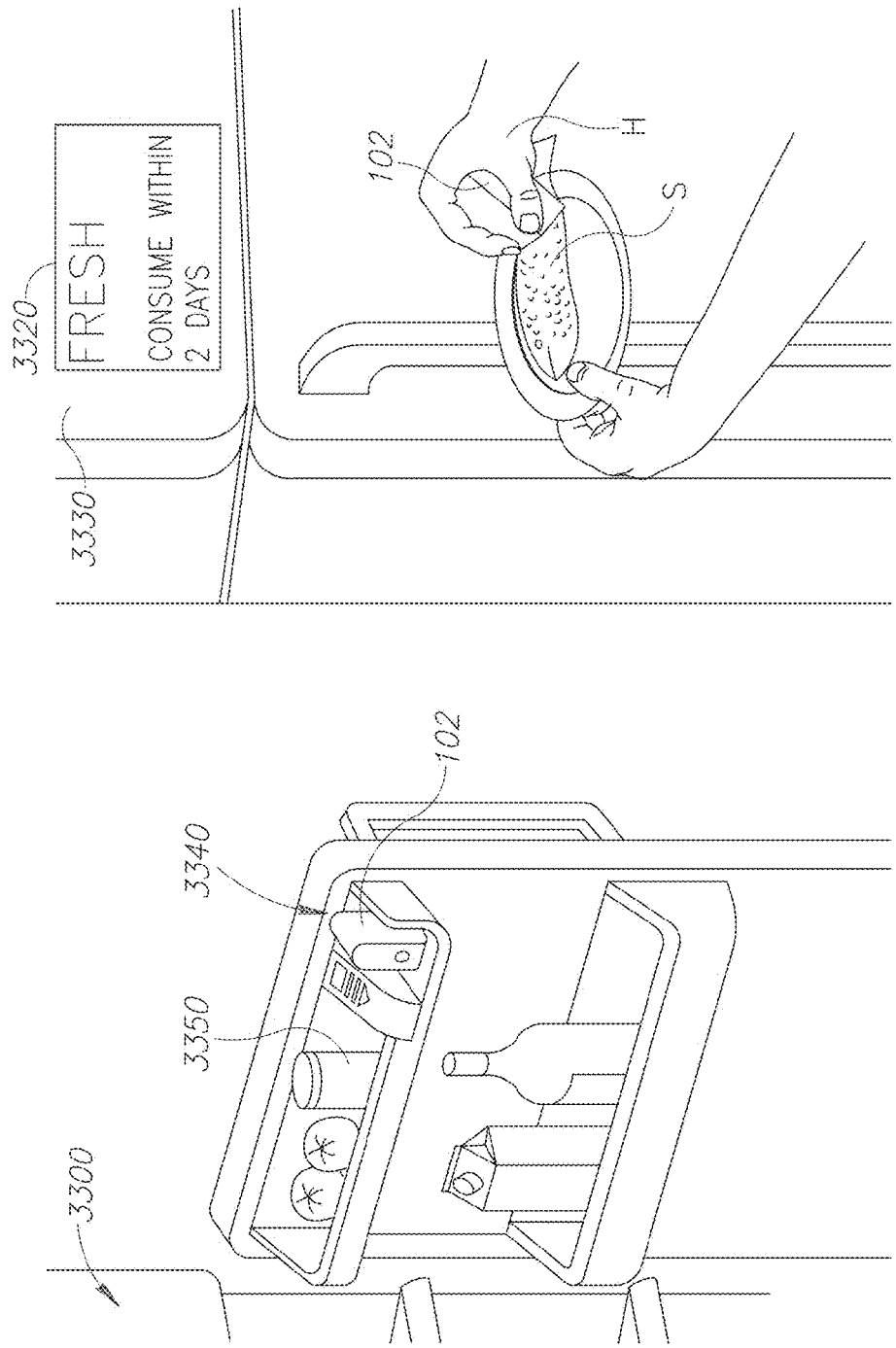

FIGS. 33A and 33B illustrate a spectrometer system integrated into a refrigerator. In FIG. 33A, a compact spectrometer 102 is removably embedded into a door handle 3310 of a refrigerator 3300. The handle 3310 may comprise a docking station 3340 for the spectrometer 102, and the spectrometer may be stored within the docking station when not in use. In FIG. 33B, a compact spectrometer 102 is removably embedded into an interior compartment such as shelf 3350 of the refrigerator 3300. The shelf 3350 may comprise a docking station 3340 for the spectrometer 102, which may receive the spectrometer when not in use. The docking station 3340 may be configured to charge a battery of the spectrometer when the spectrometer is stored in the docking station. The refrigerator 3300 may further comprise a display screen 3320 integrated with the refrigerator, the screen configured to display results of the measurements performed using the spectrometer 102. The display screen may, for example, be embedded on a refrigerator door 3330 as shown in FIGS. 33A and 33B. A user may decide to measure a sample, such as a food item from the refrigerator, using the spectrometer 102, for example to determine the freshness, safety, and/or quality of the food item. The user may then remove the spectrometer 102 from the docking station 3340, and holding the spectrometer with one hand H, point the spectrometer at the sample item S and take a measurement, using the same hand H to control operation of the spectrometer. The raw measurement data may be transmitted to a remote cloud based server 118 for analysis, as described in further detail herein. The data may be transmitted to the server either directly from the spectrometer or via another device in communication with the spectrometer, such as a mobile phone, or a processing unit integrated with the refrigerator 3300 and coupled to display screen 3320. The analyzed data may be transmitted back to the mobile phone or the display screen 3320, in order to display the results of the measurement to the user. The results may comprise, for example, an indication of the freshness of the measured sample, and/or further actionable insight such as instructions for the consumption of the sample or other recommendations for a course of action related to the sampled item.

Figure 34A:
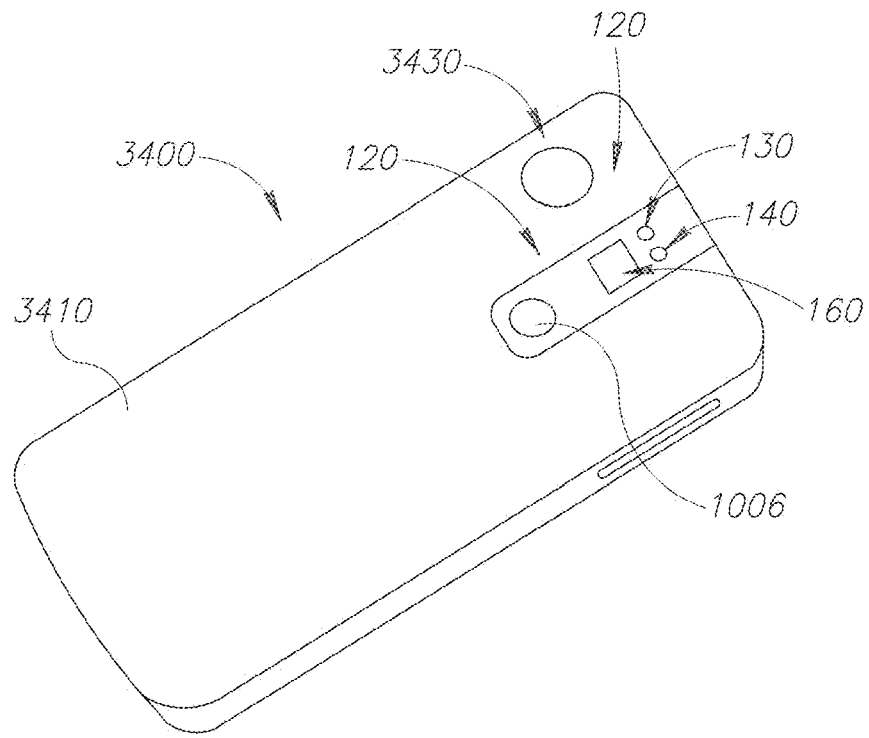
FIGS. 34A and 34B illustrate a spectrometer system integrated into a mobile phone case.
Figure 34B:
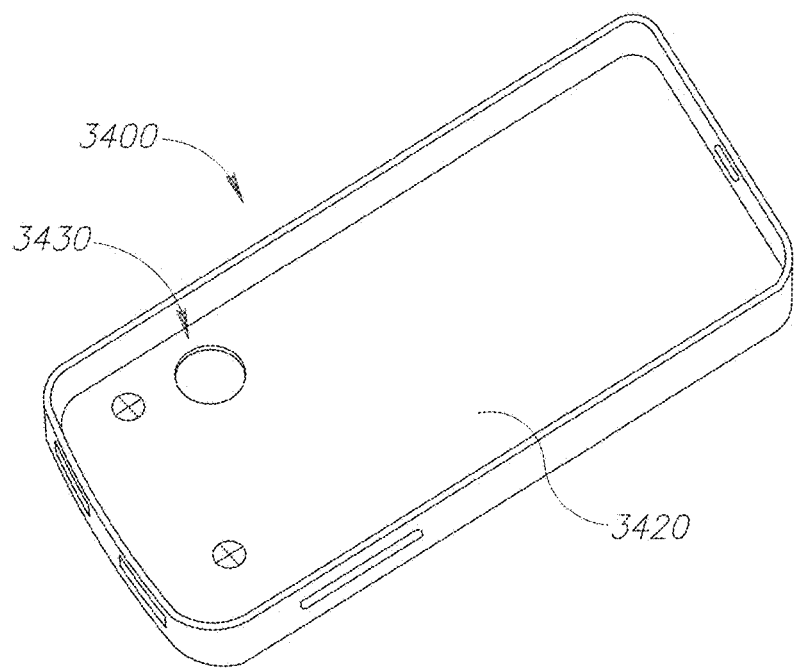

FIGS. 34A and 34B illustrate a spectrometer system integrated into a mobile phone case. FIG. 34A shows the exterior surface 3410 of the mobile phone case 3400 comprising an embedded compact spectrometer 120. FIG. 34B shows the interior surface 3420 of the phone case 3400. As shown in FIG. 34A, the spectrometer 102 is embedded into the mobile phone case 3400, such that the optical head 120 of the spectrometer is disposed on the exterior surface 3410 of the phone case. The optical head 120 comprises a spectrometer module 160, which includes a detector configured to measure the spectra of a sample. The optical head further comprises an illumination module 140, which includes a light source configured to produce an optical beam configured to illuminate the sample. The optical head may optionally comprise a sensor module 130, which may have one or more sensors configured to collect non-spectral information, such as ambient temperature. The mobile phone case 3400 may comprise an aperture 3430 configured to accommodate a built-in camera of a mobile phone used with the case. Components of the optical head 120 may be orientated such that the field of view of the detector of the spectrometer is disposed on the same plane as the field of view of the camera. The field of view of the detector may at least partially overlap with the field of view of camera. The spectrometer 102 may further comprise a user input for controlling the operation of the spectrometer, such as operating button 1006. The one or more modules or components of the spectrometer 102 may be arranged in a custom configuration, in order to fit within a phone case 3400 of a particular size and shape. Embedding the spectrometer in a mobile phone case can provide a convenient way for users to store, carry, and use the spectrometer.

Figure 34C:
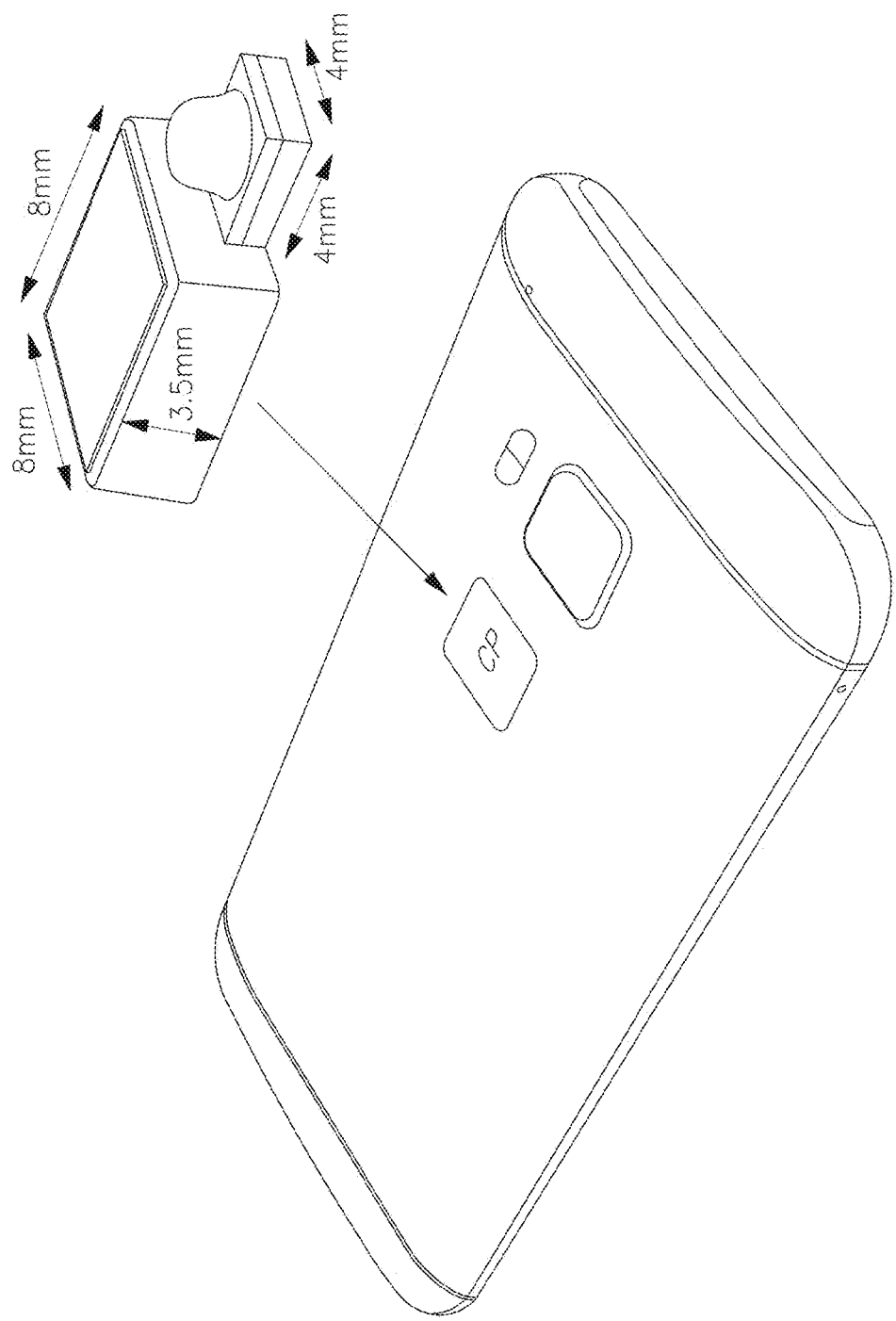
FIG. 34C illustrates a spectrometer system integrated into a mobile phone.

A compact spectrometer as described herein may be physically and/or functionally integrated with a smartphone, for example via integration into a housing for a smartphone, such as the mobile phone case 3400 as shown in FIGS. 34A and 34B. Alternatively, the spectrometer may be physically integrated with the smartphone itself as shown in FIG. 34C. For example, the spectrometer can be built into the smartphone, similarly to a smartphone-integrated camera. The smartphone may have various functional features supported by an advanced mobile operating system, such as one or more of a camera, accelerometer, or a global positioning system (GPS). The housing comprising an integrated compact spectrometer can be configured to communicate with the one or more functional features of the smartphone, for example via a connector to connect to a communication port of the smartphone. Alternatively or in combination, the processor of the compact spectrometer may comprise a communication circuitry as described herein (e.g., wireless serial communication link, such as Bluetooth™), such that the spectrometer can transmit and receive data to and from the smartphone. A compact spectrometer, thus functionally integrated with a smartphone, can use one or more functional features of the smartphone to enhance the performance of the spectrometer.

For example, the smartphone-integrated spectrometer can use the functionality of the smartphone's camera in order to facilitate the user's positioning and orientation of the spectrometer with respect to the sample surface during measurement. The smartphone-integrated spectrometer can comprise a housing such as mobile phone case 3400 shown in FIGS. 34A and 34B, wherein the housing can comprise an aperture 3430 configured to accommodate the lens of the smartphone's built-in camera. The housing may be configured to have the aperture disposed adjacent to the compact spectrometer 102 and component modules thereof, such that the smartphone camera may have a field of view that at least partially overlaps with the field of view of the spectrometer. Alternatively, the smartphone-integrated spectrometer can comprise a spectrometer that is built into the smartphone itself, wherein the spectrometer module and/or the illumination module of the built-in spectrometer are disposed adjacent the lens of the built-in camera, and configured to have a field of view that at least partially overlaps with the field of view of the spectrometer. For example, the distance between the camera lens and the illumination module or spectrometer module of the spectrometer may be in the range from about 1 mm to about 20 mm, or about 1 mm to about 10 mm. The spectrometer may be configured such that the camera's field of view can partially or completely capture the spectrometer's visible optical beam, such that the user may view of the visible optical beam via the smartphone camera before and during measurement with the spectrometer.

Often, the compact spectrometer needs to be positioned close to the surface of the sample in order to produce optimal measurements. When the spectrometer is disposed on the back side of a smartphone, as shown in the embodiment of FIGS. 34A-34C, it may be difficult for the user to aim the spectrometer at a proper spot of the sample surface, and/or at a proper distance from the sample surface. To facilitate the user's aiming of the spectrometer, the spectrometer may be configured to access the smartphone camera and provide to the user a view of the sample surface behind the smartphone. A crosshair or other type of indication layer, indicating the measurement area of the sample surface, may be added to the view to further aid the user's aiming of the spectrometer. Alternatively or in combination, the visible, reflected portion of the spectrometer's optical beam, described in further detail herein, may be viewed by the user via the camera, such that the user may adjust the spectrometer's position and orientation to appropriately position the visible beam over the desired measurement area.

Figure 35:
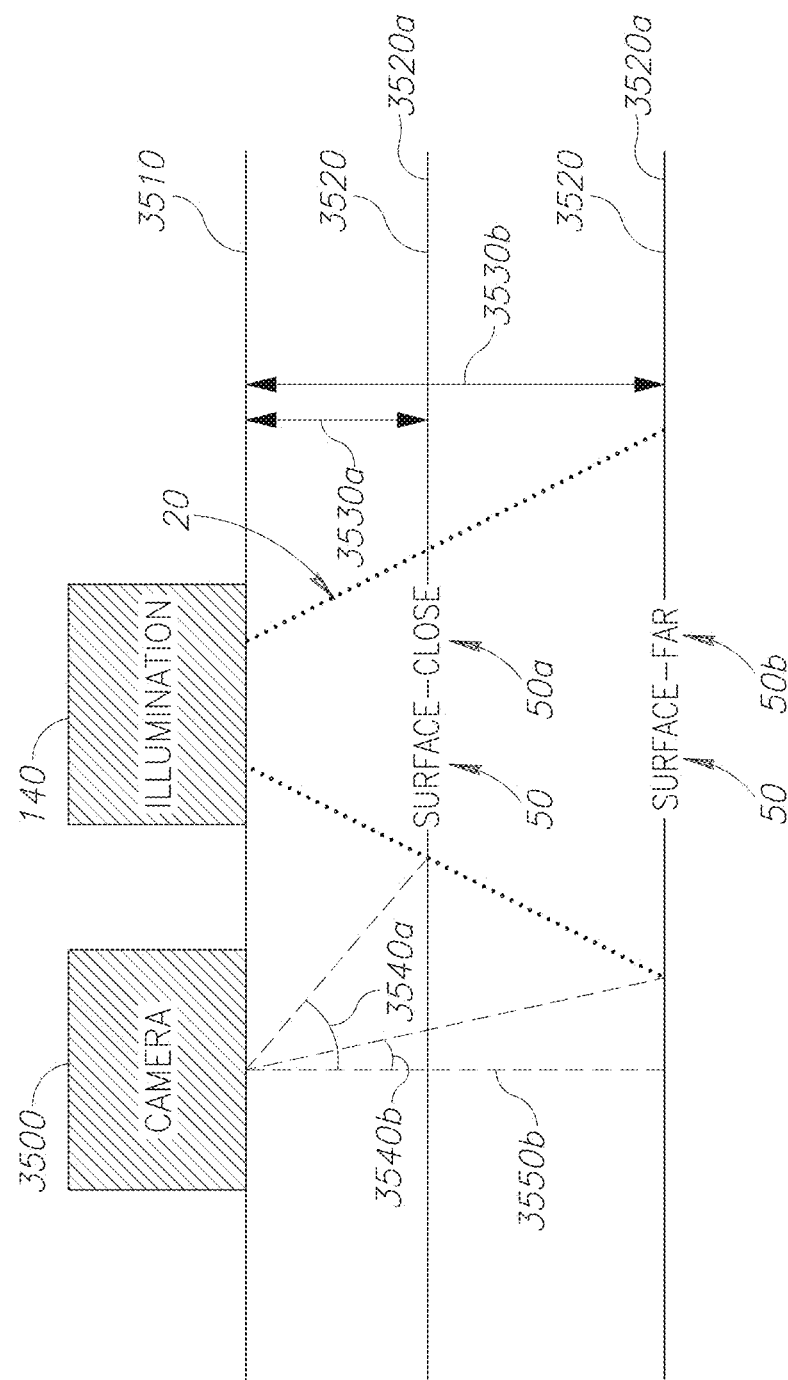
FIG. 35 illustrates the parallax between the illumination module of a smartphone-integrated spectrometer and the smartphone camera.

In particular, the smartphone-integrated spectrometer may be configured to account for the distance between the spectrometer and the sample surface, using a camera built into the smartphone. FIG. 35 illustrates the parallax between the illumination module 140 of the spectrometer and the smartphone camera 3500. In many configurations, a parallax may exist between the illumination module and the camera, since the illumination module and the lens of the camera (which may be disposed within an aperture 3430 of the mobile phone case 3400 as shown in FIGS. 34A and 34B, or positioned adjacent the built-in spectrometer as shown in FIG. 34C) are often positioned at some distance from one another. As shown in FIG. 35, the illumination module 140 may emit a visible aiming beam 20 directed towards the sample surface 3520, defining a measurement area 50. The measurement area may appear at different angles to the camera, depending on the distance of the sample surface from the smartphone. For example, the sample surface 3520a may be positioned at a distance 3530a from the plane 3510 of the illumination module, which may coincide with the rear, exterior surface of the mobile phone case supporting the smartphone. At distance 3530a, the measurement area 50a on the sample surface 3520a may appear at an angle 3540a from the optical axis 3550 of the camera. When the smartphone is positioned farther from the sample surface, for example at a distance 3530b between the sample surface 3520b and illumination module plane 3510, the measurement area 50b may appear at an angle 3540b different from angle 3540a. As shown in FIG. 35, angle 3540a, wherein the smartphone is closer to the sample surface, may be larger than angle 3540b, wherein the smartphone is farther from the sample surface. These spectrometer system can be configured to allow the user to visualize these differences, and use the perceived differences as feedback in placing the sample surface at an appropriate distance from the spectrometer.

Figure 36A:
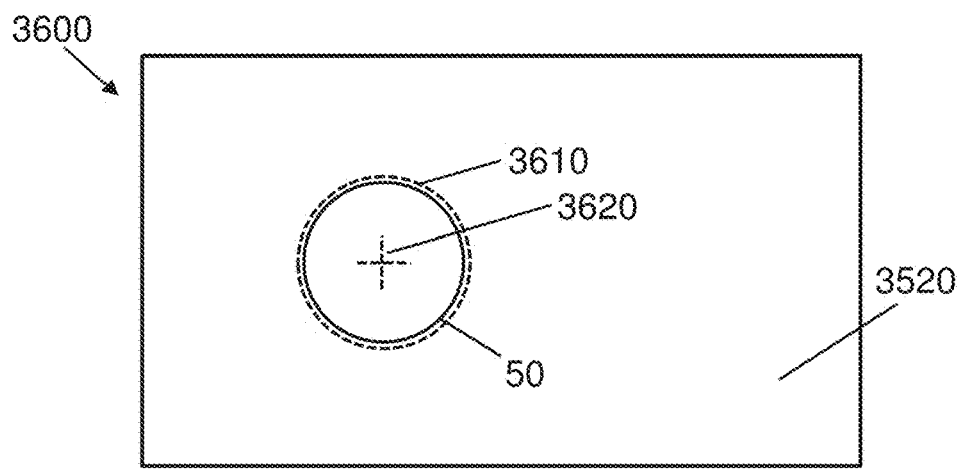
FIGS. 36A-36C illustrate the visualization of the parallax between the illumination module and the smartphone camera via a display of the smartphone camera.
Figure 36B:
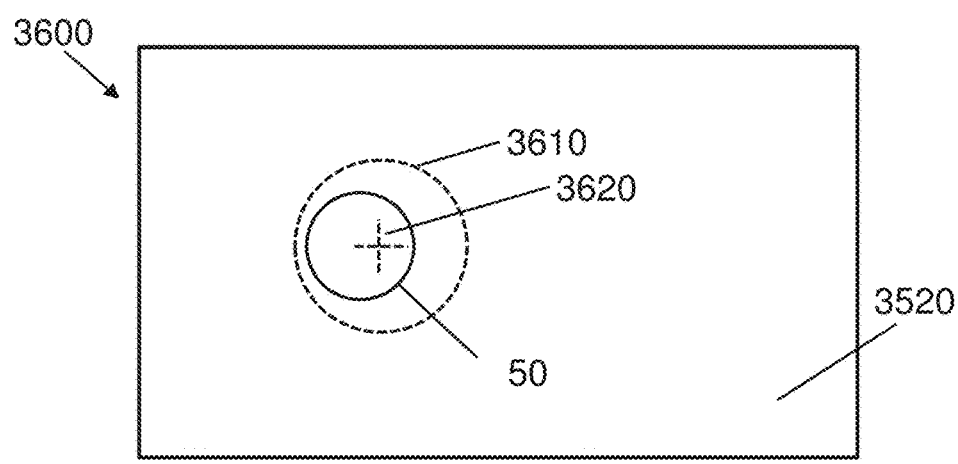
Figure 36C:
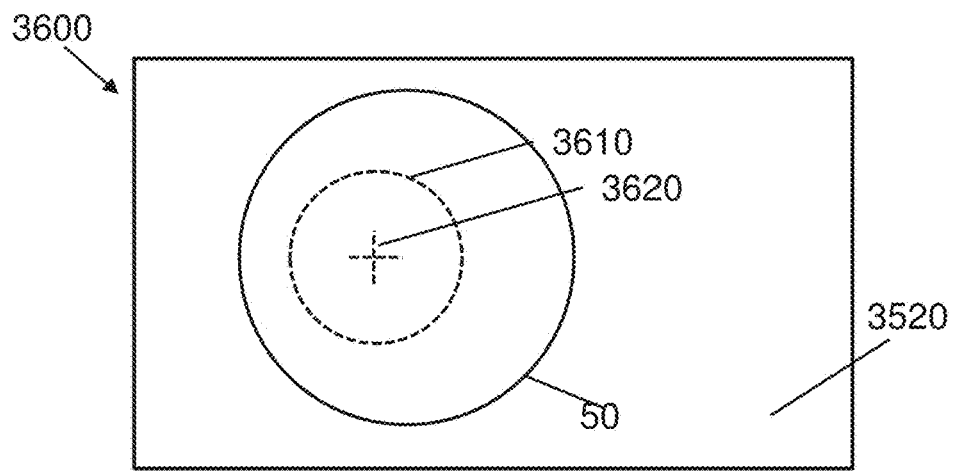

FIGS. 36A-36C illustrate the visualization of the parallax between the illumination module 140 and the smartphone camera 3500 via a display of 3600 the smartphone camera. The spectrometer system may be configured to provide an indication layer on the smartphone camera display, in order to provide a visualization of the parallax between the illumination module and the camera. The indication layer can comprise, for example, a computer projected target 3610 configured to align with the visible optical beam of the spectrometer, when the spectrometer is positioned at the correct distance from the sample surface. The indication layer may also comprise a crosshair 3620 or other marker indicating the center of the computer projected target 3610. FIG. 36A illustrates the smartphone camera display 3600 when the smartphone is placed at the correct or optimal distance away from the sample surface 3520. In this instance, the measurement area 50, indicated by the visible aiming beam of the spectrometer projected on the sample surface, may appear substantially aligned with the computer projected target 3620. In addition, the center of the measurement area 50 may appear substantially aligned with the crosshair 3620. The computer projected target 3610 may appear off-center from the center of the smartphone camera display, since the camera display will frequently be centered about the camera's field of view; the camera's field of view may not be aligned with the visible optical beam produced by the illumination module, due to the distance between the camera and the illumination module. A camera display similar to that shown in FIG. 36A can indicate to the user that the smartphone-integrated spectrometer is at the correct distance away from the sample surface for measurement. FIG. 36B illustrates the smartphone camera display 3600 when the smartphone is placed at a shorter than ideal distance from the sample surface 3520. In this instance, the measurement area 50 may appear smaller than the computer projected target 3620, and the center of the measurement area 50 may be misaligned with the crosshair 3620 such that the measurement area moves farther from the center of the smartphone camera display. A camera display similar to that shown in FIG. 36B can indicate to the user that the smartphone-integrated spectrometer is too close to the sample surface for measurement, and the user may move the spectrometer farther from the sample surface until the camera display shows a view similar to that shown in FIG. 36A. FIG. 36C illustrates the smartphone camera display 3600 when the smartphone is placed at a longer than ideal distance from the sample surface 3520. In this instance, the measurement area 50 may appear larger than the computer projected target 3620, and the center of the measurement area 50 may be misaligned with the crosshair 3620 such that the measurement area moves closer to the center of the smartphone camera display. A camera display similar to that shown in FIG. 36C can indicate to the user that the smartphone-integrated spectrometer is too far from the sample surface for measurement, and the user may move the spectrometer closer to the sample surface until the camera display shows a view similar to that shown in FIG. 36A. The user can thus visualize the parallax between the camera and the illumination module, and accordingly adjust the position of the smartphone-integrated spectrometer to place the spectrometer at the correct distance from the sample surface.

In many configurations, a parallax may also exist between the illumination module and the spectrometer module of the spectrometer, since the illumination module and the spectrometer module are often separated by some distance (see, e.g., FIG. 5 showing a schematic diagram of a spectrometer head 120, wherein the spectrometer module 160 and the illumination module 140 are physically separated over the area of the spectrometer head). The measurement signals generated by the spectrometer may comprise components that change based on the distance between the spectrometer and the sample surface, due to this parallax between the illumination module and the spectrometer module. Based on these distance-dependent changes in measurement signal, the spectrometer system (the spectrometer and/or a computing device providing a user interface for the spectrometer, e.g., a mobile app installed on the smartphone) may be further configured to calculate an estimated distance between the sample surface and the smartphone. Further, the spectrometer system may be configured to reduce the sample distance-dependent changes in measurement signal. If the smartphone camera is used to estimate, based on the parallax between the camera and the spectrometer, the distance between the sample surface and the spectrometer, the spectrometer system may be configured to apply this estimated distance to the analysis of spectrometer measurements. For example, the spectrometer system can be configured to reduce or eliminate the components of the measurement signal that can be attributed to the specific distance as estimated by the camera analysis.

A smartphone-integrated spectrometer can also use the functionality of the smartphone camera to measure a sample comprising a plurality of different components. For example, a smartphone-integrated spectrometer may be configured to measure a plate of food containing a plurality of different food items. The user interface of the spectrometer system can direct the user to take a picture of the whole plate, using the smartphone camera. The user interface may subsequently guide the user to take measurements of different areas of the plate, containing different food items, with the spectrometer. One or more properties of each measured item may be determined via the item's spectral signature, as described herein (e.g., item's chemical composition/identity, calories, fat content, sodium content, etc.). An information layer may be displayed to the user via augmented reality, wherein different food items on the plate are marked according to one or more of the items' properties as determined from the spectral data (e.g., high calorie items may be marked red). Further, computer vision algorithms may be applied, optionally in combination with a smartphone-integrated depth camera, to estimate the volume of each item on the plate. Once all items are sampled, the spectrometer system may be configured to provide and track the full nutritional properties being consumed over the meal.

Smartphone-integrated functionalities may also be used to optimize measurement of a sample with the spectrometer. During the measurement period, movement of the spectrometer relative to the sample surface is ideally minimized, since excessive movement may reduce the accuracy of the measurement. If the smartphone comprises an accelerometer, the smartphone-integrated spectrometer system may be configured to query the accelerometer for the movement of the smartphone during sample measurement with the spectrometer. Alternatively or in combination, if the smartphone comprises a camera, images acquired using the camera during sample measurement may be used to estimate the relative movement of the sample surface with respect to the smartphone during measurement. The camera may be able to identify instances in which the sample, rather than the smartphone, is moving. If movement of the smartphone and/or the sample beyond a set threshold level is detected, the user interface of the spectrometer system may provide an indication to the user that the sample measurement should be repeated in a steadier manner.

A smartphone-integrated camera may also be used to improve the analysis of spectral data obtained using a smartphone-integrated spectrometer. In some instances, some features of a sample may be difficult to extract from the sample's spectral data, but relatively easy to extract by analyzing a picture of the sample. For example, an apple and a pear may have a very similar spectral signature, but have distinctly different appearances. To facilitate the identification of the sample, the smartphone camera may be used to acquire images of the sample, and computer vision algorithms may be applied to the images to extract certain visual properties of the sample (e.g., shape, proportion, size, color, texture of skin, etc.). The properties extracted from the images can be provided to the spectral data analysis algorithms in addition to the spectral data, to improve the efficiency and accuracy of sample identification.

A global positioning system (GPS), often built into a smartphone, can also be used to improve the analysis of spectral data obtained using a smartphone-integrated spectrometer. As described herein, the spectrometer system can query a database of materials to determine the identity of the sample material. To help improve the identification of the sample material, the spectrometer system may be configured to query the GPS for the geographical location of the smartphone and hence the sample. The spectrometer system may then use the location information to more efficiently identify the sample material, for example by narrowing down the possible identification results to a subset of the database of materials based on geographical location. For example, if the sample is a pill and the spectral data of the sample pill indicates the presence of acetaminophen, the spectrometer system may compare the sample spectra to the spectra of Tylenol and Panadol in the universal database if the GPS indicates that the user is located in the United States; for a substantially similar sample pill, if the GPS indicates that the user is located in Germany, the spectrometer system may compare the sample spectra to the spectra of Enelfa or Perfalgan in the database. If a "match" is not found between the sample spectra and the spectra of one of the materials filtered based on geographical location, the spectrometer system may continue to search the database for materials outside the user's geographical location. In many instances, however, an initial focusing of the database to results within a specific geographical location may help to more quickly and accurately identify the sample material.

Not only can various functional features of a smartphone enhance the performance of a smartphone-integrated spectrometer, but also the spectrometer can augment one or more functionalities of the smartphone. In particular, information derived from spectral measurements using the smartphone-integrated spectrometer can be used to improve the performance of smartphone functionalities that do not comprise measuring the spectra of samples. For example, the smartphone-integrated spectrometer can enhance the performance of a smartphone camera, for example by improving a color correction algorithm of the camera. A common problem with digital cameras is the white balance issue, wherein the consistency of colors in acquired images can be compromised by the requirement for different compensation levels for different illumination types. Most smartphone cameras include some sort of white balance correction, usually based on heuristic algorithms that estimate the illumination type from the colors of the scene. An integrated spectrometer can provide information on the illumination type, even when the spectrometer is tuned to the near infrared (NIR) range, since many common illumination types have some spectral signature in the NIR range. For example, daylight has characteristic atmospheric absorption lines, and different variants of daylight (e.g., clear skies, cloudy skies, dusk or dawn, etc.) may be identified from the NIR part of the ambient spectrum. Fluorescent and neon lamps have distinct emission lines that extend to the NIR, based on which these illumination types may easily be identified. Incandescent lamps have a distinct black body radiation curve, so the presence of such lamps as well as the filament temperature may be easily derived from the NIR spectrum. White light-emitting diode (LED) illumination includes blue excitation wavelength which is not visible in the NIR, and yellow phosphor emission that has some minor extension into the NIR. This small extension, alone or in combination with a characteristic illumination as detected by the camera, can suggest the presence of LED illumination. Further, the abundance of information available in the NIR spectrum can also enable the detection of mixed illumination scenes, a scenario which can pose a technical challenge for many traditional white balance algorithms. The illumination type as determined by the spectrometer, instead of or in addition to the information in the scene viewed by the camera, may be used to estimate the illumination type, improving the success rate of the white balance algorithms and reducing the instances in which a picture with shifted and unnatural colors is acquired.

Figure 37:
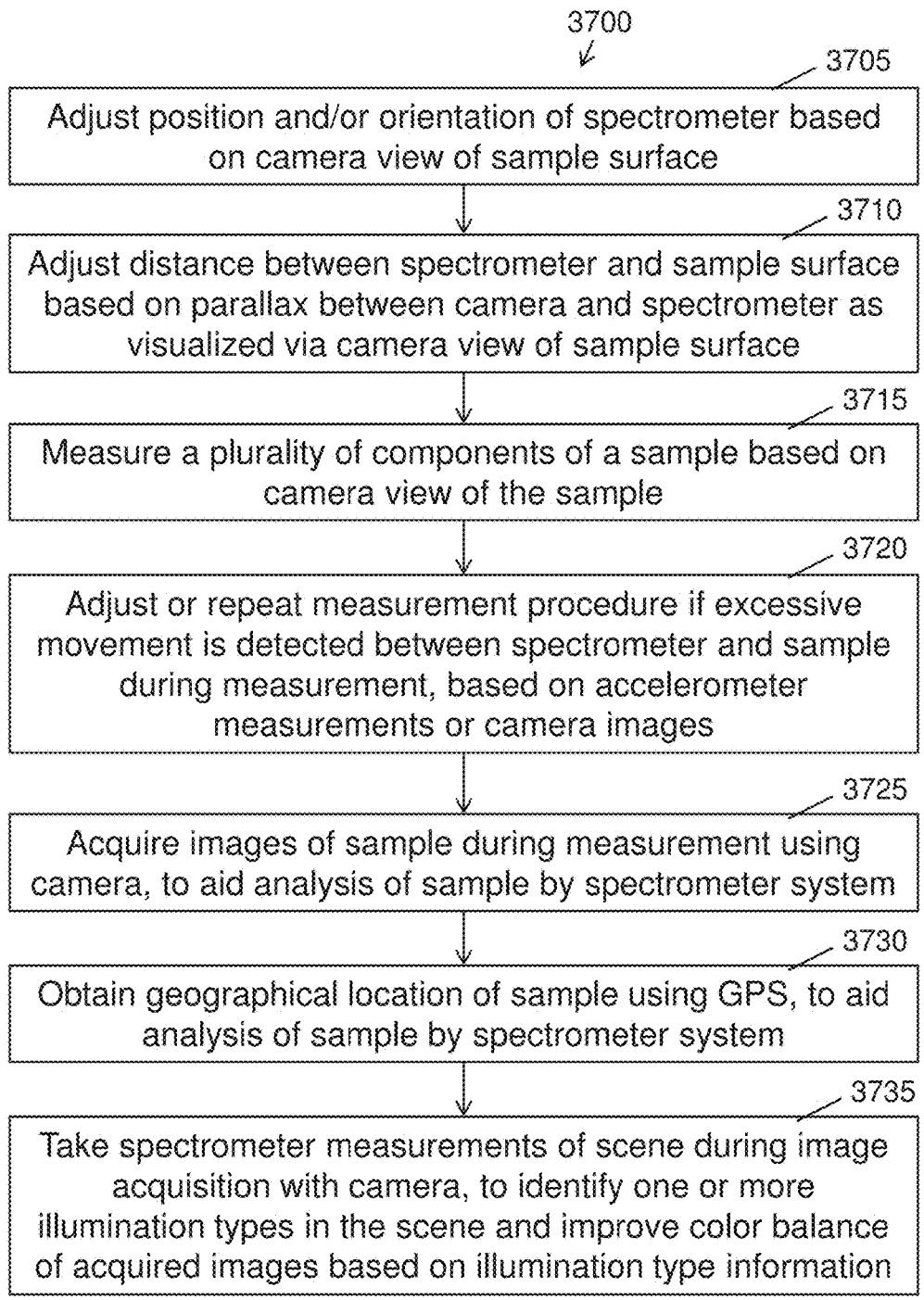
FIG. 37 illustrates a method of using a smartphone-integrated spectrometer as described herein.

FIG. 37 illustrates a method 3700 of using a smartphone-integrated spectrometer as described herein. At step 3705, a user may adjust a position and/or orientation of a smartphone-integrated spectrometer, based on a smartphone camera view of the sample surface. For example, as described herein, an indication layer may be provided in the camera view to guide the user in determining the correct position of the spectrometer. At step 3710, a user may adjust the distance between the smartphone-integrated spectrometer and the sample surface, based on the parallax between the camera and the illumination module of the spectrometer as visualized via the camera view of the sample surface. At step 3715, a user may measure a plurality of components of a sample, based on the camera view of the sample. As described herein, the camera view may provide an information layer showing one or more properties of each sample component as determined from the spectrometer measurements. At step 3720, a user may adjust or repeat a measurement procedure if excessive movement is detected between the smartphone-integrated spectrometer and the sample during measurement, based on accelerometer measurements or camera images as described herein. At step 3725, a user may acquire images of the sample during spectrometer measurement using the smartphone camera, to aid analysis of the sample by the spectrometer system. For example, as described herein, a computer vision algorithm may be applied to extract one or more visual properties of the sample from the sample image, and the visual properties may be provided to the spectral data analysis algorithm to facilitate sample identification. The smartphone-integrated spectrometer may be configured to automatically perform step 3725 when the user is taking a spectrometer measurement, without requiring explicit user input or instructions to perform the step. At step 3730, the user may obtain the geographical location of the sample using a GPS built-in to the smartphone, to aid analysis of the sample by the spectrometer system as described herein. The smartphone-integrated spectrometer may be configured to automatically perform step 3730 when the user is taking a spectrometer measurement, without requiring explicit user input or instructions to perform the step. At step 3735, the user may take spectrometer measurements of a scene during image acquisition with the smartphone camera, to identify one or more illumination types in the scene and improve the color balance of the acquired images based on the illumination type information. The smartphone-integrated spectrometer may be configured to automatically perform step 3735 when the user is acquiring images using the smartphone camera, without requiring explicit user input or instructions to perform the step.

Although the above steps show method 3700 of using a smartphone-integrated spectrometer in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary or beneficial.

The spectrometer can also improve the function of one or more software applications installed on the smartphone. The smartphone may comprise one or more software applications configured to provide specific services to the user of the smartphone, such as software applications configured to provide one or more applications of spectrometer data as described herein (e.g., soil analysis, plant water content analysis, fertilization status analysis, pill identification, food analysis, gem authentication, etc.), or software applications configured to provide services that are related to the one or more applications of spectrometer data as described herein. Object information derived from spectral measurements of the sample material can be transmitted to a relevant software application, where the information can be used to improve the performance of the application. The object data can comprise an identification of the sample and/or one or more components thereof (e.g., identification of sample as an orange, identification of sugars in the orange; identification of a pill, identification of active ingredients in the pill), a quantification of the sample and/or one or more components thereof (e.g., % fat per unit volume), and/or a determination of one or more secondary characteristics of the sample (e.g., sweetness of a piece of fruit, caloric content of a meal, quality of a gem, authenticity of a pill). The object data can help to improve the accuracy and reliability of the service provided by the software application, and/or increase the quantity and quality of the information provided to the user by the software application.

For example, the smartphone may comprise a mobile app for diet tracking, configured to track the diet of the user and provide guidelines for reducing calorie intake and/or improving nutrition. The smartphone-integrated spectrometer, which can obtain information about food such as calorie and nutritional content based on spectral measurements of food as described herein, can be configured to send the information to the mobile app. The information derived from spectral measurements can provide the mobile app with a more detailed and accurate account of the user's dietary intake, especially in cases where the user has consumed an item that is not catalogued by the mobile app's existing database or difficult for the user to identify or quantify. Another example of a software application whose functionality may be improved using information obtained by the spectrometer is a health and fitness application, configured to track a user's fitness and provide guidelines for exercise. The smartphone-integrated spectrometer may be used to measure a user's body to obtain information relevant to fitness, such as hydration level or body fat estimation, as described herein. The information can be provided to the mobile app, which can use the information to better understand the user's fitness state or body condition, and provide exercise routines that are custom-tailored accordingly.

Experimental Data

Figure 24:
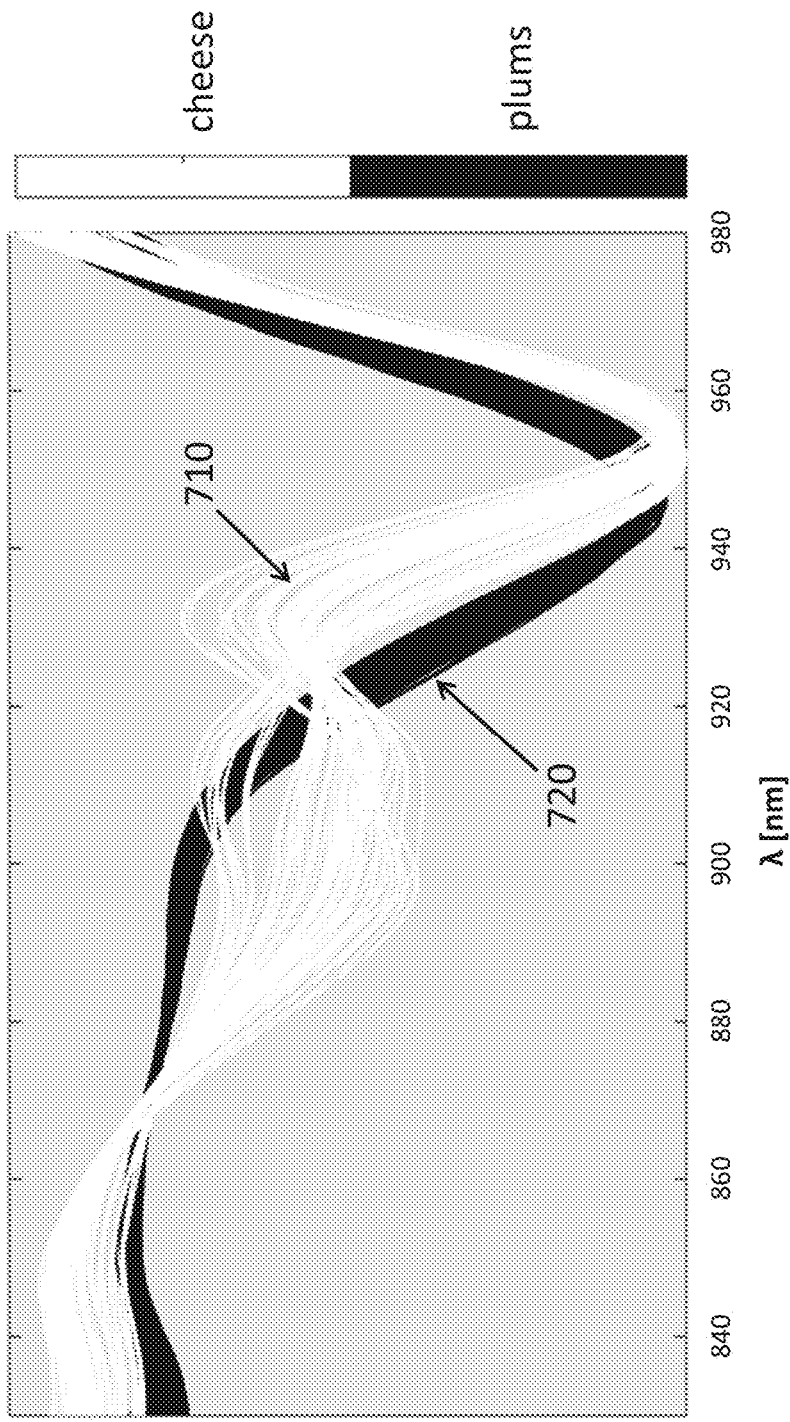
FIG. 24 shows exemplary spectra of plums and cheeses, suitable for incorporation in accordance with configurations.

FIG. 24 shows exemplary spectra of plums and cheeses, suitable for incorporation in accordance with configurations. The spectra of various cheeses 710 and the spectra of various plums 720 are shown to have characteristic features specific to the material type. Characteristic features include, for example, the general shape of the spectra, the number of peaks and valleys in the spectra within a certain wavelength range, and the corresponding wavelengths or wavelength ranges of said peaks and valleys of the spectra. Based on such characteristic features, a spectrometer system as described herein can determine the general identity (e.g., "cheese", "plum") of a sampled material, by comparing the measured spectral data against the spectral data of various materials stored in the universal database, as described herein. While FIG. 24 shows the spectra of plums and cheeses in the wavelength range of about 830 nm to about 980 nm, the spectra may be analyzed at any wavelength range that comprises one or more differences between the characteristic features of the spectra of the different materials.

Figure 25:
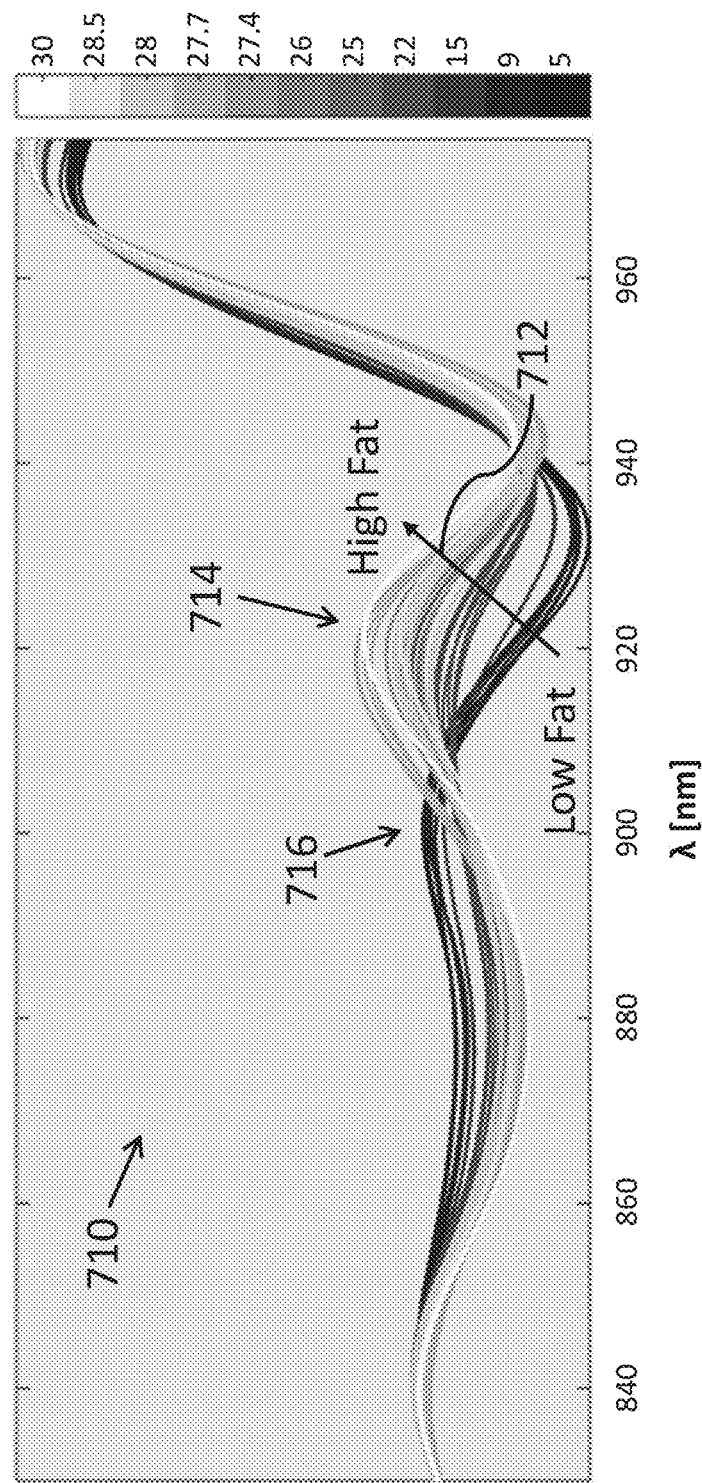
FIG. 25 shows exemplary spectra of cheeses comprising various fat levels, suitable for incorporation in accordance with configurations.

FIG. 25 shows exemplary spectra of cheeses comprising various fat levels, suitable for incorporation in accordance with configurations. The spectra share general characteristic features in the wavelength range of about 840 nm to about 970 nm that enable their identification as spectra of cheeses 710, but also have differences in their features that correspond to differences in the fat levels of the measured cheeses. In the spectra shown in FIG. 25, the spectra trend from having relatively lower fat content to relatively higher fat content in the direction indicated by arrow 712. For example, the spectra of cheeses having higher fat levels tend to have more distinct secondary peaks 714 compared to the secondary peaks 716 of the spectra of cheeses having lower fat levels. The secondary peaks 714 of the high-fat cheeses also tend to be shifted to the right (i.e., to higher wavelengths) compared to the secondary peaks 716 of the low-fat cheeses; in FIG. 25, the secondary peaks 714 of the high-fat cheeses are centered at around 920 nm, whereas the secondary peaks 716 of the low-fat cheeses are centered at around 900 nm.

Figure 26:
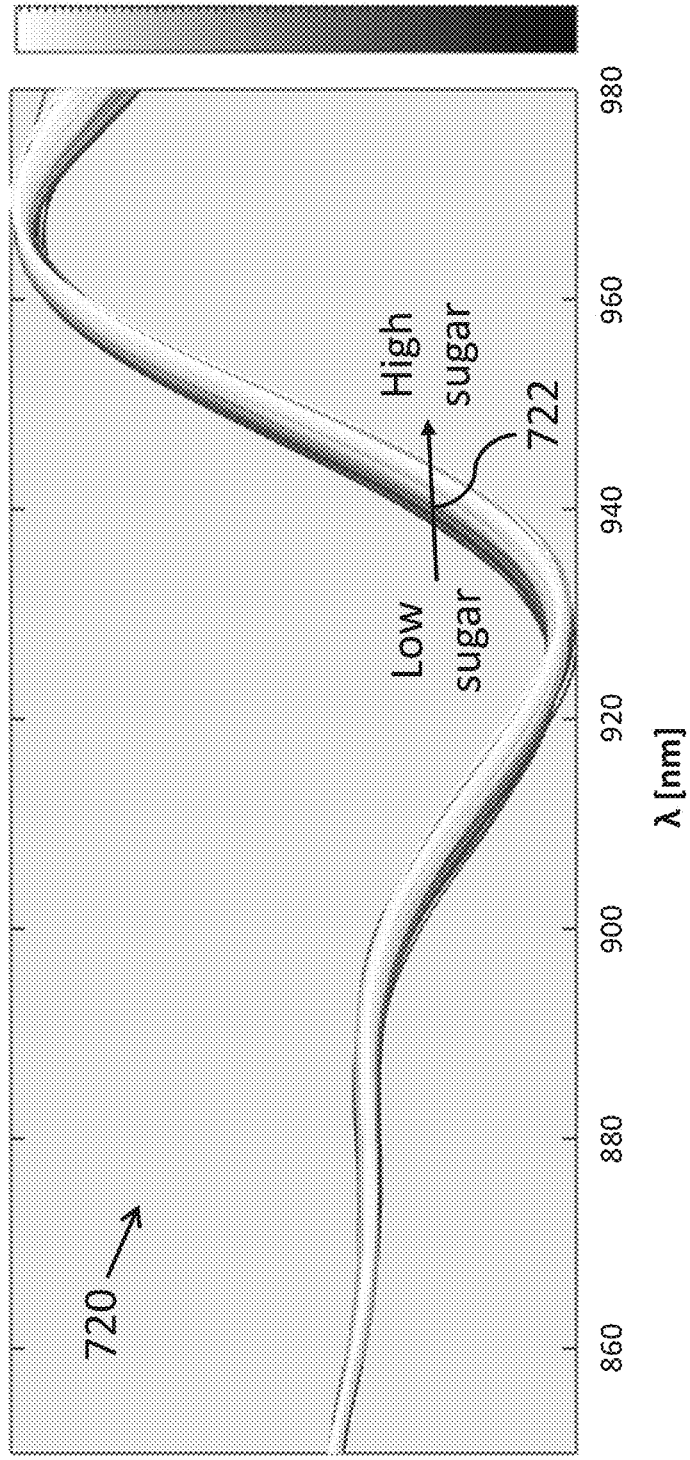
FIG. 26 shows exemplary spectra of plums comprising various sugar levels, suitable for incorporation in accordance with configurations.

FIG. 26 shows exemplary spectra of plums comprising various sugar levels, suitable for incorporation in accordance with configurations. The spectra share general characteristic features in the wavelength range of about 860 nm to about 980 nm that enable their identification as spectra of plums 720, but also have differences in their features that correspond to differences in the sugar levels of the measured plums. In the spectra shown in FIG. 26, the spectra trend from having relatively lower sugar content to relatively higher sugar content in the direction indicated by arrow 722. For example, the spectra of plums having higher sugar levels tend to be shifted to the right (i.e., to higher wavelengths) by approximately 5-7 nm compared to the spectra of plums having lower sugar levels.

As shown in FIGS. 25 and 26, differences in one or more spectral features among spectra of the same general material type can provide information regarding the different levels of sub-components (e.g., fat, sugar) of the material. The spectrometer system as described herein may identify such differences by comparing the measured spectral data against the spectral data of a specific material type stored in the universal database, and provide the user with information regarding the composition of the measured material.

Figure 27:
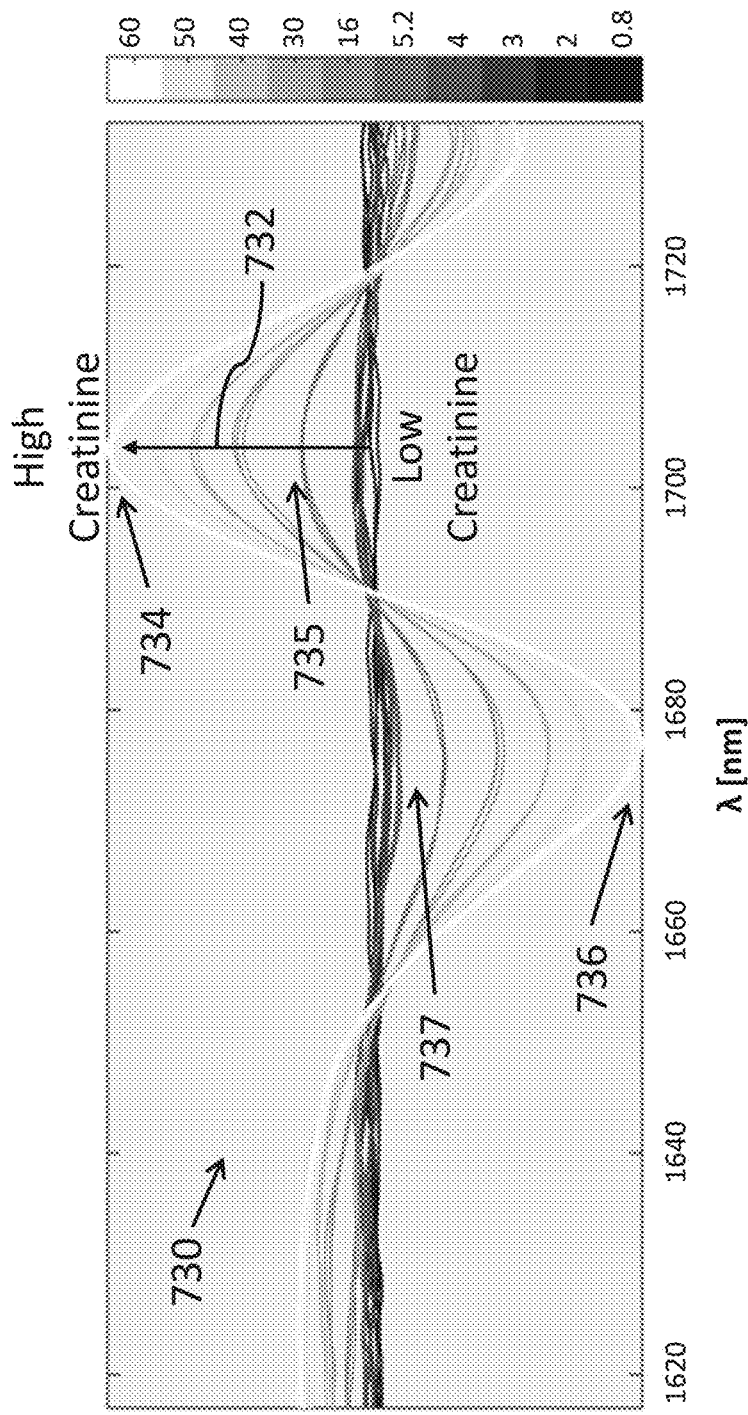
FIG. 27 shows exemplary spectra of aqueous solutions comprising various levels of creatinine, suitable for incorporation in accordance with configurations.
Figure 28:
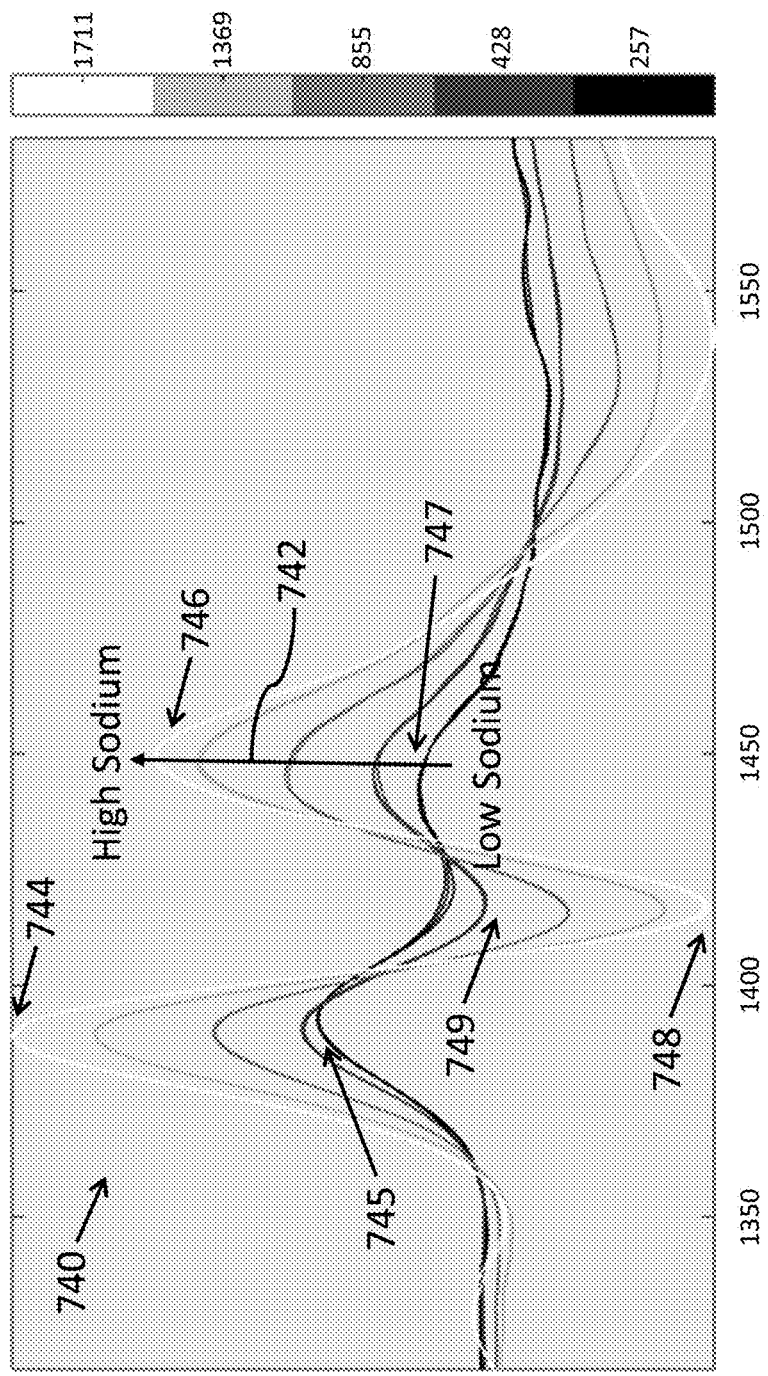
FIG. 28 shows exemplary spectra of aqueous solutions comprising various levels of sodium, suitable for incorporation in accordance with configurations.
Figure 29:
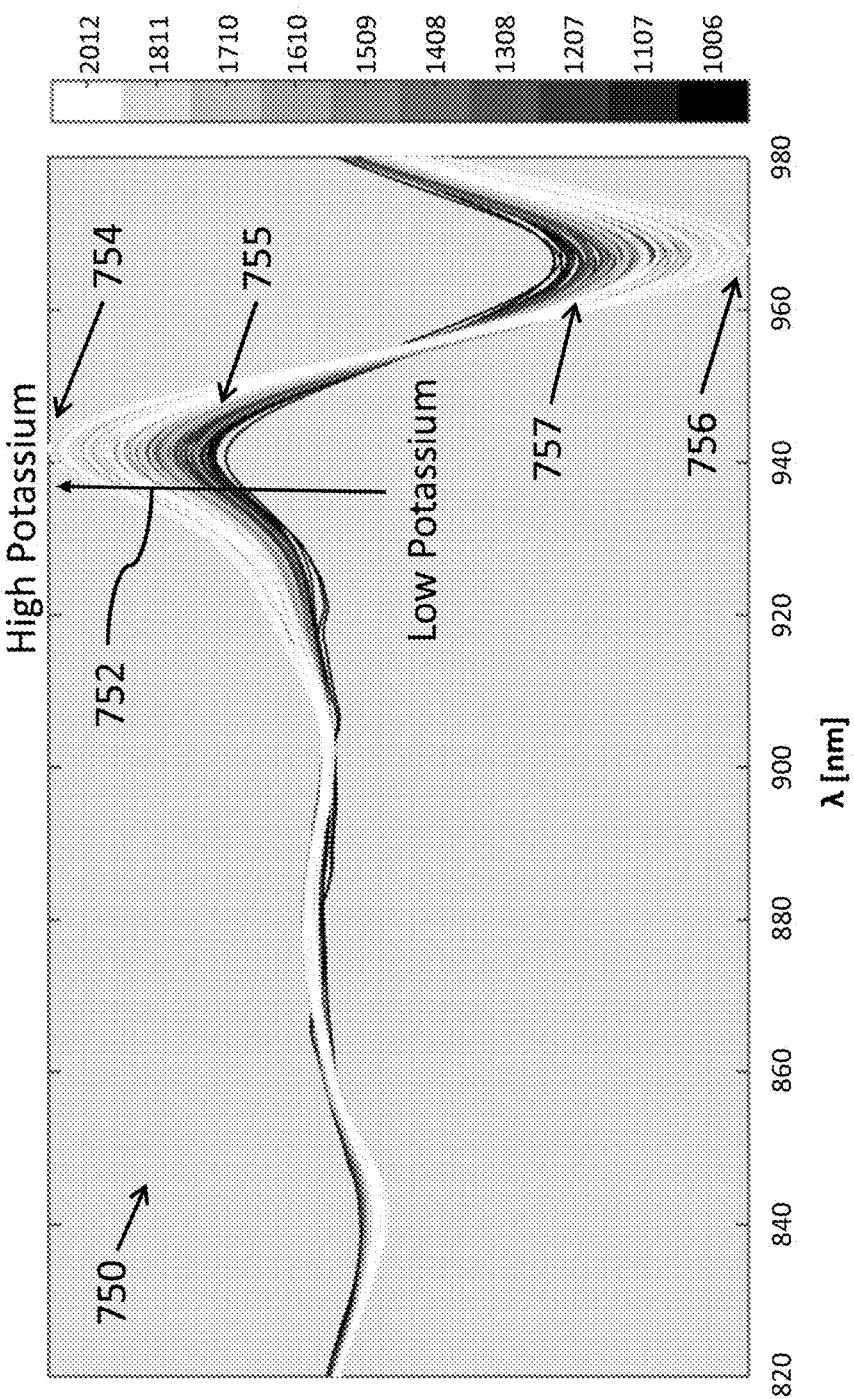
FIG. 29 shows exemplary spectra of aqueous solutions comprising various levels of potassium, suitable for incorporation in accordance with configurations.

FIGS. 27-29 show exemplary spectra of various components of urine in an aqueous solution, suitable for incorporation into a method of urine analysis in accordance with configurations. For example, the spectrometer system may be used to detect the levels of creatinine, sodium, and potassium in a sample of urine, and the sodium and potassium levels may be normalized with respect to the creatinine levels in order to provide a meaningful measure of the user's salt intake. Such a method for urine analysis using the spectrometer system is described in further detail herein with reference to FIG. 23.

FIG. 27 shows exemplary spectra of aqueous solutions comprising various levels of creatinine, suitable for incorporation in accordance with configurations. The spectra share general characteristic features in the wavelength range of about 1620 nm to about 1730 nm that enable their identification as spectra of solutions containing creatinine 730, but also have differences in their features that correspond to differences in the relative levels of the measured creatinine. In the spectra shown in FIG. 27, the spectra trend from having relatively lower creatinine levels to relatively higher creatinine levels in the direction indicated by arrow 732. For example, the spectra of solutions having higher levels of creatinine tend to have higher peaks 734, centered at about 1703 nm, compared to the corresponding peaks 735, also centered at about 1703 nm, of the spectra of solutions having lower levels of creatinine. Also, the spectra of solutions having higher levels of creatinine tend to have lower valleys 736, centered at about 1677 nm, compared to the corresponding valleys 737, also centered at about 1677 nm, of the spectra of solutions having lower levels of creatinine.

FIG. 28 shows exemplary spectra of aqueous solutions comprising various levels of sodium, suitable for incorporation in accordance with configurations. The spectra share general characteristic features in the wavelength range of about 1350 nm to about 1550 nm that enable their identification as spectra of solutions containing sodium 740, but also have differences in their features that correspond to differences in the relative levels of the measured sodium. In the spectra shown in FIG. 28, the spectra trend from having relatively lower sodium levels to relatively higher sodium levels in the direction indicated by arrow 742. For example, the spectra of solutions having higher levels of sodium tend to have higher peaks 744 (centered at about 1388 nm) and 746 (centered at about 1450 nm) compared to the corresponding peaks 745 (centered at about 1390 nm) and 747 (centered at about 1444 nm) of the spectra of solutions having lower levels of sodium. Also, the spectra of solutions having higher levels of sodium tend to have lower valleys 748 (centered at about 1415 nm) compared to the corresponding valleys 749 (centered at about 1415 nm) of the spectra of solutions having lower levels of sodium.

FIG. 29 shows exemplary spectra of aqueous solutions comprising various levels of potassium, suitable for incorporation in accordance with configurations. The spectra share general characteristic features in the wavelength range of about 820 nm to about 980 nm that enable their identification as spectra of solutions containing potassium 750, but also have differences in their features that correspond to differences in the relative levels of the measured sodium. In the spectra shown in FIG. 29, the spectra trend from having relatively lower potassium levels to relatively higher potassium levels in the direction indicated by arrow 752. For example, the spectra of solutions having higher levels of potassium tend to have higher peaks 754 (centered at about 942 nm) compared to the corresponding peaks 755 (centered at about 942 nm) of the spectra of solutions having lower levels of potassium. Also, the spectra of solutions having higher levels of potassium tend to have lower valleys 756 (centered at about 968 nm) compared to the corresponding valleys 757 (centered at about 968 nm) of the spectra of solutions having lower levels of potassium.

As shown in FIGS. 27-29, differences in one or more spectral features among spectra of solutions having similar general compositions (e.g., creatinine, sodium, potassium) can provide a means for obtaining a relative measurement of the level of each component. The spectrometer system as described herein may identify such differences by comparing the measured spectral data against the spectral data for a specific material component stored in the universal database, and provide the user with information regarding the composition of the measured sample.

The spectra of cheeses shown in FIGS. 24 and 25 have been acquired using a spectrometer system and device in accordance with configurations. The spectra of plums, shown in FIGS. 24 and 26, and the spectra of creatinine, sodium, and potassium in aqueous solutions, shown in FIGS. 27-29, show spectra suitable for incorporation in accordance with configurations described herein, and a person of ordinary skill in the art can configure the spectrometer to make suitable spectral measurements without undue experimentation. For example, in order to provide measurements of creatinine levels as described herein, the spectrometer device may be configured to comprise a combination of the various optical structures disclosed herein. One such exemplary configuration may comprise a filter-based optics structure as described herein, combined with multiple illumination sources as described herein. Another exemplary configuration may comprise modifying the filter-based optics structure disclosed herein to enable its detection of a lower-intensity signal of creatinine that falls within the detected wavelength range of the optical system. Alternatively or in combination, a substance may be added to urine samples to increase the signal intensity of the samples at the wavelength ranges detected by the optical systems described herein. The processor of the spectrometer system can be configured with instructions to perform specific steps in order to provide actionable insights or information to the user. For example, for the urine analysis method as described herein, the processor may be configured to compare the ratio of sodium to creatinine, in order to normalize the results presented to the user.

The methods and apparatus disclosed herein can be incorporated with components from spectrometers known in the art, such as spectrometers described in U.S. Pat. Nos. 8,284,401, 7,236,243, U.S. Publication No. 2015/0036138, U.S. Pat. No. 9,060,113, and U.S. Publication No. 2014/0061486, the entire disclosures of which are incorporated herein by reference.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A system to measure spectra of a sample, comprising:
a spectrometer to measure the spectra of the sample;
a processing device coupled to the spectrometer, the processing device comprising a processor and a wireless communication circuitry to couple to the spectrometer and communicate with a remote server, the processor comprising instructions to transmit spectral data of the sample to the remote server and receive object data in response to the spectral data from the remote server;

wherein the spectrometer is physically integrated with an apparatus comprising a mobile phone case, wherein information obtained with the spectrometer is provided to a functional feature of the processing device to improve a performance of the functional feature of the processing device, and wherein the functionality of the processing device comprises a camera, and the information obtained with the spectrometer is provided to the camera to improve a color correction algorithm of the camera.

2. The system of claim 1, wherein the color correction algorithm comprises a white balancing algorithm.

3. The system of claim 1, wherein the information obtained with the spectrometer comprises one or more illumination types of one or more sources of illumination present in a scene imaged by the camera, the one or more illumination types determined via an analysis of the spectral data of the scene obtained with the spectrometer.

\* \* \* \* \*